US011957629B2

(12) United States Patent
Strydom et al.

(10) Patent No.: US 11,957,629 B2
(45) Date of Patent: Apr. 16, 2024

(54) SYSTEMS AND METHODS FOR ASSISTING SURGERY

(71) Applicant: STRYKER AUSTRALIA PTY LTD, Artarmon (AU)

(72) Inventors: Mario Llewellyn Strydom, Riverview (AU); Jonathan Michael Roberts, Toowong (AU); Ross William Crawford, Windsor (AU); Anjali Tumkur Jaiprakash, Ashgrove (AU)

(73) Assignee: Stryker Australia PTY LTD, Artarmon Nsw (AU)

(*) Notice: Subject to any disclaimer, the term of this patent is extended or adjusted under 35 U.S.C. 154(b) by 937 days.

(21) Appl. No.: 16/791,614

(22) Filed: Feb. 14, 2020

(65) Prior Publication Data

US 2020/0261297 A1 Aug. 20, 2020

(30) Foreign Application Priority Data

Feb. 14, 2019 (AU) ................................ 2019900476

(51) Int. Cl.
*A61B 8/00* (2006.01)
*A61B 34/20* (2016.01)
(Continued)

(52) U.S. Cl.
CPC .......... *A61G 13/1295* (2013.01); *A61B 34/20* (2016.02); *A61B 34/30* (2016.02); *A61G 13/0063* (2016.11); *A61G 13/0081* (2016.11); *A61G 13/1245* (2013.01); *G06T 7/11* (2017.01); *G06T 7/60* (2013.01);
(Continued)

(58) Field of Classification Search
CPC ...................................................... A61B 34/20
See application file for complete search history.

(56) References Cited

U.S. PATENT DOCUMENTS 5,007,912 A 4/1991 Albrektsson et al.
5,645,079 A 7/1997 Zahiri et al.
(Continued)

FOREIGN PATENT DOCUMENTS

EP 0201883 A2 11/1986
WO 2019135805 A1 7/2019

OTHER PUBLICATIONS

Ward, Benjamin D. et al., "Basic knee arthroscopy part 3: diagnostic arthroscopy", Arthroscopy techniques, vol. 2, vol. 4, 2013, pp. e503-e505.

(Continued)

*Primary Examiner* — Joel F Brutus
(74) *Attorney, Agent, or Firm* — Howard & Howard Attorneys PLLC

(57) ABSTRACT

Disclosed are systems and methods for assisting with procedures involving a subject's joint, such as a joint. Robotic devices move and position the subject to manipulate the joint and sensing devices sense the joint gap. The robotic devices are controlled based on the joint gap. Novel techniques are disclosed for joint gap segmentation, approximating an uncertainty in determination of the varying dimension of the joint gap, and real-time motion analysis of the joint gap size. In some examples, a kinematic model of the patient's anatomy is utilized to provide robotically assisted manipulation of the same using the techniques described herein.

31 Claims, 51 Drawing Sheets

(51) Int. Cl.

| | |
|---|---|
| *A61B 34/30* | (2016.01) |
| *A61G 13/00* | (2006.01) |
| *A61G 13/12* | (2006.01) |
| *G06T 7/11* | (2017.01) |
| *G06T 7/60* | (2017.01) |

(52) U.S. Cl.

CPC ................. *A61B 2034/2048* (2016.02); *A61B 2034/2051* (2016.02); *A61B 2034/2055* (2016.02); *A61B 2034/2065* (2016.02); *A61B 2034/2072* (2016.02); *A61B 2034/301* (2016.02); *A61G 2203/20* (2013.01); *G06T 2207/10068* (2013.01); *G06T 2207/30008* (2013.01); *G06T 2207/30196* (2013.01)

(56) References Cited

U.S. PATENT DOCUMENTS

| | | | | |
|---|---|---|---|---|
| 10,136,592 | B2 | 11/2018 | Broutin Farah et al. | |
| 2009/0012533 | A1* | 1/2009 | Barbagli | A61B 34/70 606/130 |
| 2009/0046908 | A1* | 2/2009 | Safdar | A61B 5/4514 382/128 |
| 2012/0046540 | A1* | 2/2012 | Branch | A61B 5/459 600/407 |
| 2013/0245824 | A1* | 9/2013 | Barajas | B25J 9/1664 901/46 |
| 2013/0331850 | A1* | 12/2013 | Bojarski | A61F 2/4657 606/102 |
| 2014/0188129 | A1 | 7/2014 | Kang | |
| 2015/0094736 | A1 | 4/2015 | Malackowski et al. | |
| 2017/0027797 | A1 | 2/2017 | Dolliver et al. | |
| 2017/0165142 | A1 | 6/2017 | Gockeritz et al. | |
| 2017/0303849 | A1* | 10/2017 | De Sapio | A61N 1/36031 |
| 2017/0340389 | A1* | 11/2017 | Otto | A61B 5/1077 |
| 2017/0360512 | A1 | 12/2017 | Couture et al. | |
| 2017/0360513 | A1* | 12/2017 | Amiot | A61B 34/20 |
| 2018/0110667 | A1 | 4/2018 | Freeman et al. | |

OTHER PUBLICATIONS

Williams, A. et al., "Understanding tibio-femoral motion," The Knee, vol. 11, No. 2, 2004, pp. 81-84.

Wilson, D. et al., "The components of passive knee movement are coupled to flexion angle," Journal of Biomechanics, vol. 33, No. 4, 2000, pp. 465-473.

Wu, L. et al., "An analytic approach to converting poe parameters into d 8211;h parameters for seriallink robots," IEEE Robotics and Automation Letters, vol. 2, No. 4, 2017, pp. 2174-2179.

Wu, Liao et al., "Handbook of Robotic and Image-Guided Surgery", Chapter 29, Elsvier, 2019, pp. 493-514.

Xu, S. et al., "Characteristic analysis of Otsu threshold and its applications", Pattern Recognition Letters, vol. 32, No. 7, 2011, pp. 956-961.

Abstract of Xu, Z. et al., "Depth measurement using monocular stereo vision system: aspect of spatial discretization," Optoelectronic Imaging and Multimedia Technology, Phototonics Asia, 2010, pp. 785020-785029, 3 pages.

Yang, D. et al., "Simultaneous estimation of ego-motion and vehicle distance by using a monocular camera," Science China Information Sciences, vol. 57, No. 5, 2014, pp. 1-10.

Yang, R. et al., "Design of an accurate near infrared optical tracking system in surgical navigation," J. Light. Technol., vol. 31, No. 2, 2013, pp. 223-231.

Ye, M. et al., "Self-Supervised Siamese Learning on Stereo Image Pairs for Depth Estimation in Robotic Surgery," ArXiv e-prints, 2017, 2 pages.

Zhang, Y. et al., "Hybrid structured light for scalable depth sensing," Image Processing (ICIP), 19th IEEE International Conference, 2012, pp. 17-20.

Zhu, M. et al., "Geometry of signed point-to-surface distance function and its application to surface approximation," Journal of computing and information science in engineering, vol. 10, No. 4, 2010, p. 041003.

Ali, M.A. et al., "Closed-form inverse kinematic joint solution for humanoid robots," IEEE/RSJ International Conference on Intelligent Robots and Systems, IROS 2010—Conference Proceedings, 2010, pp. 704-709.

Abstract of Allen, M.W. et al., "Robotics in Knee and Hip Arthroplsty: Chapter 2—Evolution of Robotics in Arthroplasty", Springer International Publishing, 2019, p. 13, 15 pages.

Antico, M. et al., "Ultrasound guidance in minimally invasive robotic procedures," Medical Image Analysis, http://www. sciencedirect.com/science/article/pii/S1361841519300027, 2019, pp. 149-167.

Apkarian, J. et al., "A three-dimensional kinematic and dynamic model of the lower limb," Journal of Biomechanics, vol. 22, No. 2, 1989, pp. 143-155.

Bai, X. et al., "Principal pixel analysis and SVM for automatic image segmentation", Neural Computing and Applications, vol. 27, No. 1, 2016, pp. 45-58.

Bartoli, A. et al., "Computer assisted minimally invasive surgery: is medical computer vision the answer to improving laparosurgery?", Medical hypotheses, vol. 79, No. 6, 2012, pp. 858-863.

Beardsley, P.A. et al., "Navigation using affine structure from motion," European Conference on Computer Vision. Springer, 1994, pp. 85-96.

Bieniek, A. et al., "An efficient watershed algorithm based on connected components", Pattern Recognition, vol. 33, No. 6, 2000, pp. 907-916.

Blankevoort, L. et al., "The envelope of passive knee joint motion," Journal of Biomechanics, vol. 21, No. 9, 1988, pp. 705-720.

Bleau, A. et al., "Watershed-Based Segmentation and Region Merging", Computer Vision and Image Understanding, vol. 77, No. 3, 2000, pp. 317-370.

Cao, Y. et al., "Accurate numerical methods for computing 2d and 3d robot workspace," International Journal of Advanced Robotic Systems, vol. 8, No. 6, 2011, pp. 1-13.

Caselles, V. et al., "A geometric model for active contours in image processing", Numerische Mathematik, vol. 66, No. 1, 1993, pp. 1-31.

Caselles, V. et al., "Geodesic Active Contours", International Journal of Computer Vision, vol. 22,No. 1, 1997, pp. 61-79.

Chan T.F. et al., "Active Contours Without Edges", IEEE Transactions on Image Processing, vol. 10, No. 2, 2001, pp. 266-277.

Charlton, P. et al., "Repeatability of an optimised lower body model," Gait Posture, vol. 20, No. 2, 2004, pp. 213-221.

Chwa, D. et al., "Range and motion estimation of a monocular camera using static and moving objects," IEEE Transactions on Control Systems Technology, vol. 24, No. 4, 2016, pp. 1174-1183.

Collings, T et al., "3D reconstruction in laparoscopy with close-range photometric stereo," International Conference on Medical Image Computing and Computer-Assisted Intervention, Springer, 2012, pp. 634-642.

Cootes T.F. et al., "Active Shape Models-Their Training and Application", Computer Vision and Image Understanding, vol. 61, No. 1, 1995, pp. 38-59.

Corke, P. et al., "Robotics, vision and control: fundamental algorithms in MATLAB", Berlin: Springer, 2011, vol. 73, https://www.slideshare.net/WenChihPei/robotics-vision-and-control-fundamental-algorithms-in-matlab, 572 pages.

Crevier, D. et al., "Image segmentation algorithm development using ground truth image data sets", Computer Vision and Image Understanding, vol. 112, No. 2, 2008, pp. 143-159.

Dahiteb, "Arthroscopes Webpage", 2015, http://www.dahiteb.com/products/endoscopy/arthroscopy/ arthroscopes.html, 4 pages.

De Asla, R. J. et al., "Six DOF in vivo kinematics of the ankle joint complex: Application of a combined dual-orthogonal fluoroscopic and magnetic resonance imaging technique," Journal of Orthopaedic Research, vol. 24, No. 5, 2006, pp. 1019-1027.

Demirkaya, O. et al., "Determination of image bimodality thresholds for different intensity distributions", Signal Processing: Image Communication, vol. 19, No. 6, 2004, pp. 507-516.

(56) References Cited

OTHER PUBLICATIONS

Doyle, J. R. et al., "The Arthroscope, Then and Now," Techniques in Hand & Upper Extremity Surgery, vol. 12, No. 4, Dec. 2008, p. 201.
Field, M. et al., "Stereo endoscopy as a 3-d measurement tool," Engineering in Medicine and Biology Society, Annual International Conference of the IEEE. 2009, pp. 5748-5751.
Abstract of Freeman, M. et al., "The movement of the normal tibio-femoral joint," Journal of Biomechanics, vol. 38, No. 2, 2005, pp. 197-208, 3 pages.
Fujie, G., "Forces and moments in six-DOF at the human knee joint: mathematical description for control," Journal of biomechanics, 1996, pp. 1577-1585.
Funck, J.W. et al., "Image segmentation algorithms applied to wood defect detection", Computers and Electronics in Agriculture, vol. 41, No. 1, 2003, pp. 157-179.
Hartley, R. et al., "Stereo from uncalibrated cameras," Computer Vision and Pattern Recognition, 1992. Proceedings CVPR, IEEE Comuter Society Conference, 1992, pp. 761-764.
Hill P.F. et al., "Tibiofemoral movement 2: the loaded and unloaded living knee studied by MRI," The Journal of bone and joint surgery, British volume, vol. 82, No. 8, 2000, pp. 1196-1198.
Huang, F. et al., "Moment based Shape Priors for Geometric Active Contours". IEEE, vol. 2, 2006, pp. 56-59.
International-Type Search Report for Application No. AU 2019900476 dated Mar. 20, 2019, 3 pages.
Iwaki, H. et al., "Tibiofemoral movement 1: the shapes and relative movements of the femur and tibia in the unloaded cadaver knee," The Journal of bone and joint surgery, British volume, vol. 82, No. 8, 200, pp. 1189-1195.
Jaiprakash, J.M. et al., "Orthopeadic Surgeons Attitudies Towards Current Limitations and the Potential for Robotic and Technological Innovation in Arthroscopic Surgery", Journal of Orthopaedic Surgery, vol. 25, No. 1, 2017, pp. 1-6.
Abstract of Janabi-Sharifi, F. "Advances in Motion Sensing and Control for Robotic Applications: Selected Papers from the Symposium on Mechatronics, Robotics, and Control", CSME International Congress, May 27-30, 2018 TorontoCanada. Springer, 5 pages.
Jarvis, R.A. et al., "A Perspective on Range Finding Techniques for Computer Vision," IEEE Transactions on Pattern Analysis and Machine Intelligence, vol. PAMI-5, No. 2, Mar. 1983, pp. 122-139.
Jarvis, R.A., "Computer Vision and Robotics Laboratory", IEEE, Computer Journal, United States, vol. 15, No. 6, Jun. 1982, 16 pages.
Jenkyn, T.R. et al., "A multi-segment kinematic model of the foot with a novel definition of forefoot motion for use in clinical gait analysis during walking," Journal of Biomechanics, vol. 40, 2007, pp. 3271-3278.
Abstract of Johal, P. et al., "Tibiofemoral movement in the living knee—A study of weight bearing and non-weight bearing knee kinematics using 'interventional' MRI," Journal of Biomechanics, vol. 38, No. 2, 2005, pp. 269-276, 3 pages.
Kainz, H. et al., "Estimation of the hip joint centre in human motion analysis: A systematic review," Clin. Biomech., No. 4, 2015, pp. 319-329.
Abstract of Kaneko, K. et al., "Humanoid robot HRP-3," IEEE/RSJ International Conference on Intelligent Robots and Systems. 2008, pp. 2471-2478, 1 page.
Kim, G. et al. "Accuracy and reliability of length measurements on threedimensional computed tomography using open-source osirix software," Journal of digital imaging, vol. 25, No. 4, 2012, pp. 486-491.
Kouyoumdjian, R. et al., "Clinical evaluation of hip joint rotation range of motion in adults," Orthopaedics & Traumatology: Surgery & Research, vol. 98, No. 1, 2012, pp. 17-23.
Leardini, A. et al., "A geometric model of the human ankle joint," Journal of Biomechanics, vol. 32, No. 6, 1999, pp. 585-591.
Lewis, R. et al., "A scanning laser rangefinder for a robotic vehicle," Techical Memorandom 33-809, 1977, 84 Pages.
Li, A. et al., "Medical image segmentation based on maximum entropy multi-threshold segmentation optimized by improved cuckoo search algorithm", in Image and Signal Processing (CISP), 8th International Congress, IEEE, 2015, pp. 470-475.
Li, G., et al., "New fluoroscopic imaging technique for investigation of 6DOF knee kinematics during treadmill gait," Journal of Orthopaedic Surgery and Research, No. 1, 2009, 5 pages.
Litjens, T. et al. "A survey on deep learning in medical image analysis," Medical Image Analysis, vol. 42, 2017, pp. 60-88.
Lu, T.-W. et al., "Bone position estimation from skin marker co-ordinates using global optimisation with joint constraints," Journal of biomechanics, vol. 32, No. 2, 1999, pp. 129-134.
Ma, Zhen. et al.., "A review of algorithms for medical image segmentation and their applications to the female pelvic cavity", Computer Methods in Biomechanics and Biomedical Engineering, vol. 13, No. 2, 2010, pp. 235-246.
Maletsky, L.P. "Accuracy of an optical active-marker system to track the relative motion of rigid bodies," J. Biomech., vol. 40, No. 3, 2007, pp. 682-685.
Maletsky, L.P. et al., "Accuracy of an optical active-marker system to track the relative motion of rigid bodies," J. Biomech., vol. 40, No. 3, 2007, pp. 682-685.
Malladi, J.A. et al., "Topology-independent shape modeling scheme", Geometric Methods in Computer Vision II, vol. 2031 SPIE, Jun. 23, 1993, pp. 246-258.
Marmol, A. et al., "Evaluation of keypoint detectors and descriptors in arthroscopic images for feature-based matching applications," IEEE Robotics and Automation Letters, vol. 2, No. 4, 2017, pp. 2135-2142.
Mathworks, "Marker-Controlled Watershed Segmentation", 2016, https://www.mathworks.com/help/images/marker-controlled-watershed-segmentation.html, 15 pages.
Mathworks, "OTSU Matlab Code/Graythresh", 2016, https://www.mathworks.com/help/images/ref/graythresh.html, 3 pages.
Mazzon, R., "Real-time structure from motion for monocular and stereo cameras," MELECON 15th IEEE Mediterranean Electrotechnical Conference. IEEE, 2010, pp. 498-503.
Abstract of McKeon, B.P. et al., "Knee Arthroscopy", Textbook, Springer, New York, NY, 2009, 9 pages.
McPherson, A. et al., "Imaging knee position using MRI, RSA/CT and 3D digitisation," Journal of biomechanics, vol. 38, No. 2, 2005, pp. 263-268.
Moglo, K. et al., "Cruciate coupling and screwhome mechanism in passive knee joint during extension flexion," Journal of Biomechanics, vol. 38, No. 5, 2005, pp. 1075-1083.
Morrison, C. et al., "Collaborating with computer vision systems: an exploration of audio feedback," Proceedings of the conference on Designing interactive systems,. ACM, 2014, pp. 229-238.
Mumford, D. et al., "Optimal approximations by piecewise smooth functions and associated variational problems", Communications on Pure and Applied Mathematics, vol. 42, No. 5, 1989, pp. 577-685.
Nagymate, G. et al., "A novel validation and calibration method for motion capture systems based on micro-triangulation," J. Biomech., vol. 74, 2018, pp. 16-22.
Nam, et al., "Application of stereo-imaging technology to medical field," Healthcare informatics research, vol. 18, No. 3, 2012, pp. 158-163.
Abstract of Nevatia, R., "Depth measurement by motion stereo," Computer Graphics and Image Processing, vol. 5, No. 2, 1976, pp. 203-214, 3 pages.
Nigg, B.M. et al., "Abstract/Description of Biomechanics of the musculo-skeletal system", Wiley, 3rd Edition, Mar. 2007, 3 pages.
Abstract of Nikolay, S., "Active Contours implementation & test platform", GUI, 2013, 16 Pages.
Nixon, M.S. et al., "Feature extraction & image processing for computer vision", vol. 3, Elsevier, Oxford, 2012, 360 pages.
Nussbaumer, M. et al., "Validity and test-retest reliability of manual goniometers for measuring passive hip range of motion in femoroacetabular impingement patients," BMC Musculoskeletal Disorders, vol. 11, No. 1, 2010, 11 pages.
Osher, S. et al., "Fronts propagating with curvature dependent speed: Algorithms based on Hamilton-Jacobi formulations", Journal of Computational Physics, vol. 79, No. 1, 1988, pp. 12-49.

(56) References Cited

OTHER PUBLICATIONS

Otsu, N., "A Threshold Selection Method from Gray-Level Histograms", IEEE Transactions on Systems, Man, and Cybernetics, vol. 9, No. 1, 1979, pp. 62-66.
Papadhimitri, T. et al., "A new perspective on uncalibrated photometric stereo," Proceedings of the IEEE Conference on Computer Vision and Pattern Recognition, 2013, pp. 1474-1481.
Park, F., "Computational aspects of the product-of-exponentials formula for robot kinematics," IEEE Transactions on Automatic Control, 1994, vol. 39, No. 3, pp. 643-647.
Prather, H. et al., "Hip Range of Motion and Provocative Physical Examination Tests Reliability and Agreement in Asymptomatic Volunteers", PMRJ, vol. 2, 2010, pp. 888-895.
Qut, "Australia's First Robotics Hub to Drive Advanced Manufacturing Jobs", Jul. 24, 2019, 9 pages.
Rasool, S. et al., "Image-driven virtual simulation of arthroscopy," The Visual Computer, vol. 29, No. 5, 2013, pp. 333-344.
Reinbolt, J.A. et al., "Determination of patient-specific multi-joint kinematic models through two-level optimization," Journal of Biomechanics, vol. 38, 2005, pp. 621-626.
Rice, J.J., "Healthcare Bluebook Webpage", 2015, 4 pages.
Robinette, M. et al., "Robot-Draw, an Internet-based visualization tool for robotics education," IEEE Transactions on Education, vol. 44, No. 1, 2001, pp. 29-34.
Abstract of Rohl, S. et al., "Real-time surface reconstruction from stereo endoscopic images for intraoperative registration," Medical Imaging 2011: Visualization, Image-Guided Procedures, and Modeling, vol. 7964, International Society for Optics and Photonics, 2011, p. 796414, 3 pages.
Sarti, A. et al., "Subjective Surfaces: A Geometric Model for Boundary Completion", International Journal of Computer Vision, vol. 46, No. 3, 2002, pp. 201-221.
Saxena, A. et al., "Depth estimation using monocular and stereo cues." IJCAI, vol. 7, 2007, 7 pages.
Scaramuzza, D. et al., "Absolute scale in structure from motion from a single vehicle mounted camera by exploiting nonholonomic constraints," Computer Vision, IEEE 12th International Conference. IEEE, 2009, pp. 1413-1419.
Scuderi, R. et al., "Abstract and Chapter 1 of the knee : a comprehensive review",. World Scientific, 2010, 26 pages.
Stoyanov, D. et al., "Real-time stereo reconstruction in robotically assisted minimally invasive surgery," International Conference on Medical Image Computing and Computer-Assisted Intervention. Springer, 2010, pp. 275-282.
Stoyanov, D., "Surgical vision," Annals of biomedical engineering, vol. 40, No. 2, 2012, pp. 332-345.
Strydom, Mario et al., Approximation of the Uncertainty Point-Cloud for Monocular Knee Joint Measurement, 2016, 8 pages.
Strydom, Mario et al., "Human Leg Kinematic Model for Minally Invasive Knee Arthroscopy", Queensland University of Technology, Brisbane Austraila, 8 pages.
Strydom, Mario et al., "Real-Time Joint Motion Analysis and Instrument Tracking for Robot-Assisted Orthopaedic Surgery", 2019, 8 pages.
Strydom, Mario et al., "Robotic Arthroscopy: The Uncertainty in Internal Knee Joint Measurement", IEEE, 2019, 13 pages.
Strydom, Mario et al., "Towards robotic arthroscopy: 'Instrument gap' segmentation", Proceedings of the 2016 Australasian Conference on Robotics and Automation: Australian Robotics and Automation Association, Australia, 2016, pp. 1-10.
Abstract of Strydom, S. et al., "UAV Guidance: A Stereo-Based Technique for Interception of Stationary or Moving Targets", Conference Towards Autonomous Robotic Systems, Springer, 2015, pp. 258-269, 7 pages.
Stryker Mako, "Robotic Arm-Assisted Surgery Webpage", 2019, https://www.stryker.com/us/en/portfolios/orthopaedics/joint-replacement/mako-robotic-arm-assisted-surgery.html, 3 pages.
Tachibana, H. et al., "Determination of the optimized image processing and template matching techniques for a patient intrafraction motion monitoring system", Medical Physics, vol. 39, No. 2, 2012, pp. 755-764.
Tarabalka, Y. et al., "Segmentation and classification of hyperspectral images using watershed transformation", Pattern Recognition, vol. 43, No. 7, 2010, pp. 2367-2379.
Tsai, C.-C. et al., "Trajectory planning and control of a 7-DOF robotic manipulator," 2014 International Conference on Advanced Robotics and Intelligent Systems (ARIS). IEEE, 2014, pp. 78-84.
Victor, J. et al., "The influence of muscle load on tibiofemoral knee kinematics," Journal of Orthopaedic Research, vol. 28, No. 4, 2009, pp. 419-428.
Visentini-Scarzanella, M., et al., "Deep monocular 3d reconstruction for assisted navigation in bronchoscopy," International journal of computer assisted radiology and surgery, vol. 12, No. 7, 2017, pp. 1089-1099.
Wang, Jingqiu et al., "A Hybrid Method for the Segmentation of a Ferrerograph Image Using Marker-Controlled Watershed and Grey Clustering", Tribology Transaction, vol. 59, No. 3, 2016, pp. 513-521.
Abstract of Wang, Z.R. et al., Modeling and error analysis of monocular stereo vision system for large-scale workpiece on-machine measurement, Advanced Materials Research, vol. 102. Trans Tech Publ, 2010, pp. 397-401, 3 pages.

* cited by examiner (Paper 3 Fig 3c)

(Paper 3 Fig 9a)

(Paper 3 Fig 9b)

FIG. 35A $$DPP_x = \frac{Max\_Azimuth}{Image\_Width} = 0.075\ [^\circ/px]$$

$$DPP_y = \frac{Max\_Elevation}{Image\_Height} = 0.125\ [^\circ/px]$$

FIG. 35B $$\vec{a}_n = ||\vec{t}||\frac{\sin\alpha_n}{\sin\gamma_n}\hat{a}_n$$

FIG. 35C $$\vec{b}_n = ||\vec{t}||\frac{\sin\beta_n}{\sin\gamma_n}\hat{b}_n$$

FIG. 35D $$\alpha_n = \arccos\left(\frac{\vec{t}}{||\vec{t}||}\cdot\hat{b}_n\right)$$

FIG. 35E $$\beta_n = \arccos\left(-\frac{\vec{t}}{||\vec{t}||}\cdot\hat{a}_n\right)$$

FIG. 35F $$\gamma_n = \pi - (\alpha_n + \beta_n)$$

FIG. 35G $$d = ||\vec{g}|| = ||\vec{a}_1 - \vec{a}_0|| = ||\vec{b}_1 - \vec{b}_0||$$

FIG. 35H $$\vec{b}_n = ||\vec{t}||\frac{\sin\beta_n}{\sin\gamma_n}\hat{b}_n = ||\vec{t}||\frac{\sin\beta_n}{\sin(\alpha_n+\beta_n)}\hat{b}_n$$

FIG. 35I $$L = \tau\frac{\sin\alpha_n}{\sin(\alpha_n+\beta_n)}$$

FIG. 35J $$\Delta L = (\tau + \Delta\tau)\frac{\sin(\alpha_n + \Delta\alpha_n)}{\sin(\alpha_n + \Delta\alpha_n + \beta_n + \Delta\beta_n)} - L$$

$$\leq (\tau + \Delta\tau)\frac{\sin\alpha_n + \Delta\alpha_n}{\left(1 + \frac{\Delta\gamma_n}{\sin\gamma_n}\right)\sin\gamma_n} - L$$

$$\leq (\tau + \Delta\tau)\left[\left(\frac{\sin\alpha_n}{\sin\gamma_n} + \frac{\Delta\alpha_n}{\sin\gamma_n}\right)\left(1 - \frac{\Delta\gamma_n}{\sin\gamma_n}\right)\right] - L$$

FIG. 35K $$\Delta L = \tau\frac{\sin\alpha_n}{\sin\gamma_n} - \tau\Delta\gamma\frac{\sin\alpha_n}{\sin^2\gamma_n} + \tau\frac{\Delta\alpha_n}{\sin\gamma_n} + \Delta\tau\frac{\sin\alpha_n}{\sin\gamma_n} - \Delta\tau\Delta\gamma_n\frac{\sin\alpha_n}{\sin^2\gamma_n} + \Delta\tau\frac{\Delta\alpha_n}{\sin\gamma_n} - L$$

FIG. 35L $$\Delta L = \tau\left(\frac{\Delta\alpha_n}{\sin\gamma_n} - \frac{\Delta\gamma_n\sin\alpha_n}{\sin^2\gamma_n}\right) + \Delta\tau\frac{\sin\alpha_n}{\sin\gamma_n}$$

FIG. 35M $$A'_0 = \hat{r}_{(az,el)}\Delta T$$

$$A'_1 = \vec{t} + \hat{r}_{(az,el)}\Delta T$$

FIG. 35N $$\hat{r}_{(az,el)} = \begin{pmatrix} \sin(az)\cos(el) \\ \cos(az)\cos(el) \\ \sin(el) \end{pmatrix}$$

FIG. 35O $$\vec{r}_{p,q} = A'_{1q} - A'_{0p} \quad \text{where} \quad \begin{cases} p=1,2,\ldots P \\ q=1,2,\ldots Q \end{cases}$$

FIG. 35P $$\alpha'_n = \arccos\left(\hat{t}'_{p,q} \cdot \hat{b}_n\right) \pm \psi$$

$$\beta'_n = \arccos\left(-\hat{t}'_{p,q} \cdot \hat{a}_n\right) \pm \psi$$

FIG. 35Q $$\Delta\alpha_n = \alpha_n - \alpha'_n$$

$$\Delta\beta_n = \beta_n - \beta'_n$$

FIG. 35R $$E_0 = A'_0 + G_{0\phi}$$

$$E_1 = A'_1 + G_{1\phi}$$

FIG. 35S $$||\Delta\vec{g}_n|| = (L + \Delta L)\sin\psi$$

FIG. 35T $$\Delta\hat{g}_n = \frac{\left[\hat{b}_n \times (\hat{t}'_{pq} \times \hat{b}_n)\right]}{\left|\left|\left[\hat{b}_n \times (\hat{t}'_{pq} \times \hat{b}_n)\right]\right|\right|}$$

FIG. 35U $$\Delta\vec{g}_n = \frac{\left[\hat{b}_n \times (\hat{t}'_{pq} \times \hat{b}_n)\right]}{\left|\left|\left[\hat{b}_n \times (\hat{t}'_{pq} \times \hat{b}_n)\right]\right|\right|}(L + \Delta L)\sin\psi$$

FIG. 35V $$d_e = E_{1i} - E_{0j} \quad \text{and} \quad \begin{cases} \text{i=1,2,....I} \\ \text{j=1,2,....J} \end{cases}$$

FIG. 35W $$SNR_d = \frac{d}{d_{e(max)} - d_{e(min)}}$$

FIG. 35X

| | | | |
|---|---|---|---|
| el | $[-\frac{\pi}{2}, \frac{\pi}{2}]$ | el steps: | [4] |
| az | $[-\pi, \pi]$ | az steps: | [6] |
| $t$ | [Constant] | $\Delta T$ steps: | [0.01 : 0.3] |
| $\phi$ | $[-\pi, \pi]$ | $\phi$ steps: | $[0, \frac{\pi}{6}, \frac{\pi}{4}, \frac{\pi}{2}]$ |
| $\pm\omega$ | [Constant] | | |
| $\pm\theta$ | [Constant] | | |

FIG. 35Y $$E_0 = A'_0 + G_{0\phi}$$

$$E_1 = A'_1 + G_{1\phi}$$

FIG. 35Z $$d_e = E_{1i} - E_{0j} \quad \text{and} \quad \begin{cases} \text{i=1,2,....I} \\ \text{j=1,2,....J} \end{cases}$$

FIG. 36A $$\theta_T = \tanh \frac{2\Delta T}{||T||}$$

FIG. 36B $$r_{n_2} = (L_n + \Delta L_n) \sin \theta_T$$

FIG. 36C $$r_{n_1} = ||\vec{G}_n|| \\ = sin\Phi(L_n + \Delta L_n)$$

FIG. 36D $$d_{min} = ||G_1' - G_o'|| - R_o - R_1 - R_2$$

$$d_{max} = ||G_1' - G_o'|| + R_o + R_1 + R_2$$

FIG. 36E

| Set | Translation Angles | $\Delta T$ [mm] | Gap(d) [mm] | t [mm] | $\theta$ | $\omega$ |
|---|---|---|---|---|---|---|
| 1 | $0^o$, | 0.0367 | 4 | 2 | $2.36^o$ | $0.004^o$ |
| 2 | $30^o$, | 0.0367 | 4 | 2 | $2.36^o$ | $0.004^o$ |
| 3 | $60^o$, | 0.0367 | 4 | 2 | $2.36^o$ | $0.004^o$ |
| 4 | $60^o$, | 0.0367 | 4 | 8 | $2.36^o$ | $0.004^o$ |

TABLE 4: The average segmentation error is used and during set 4 the translation is 8mm.

FIG. 36F $$T_H = \begin{bmatrix} x_i & y_i & z_i & {}^{w}h_i \\ x_j & y_j & z_j & {}^{w}h_j \\ x_k & y_k & z_k & {}^{w}h_k \\ 0 & 0 & 0 & 1 \end{bmatrix} \in SO(3) \subset \mathbb{R}^3$$

FIG. 36J $$z = {}^{w}c - {}^{w}b \quad \text{frame z axis}(\textit{mechanical})$$
$$x' = {}^{w}b - {}^{w}k \quad \text{x' axis}$$
$$y = z \times x' \quad \text{y axis}$$
$$x = y \times z \quad \text{x axis}$$

FIG. 36K $$T_C = \begin{bmatrix} x & y & z & {}^{w}c_B \\ 0 & 0 & 0 & 1 \end{bmatrix} = \begin{bmatrix} R_B & {}^{w}c_B \\ 0 & 1 \end{bmatrix}$$

FIG. 36L $$\mathbf{v}_{t_x} = proj_{\mathbf{x}_n}\mathbf{v}_t = \frac{\mathbf{v}_t \cdot \mathbf{x}_n}{\|\mathbf{x}_n\|^2}\mathbf{x}_n$$
$$\mathbf{v}_{t_{yz}} = \mathbf{V}_t - \mathbf{V}_{t_x}$$

FIG. 36M $$\beta = \text{atan2}(\|\mathbf{v}_{\mathbf{t}_{yz}} \times \mathbf{v}_{\mathbf{t}}\|, \mathbf{v}_{\mathbf{t}_{yz}} \cdot \mathbf{v}_{\mathbf{t}})$$

FIG. 36N $$\alpha = \text{atan2}(\|\mathbf{v}_{\mathbf{t}_{xz}} \times \mathbf{v}_{\mathbf{t}}\|, \mathbf{v}_{\mathbf{t}_{xz}} \cdot \mathbf{v}_{\mathbf{t}})$$

FIG. 36O $$^{v_f}R_{v_t} = 2\frac{(t_r t_r^{-1})}{(t_r^{-1} t_r) - I}$$

FIG. 36P $$\gamma = \text{atan2}(-^{V_f}R_{v_t}(1,2), ^{V_f}R_{v_t}(1,1))$$

FIG. 36Q $$\psi = \text{atan2}(\|\mathbf{v}_{\mathbf{f}_{yz}} \times \mathbf{v}_{\mathbf{f}}\|, \mathbf{v}_{\mathbf{f}_{yz}} \cdot \mathbf{v}_{\mathbf{f}})$$

$$\theta = \text{atan2}(\|\mathbf{v}_{\mathbf{f}_{xz}} \times \mathbf{v}_{\mathbf{f}}\|, \mathbf{v}_{\mathbf{f}_{xz}} \cdot \mathbf{v}_{\mathbf{f}})$$

FIG. 36R $$\psi = \text{atan2}(-^{W}R_C(1,2), ^{W}R_C(1,1))$$

FIG. 36S

| Time [Sec] | $^{w}e_{c}$ Ex | Ey | Ez | $^{w}e_{cme}$ Ex | Ey | Ez |
|---|---|---|---|---|---|---|
| 00:11.033 | 1221.7 | 910.22 | 827.47 | 1221.6 | 909.495 | 827.47 |
| 01:48.492 | 933.06 | 859.26 | 1088.6 | 933.06 | 859.26 | 1088.6 |
| 02:42.500 | 1354.5 | 1135.4 | 848.75 | 1354.5 | 1135.4 | 848.75 |
| 03:40.525 | 1323 | 1188.6 | 1256.8 | 1323 | 1188.6 | 1256.8 |
| 04:37.517 | 1260.3 | 1064.4 | 835.7 | 1260.3 | 1064.4 | 835.7 |

TABLE 7: Ankle-E point 1) Direction from the world frame and 2) via frames C to M to E.

FIG. 36T

| Time | ${}^{w}e_D$ | | | Error |
|---|---|---|---|---|
| [Sec] | Ex | Ey | Ez | ${}^{w}e_C - {}^{w}e_D$ |
| 00:11.033 | 1221.6 | 909.495 | 827.47 | 0.7804 |
| 01:48.492 | 933.06 | 859.26 | 1088.6 | 0.7805 |
| 02:42.500 | 1354.5 | 1135.4 | 848.75 | 0.7935 |
| 03:40.525 | 1323 | 1188.6 | 1256.8 | 0.7995 |
| 04:37:517 | 1260.3 | 1064.4 | 835.7 | 0.7807 |

TABLE 8: Local Translation Error length

FIG. 36U

| Link | Type | Variable | DH Parameters | | | |
|---|---|---|---|---|---|---|
| | | | $\theta_i$ | $d_i$ | $a_i$ | $\alpha_i$ |
| 1 | T | Body Align | $\frac{\pi}{2}$ | q1 | 0 | $\frac{\pi}{2}$ |
| 2 | R | Hip Flexion | q2 | 0 | 0 | $\frac{\pi}{2}$ |
| 3 | R | Hip Varus | q3 | 0 | 0 | $\frac{\pi}{2}$ |
| 4 | R | Hip Rotation | q4 | L4 | 0 | $\frac{\pi}{2}$ |
| 5 | R | Knee Flexion | q5 | 0 | 0 | $\frac{\pi}{2}$ |
| 6 | T | Knee Sliding | $\frac{\pi}{2}$ | q6 | 0 | $\frac{\pi}{2}$ |
| 7 | R | Knee Varus | q7 | 0 | 0 | $-\frac{\pi}{2}$ |
| 8 | T | Knee Med/Lat | $-\frac{\pi}{2}$ | q8 | 0 | $-\frac{\pi}{2}$ |
| 9 | T | Knee Gap | 0 | q9 | 0 | 0 |
| 10 | R | Knee Rotation | q10 | L10 | 0 | 0 |

TABLE 10: DH Parameters for a 9 DOF leg with hip and knee links

FIG. 36V $$A_{leg} = \begin{bmatrix} r_{11} & r_{21} & r_{31} & r_{41} \\ r_{21} & r_{22} & r_{23} & r_{24} \\ r_{31} & r_{32} & r_{33} & r_{34} \\ r_{41} & r_{42} & r_{43} & r_{44} \end{bmatrix} \in SO(3) \subset \mathbb{R}^{3x3}$$

FIG. 36W $$r_{11} = c_{q_{10}}\left(c_{q_5} c_{q_6} + c_{q_4} s_{q_5} s_{q_6}\right) - s_{q_{10}}\left(s_{q_7}\left(c_{q_6} s_{q_5} - c_{q_4} c_{q_5} s_{q_6}\right) + c_{q_7} s_{q_3} s_{q_4}\right)$$

$$r_{12} = -c_{q_{10}}\left(s_{q_7}\left(c_{q_6} s_{q_5} - c_{q_4} c_{q_5} s_{q_6}\right) + c_{q_7} s_{q_3} s_{q_4}\right) - s_{q_{10}}\left(c_{q_5} c_{q_6} + c_{q_4} s_{q_5} s_{q_6}\right)$$

$$r_{13} = s_{q_3} s_{q_4} s_{q_7} - c_{q_7}\left(c_{q_6} s_{q_5} - c_{q_4} c_{q_5} s_{q_6}\right)$$

$$r_{14} = q_6\left(c_{q_5} c_{q_6} + c_{q_4} s_{q_5} s_{q_6}\right) - \frac{7 c_{q_5}}{10} - c_{q_7}\left(c_{q_5} s_{q_5} - c_{q_4} c_{q_5} s_{q_5}\right) + q_8\left(s_{q_7}\left(c_{q_5} s_{q_5} - c_{q_4} c_{q_5} s_{q_6}\right) + c_{q_7} s_{q_3} s_{q_4}\right)$$
$$- q_9\left(c_{q_7}\left(c_{q_5} s_{q_5} - c_{q_4} c_{q_6} s_{q_5}\right) - s_{q_3} s_{q_4} s_{q_7}\right) + s_{q_3} s_{q_4} s_{q_7}$$

$$r_{21} = c_{q_{10}}\left(s_{q_5}\left(s_{q_3} s_{q_4} + c_{q_3} c_{q_5} c_{q_4}\right) - c_{q_3} c_{q_6} s_{q_5}\right) + s_{q_{10}}\left(s_{q_7}\left(c_{q_6}\left(s_{q_3} s_{q_4} + c_{q_3} c_{q_5} c_{q_4}\right) + c_{q_3} s_{q_5} s_{q_6}\right)\right.$$
$$\left. + c_{q_7}\left(c_{q_4} s_{q_3} - c_{q_3} c_{q_3} s_{q_4}\right)\right)$$

$$r_{22} = c_{q_{10}}\left(s_{q_7}\left(c_{q_6}\left(s_{q_3} s_{q_4} + c_{q_3} c_{q_5} c_{q_4}\right) + c_{q_3} s_{q_5} s_{q_6}\right) + c_{q_7}\left(c_{q_4} s_{q_3} - c_{q_3} c_{q_3} s_{q_4}\right)\right)$$
$$- s_{q_{10}}\left(s_{q_5}\left(s_{q_3} s_{q_4} + c_{q_3} c_{q_5} c_{q_4}\right) - c_{q_3} c_{q_6} s_{q_5}\right)$$

$$r_{23} = c_{q_7}\left(c_{q_6}\left(s_{q_3} s_{q_4} + c_{q_3} c_{q_5} c_{q_4}\right) + c_{q_3} s_{q_5} s_{q_6}\right) - s_{q_7}\left(c_{q_4} s_{q_3} - c_{q_3} c_{q_3} s_{q_4}\right)$$

$$r_{24} = q_9\left(c_{q_7}\left(c_{q_6}\left(s_{q_3} s_{q_4} + c_{q_3} c_{q_5} c_{q_4}\right) + c_{q_3} s_{q_5} s_{q_6}\right) - s_{q_7}\left(c_{q_4} s_{q_3} - c_{q_3} c_{q_3} s_{q_4}\right)\right)$$
$$- q_8\left(s_{q_7}\left(c_{q_6}\left(s_{q_3} s_{q_4} + c_{q_3} c_{q_5} c_{q_4}\right) + c_{q_3} s_{q_5} s_{q_6}\right) + c_{q_7}\left(c_{q_4} s_{q_3} - c_{q_3} c_{q_3} s_{q_4}\right)\right) + \frac{7 c_{q_3} s_{q_5}}{10}$$
$$+ c_{q_7}\left(c_{q_6}\left(s_{q_3} s_{q_4} + c_{q_3} c_{q_5} c_{q_4}\right) + c_{q_3} s_{q_5} s_{q_6}\right) - s_{q_7}\left(c_{q_4} s_{q_3} - c_{q_3} c_{q_3} s_{q_4}\right) + q_6\left(s_{q_5}\left(s_{q_3} s_{q_4} + c_{q_3} c_{q_5} c_{q_4}\right) - c_{q_3} c_{q_6} s_{q_5}\right.$$

$$r_{31} = -c_{q_{10}}\left(s_{q_5}\left(c_{q_3} s_{q_4} - c_{q_3} c_{q_4} s_{q_3}\right) + c_{q_5} s_{q_3} s_{q_5}\right) - s_{q_{10}}\left(s_{q_7}\left(c_{q_6}\left(c_{q_3} s_{q_4} - c_{q_5} c_{q_4} s_{q_3}\right) - s_{q_3} s_{q_5} s_{q_6}\right)\right.$$
$$\left. + c_{q_7}\left(c_{q_3} c_{q_4} + c_{q_3} s_{q_3} s_{q_4}\right)\right)$$

$$r_{32} = s_{q_{10}}\left(s_{q_5}\left(c_{q_3} s_{q_4} - c_{q_3} c_{q_4} s_{q_3}\right) + c_{q_5} s_{q_3} s_{q_5}\right) - c_{q_{10}}\left(s_{q_7}\left(c_{q_6}\left(c_{q_3} s_{q_4} - c_{q_5} c_{q_4} s_{q_3}\right) - s_{q_3} s_{q_5} s_{q_6}\right)\right.$$
$$\left. + c_{q_7}\left(c_{q_3} c_{q_4} + c_{q_3} s_{q_3} s_{q_4}\right)\right)$$

$$r_{33} = s_{q_7}\left(c_{q_3} c_{q_4} + c_{q_3} s_{q_3} s_{q_4}\right) - c_{q_7}\left(c_{q_6}\left(c_{q_3} s_{q_4} - c_{q_3} c_{q_4} s_{q_3}\right) - s_{q_3} s_{q_5} s_{q_6}\right)$$

$$r_{34} = q_1 + q_8\left(s_{q_7}\left(c_{q_6}\left(c_{q_3} s_{q_4} - c_{q_5} c_{q_4} s_{q_3}\right) - s_{q_3} s_{q_5} s_{q_6}\right) + c_{q_7}\left(c_{q_3} c_{q_4} + c_{q_3} s_{q_3} s_{q_4}\right)\right) - q_9\left(c_{q_7}\left(c_{q_6}\left(c_{q_3} s_{q_4}\right.\right.\right.$$
$$- c_{q_5} c_{q_4} s_{q_3} - s_{q_3} s_{q_5} s_{q_6} - s_{q_7}\left(c_{q_3} c_{q_4} + c_{q_5} s_{q_3} s_{q_4}\right) + \frac{7 s_{q_3} s_{q_5}}{10} - c_{q_7}\left(c_{q_5}\left(c_{q_3} s_{q_4} - c_{q_3} c_{q_4} s_{q_3}\right) - s_{q_3} s_{q_5} s_{q_5}\right.$$
$$+ s_{q_7}\left(c_{q_3} c_{q_4} + c_{q_3} s_{q_3} s_{q_4}\right) - q_6\left(s_{q_5}\left(c_{q_3} s_{q_4} - c_{q_5} c_{q_4} s_{q_3}\right) + c_{q_5} s_{q_3} s_{q_5}\right)$$

$$r_{41} = 0$$
$$r_{42} = 0$$
$$r_{43} = 0$$
$$r_{41} = 1$$

TABLE 11: Elements of Homogenous Transformation Matrix of the Human Leg

FIG. 36X $$T_G = \begin{bmatrix} x_i & y_i & z_i & p_i \\ x_j & y_j & z_j & p_j \\ x_k & y_k & z_k & p_k \\ 0 & 0 & 0 & 1 \end{bmatrix} \in SO(3) \subset \mathbb{R}^{3x3}$$

FIG. 36Y $$v_b = {}^{M_f} e_{M_t} \quad \text{(Maximum Gap)}$$

$$v_b = {}^{N_f} e_{N_t} \quad \text{(Gap Centre)}$$

$$v_b = {}^{Q_f} e_{Q_t} \quad \text{(Minimum Gap)}$$

SYSTEMS AND METHODS FOR ASSISTING SURGERY

CROSS-REFERENCE TO RELATED APPLICATIONS

The subject application claims priority to Australian Provisional Patent Application No. 2019900476, filed Feb. 14, 2019, the disclosure of which is incorporated herein by reference in its entirety.

TECHNICAL FIELD

The present disclosure relates to systems for assisting surgery.

BACKGROUND

Any references to methods, apparatus or documents of the prior art are not to be taken as constituting any evidence or admission that they formed, or form part of the common general knowledge.

While leg knee and hip joint surgery are common procedures, they require a skilled and experienced surgeon to repair damage to a joint, for example for the knee joint a surgeon operates inside a small space whilst manually moving the patient's leg and steering the surgical instruments, such as the arthroscope, inside the joint through a small incision. Such procedures are challenging, and research shows that a safer environment can be created by providing feedback to the surgeon when moving a patient's limb, or using a robot to perform all or part of the surgery, to adjust the joint. It would be desirable if a system were provided to measure a region of interest (ROI) such as a joint gap reliably. Stereo systems used in other minimally invasive surgeries (MIS) are not suited for knee arthroscopy for example, due to the small size of the arthroscope with only a single lens and the harsh environment inside the knee joint.

Although a few technologies such as deep learning can measure distance inside the body, it is necessary to consider the precision required and thus, the practical use of technology during surgical procedures such as an arthroscopic procedure. A surgeon or robot's (Operator) capability to manoeuvre the surgical instrument or 4 mm wide arthroscope tip through an instrument gap of a few millimeters varies and affects the measurement technology and error tolerance range for safe navigation. For surgeons, factors such as experience, age and fatigue limit their ability to manoeuvre instruments through a gap seen on a 2D image. For robots, the manufacturing quality of links, gearboxes and controls determine how accurate they can steer an end effector such as an arthroscope.

For each surgical situation, the accuracy of the gap measurement needs to be of similar order as the operator capability range. Four million knee arthroscopies are performed annually and demand an increase in safety for patients and surgeons. It would be desirable if a system were provided for measuring the instrument gap with a high level of precision that would be suitable for feedback to a robotic system or a surgeon.

It is an object of the present disclosure to address the above need.

SUMMARY

The present disclosure provides a surgical assist system comprising:

an image capture apparatus for capturing images of a target site, the target site having a region of interest (ROI) with a varying dimension associated therewith;

a sensing system configured to detect one or more conditions associated with one or more of the image capture apparatus, the target site or one or more combinations thereof; and a processing assembly responsive to the image capture apparatus and to the sensing system;

wherein the processing assembly is configured to determine the varying dimension at each of a plurality of times based on images from the image capture apparatus and the conditions detected by the sensing system.

In an embodiment the processing assembly is configured to display values of the varying dimension on an electronic display for reference of a human operator or control of a robotic surgical system.

In an embodiment the processing assembly is configured to operate one or more actuators responsive thereto for physically altering the ROI to bring the varying dimension to a desired value.

In an embodiment the processing assembly is configured to determine a translation of the image capture apparatus from the conditions detected by the sensing system.

In an embodiment the processing assembly is configured to apply a mask to each image for masking around the ROI.

In an embodiment the processing assembly is configured to apply the mask using a sum of squared differences (SSD) procedure.

In an embodiment the processing assembly is configured to segment each image to identify the region of interest (ROI) with the varying dimension associated therewith.

In an embodiment the processing assembly is configured to segment each image by applying an OTSU or deep learning segmentation procedure.

In an embodiment the region of interest comprises a joint gap, instrument gap, knee gap or a gap in the hip. In some instances, 3D surfaces are measured using an optical tracking system or kinematic model.

In an embodiment the processing assembly is configured to determine a distance of the joint gap by applying the translation of the image capture apparatus to a motion stereo procedure.

In an embodiment the processing assembly is configured to apply the translation as a translation vector ($\vec{t}$) to the motion stereo procedure.

In an embodiment the processing assembly is configured to apply points (Go, G1) defining the region of interest (ROI) to the motion stereo procedure.

In an embodiment the motion stereo procedure determines a vector ($\vec{g}$) from the points defining the region of interest, which corresponds to the varying dimension (d).

In an embodiment the processing assembly is configured to determine the varying dimension d in the motion stereo procedure from the translation vector ($\vec{t}$) and from direction vectors ($\vec{a}_n$, $\vec{b}_n$) from the image capture apparatus to the points (Go, G1) defining the ROI at first (Ao) and second (A1) positions of the image capture apparatus along the translation vector.

In an embodiment the processing assembly is configured to approximate an uncertainty in the determination of the varying dimension d.

In an embodiment the processing assembly is configured to approximate the uncertainty by taking into account image errors associated with the segmentation or related image processing steps in analyzing the images.

In an embodiment the processing assembly is configured to approximate the uncertainty by taking into account errors in the sensing system detecting the translation of the image capture apparatus.

In an embodiment the processing assembly is configured to approximate the uncertainty by taking into account errors in the sensing system detecting rotational motion of the image capture apparatus.

In an embodiment the processing assembly is configured to approximate the uncertainty where minimum and maximum extremes of an uncertainty range reflect a minimum desired limit of the varying dimension and a maximum physical limit for the ROI.

In an embodiment the minimum desired limit is a dimension associated with the image capture apparatus.

In an embodiment the minimum desired limit is a minimum joint dimension associated with a tip of the image capture apparatus.

In an embodiment the maximum physical limit is a maximum value beyond which the ROI will lose integrity. For example, where the ROI is a gap of an anatomical joint the maximum physical limit corresponds to the maximum anatomical joint gap.

In an embodiment the sensing system comprises an optical tracking system.

Alternatively, the sensing system may comprise a magnetic tracking system, computer vision-based tracking system or an inertial measurement tracking system.

In an embodiment the sensing system may include one or more markers.

In an embodiment the sensing system includes one or more sensors [cameras] for sensing the markers or for analyzing images for tracking, localization or mapping purposes. In some examples, computer vision may be utilized.

In an embodiment the surgical assistance system may include one or more rigid bodies for supporting the one or more markers.

In an embodiment the one or more rigid bodies include one or more mounting plates.

In an embodiment the surgical assistance system includes one or more base plates for supporting the one or more mounting plates wherein the position of the mounting plates relative to the base plates is adjustable.

In an embodiment the one or more rigid bodies include one or more adaptors for mounting to the image capture apparatus.

In an embodiment the one or more adaptors include a central lumen for fitting about a portion of the image capture apparatus.

In an embodiment the surgical assistance system includes one or more serial or parallel robotic arms.

In an embodiment the one or more robotic arms are responsive to the processing assembly.

In an embodiment the ROI comprises a gap of an anatomical joint. In an embodiment the varying dimension associated with the ROI comprises a width of the gap.

In an embodiment the anatomical joint comprises a knee or hip joint.

In an embodiment the one or more robotic arms are arranged for movement of bones of the knee or hip joint.

In an embodiment the processing assembly is configured to operate the one or more robotic arms for attaining a width of the gap or move the leg to a desired position to advance the surgical procedure.

In an embodiment the processing assembly is configured to operate the one or more robotic arms by applying position data from the sensing system of markers and/or the forward and/or the inverse of a kinematic model of a leg. The kinematic model may be utilized in lieu of an optical tracking system. Alternatively, the kinematic model and optical tracking system may be used at a time. The optical tracking system and the kinematic model can be utilized to track the leg parameters.

In an embodiment the kinematic model of the leg comprises nine degrees of freedom (DOF) model of the knee and hip.

In an embodiment the processing assembly is configured to set some parameters of the kinematic model to zero for operating the one or more robotic arms for a knee arthroscopy procedure.

In an embodiment the processing assembly is configured to operate the one or more robotic arms by applying the position data to a database correlating marker and/or kinematic model positions to bone positions.

The bone and anatomical positions may have been predetermined by means of bone imaging scans such as CT scans.

In an embodiment an origin of a coordinate system used by the processing assembly comprises a femur ball joint center of one of the bones of the joint.

In an embodiment the processing assembly and the robotic arms are arranged for communication via a controller associated with actuators of the robotic arms.

In an embodiment a first of the robotic arms comprises a first holder for holding a lower portion of a leg of a subject associated with the joint.

In an embodiment the first holder is formed as a boot.

In an embodiment the first robotic arm includes a footplate pivotally attached to a remaining portion of the first robotic arm.

In an embodiment a sole of the boot is attachable to the footplate.

In an embodiment a second of the robotic arms comprises a second holder for holding an upper portion of the leg.

In an embodiment the second holder is formed as a cuff or strap for surrounding a portion of a femur.

In an embodiment markers extend from the footplate opposite a side of the footplate for attachment to the first holder.

In an embodiment the processing assembly is configured to operate the second and/or first robotic arm for bringing the bones to a pose corresponding to a desired gap distance for the joint.

In an embodiment the processing assembly is configured to receive the desired gap distance from an operator.

In an embodiment the processing assembly is configured to limit a maximum size of the gap to ensure that it does not exceed an anatomical limit for the joint.

In an embodiment one or more force and/or torque sensors are coupled to the one or more robotic arms for sensing force applied by the one or more robotic arms to the joint to thereby prevent the force exceeding a safe limit.

Also provided is a system for assisting surgery in the form of a surgical joint positioning apparatus for stabilising a subject's joint during a surgical procedure, the apparatus comprising:

a base for being positioned relative to an operating table;

one or more robotic arms coupled or connected to the base for controlling movement of the subject's joint;

one or more motorized actuating arrangements for controlling movement of the robotic arms to allow the joint to be moved in three different planes of motion;

a controller for controlling the motorized actuating arrangements, the controller being coupled to a processing assembly, the processing assembly adapted to receive and process signals received from one or more sensors sensing one or more respective physiological parameters of the subject during surgery;

wherein during use the controller controls movement of the one or more robotic arms based on the physiological parameters sensed by the one or more sensors.

In an embodiment a first of the robotic arms comprises a first holder for holding a lower portion of the subject's leg; and a second of the robotic arms comprises a second holder for holding an upper portion of the subject's leg.

In an embodiment the second robotic arm is configured to provide the second holder at least two degrees of freedom and the first robotic arm is configured to provide the first holder at least four degrees of freedom.

In an embodiment the one or more sensors includes an arthroscope providing information related to internal joint geometry of the subject.

In an embodiment the processing assembly is configured to receive and process signals from the arthroscope to compute a gap created within the joint during surgery and control movement of the first and second robotic arms based on the computed value of the gap.

In an embodiment the processing assembly is configured to process signals from inside the joint to compute the instrument gap inside the joint.

In an embodiment the one or more sensors includes detection or tracking devices configured to track markers positioned on the subject in response to movement of the one or more robotics arms during use.

In an embodiment one or more force and torque sensors are used to ensure safe manipulation of the subject's limb.

In an embodiment the sensors comprise one or more medical or robotic devices arranged for viewing, monitoring and/or tracking features and movements of the subject's joint whereby feedback from the sensors is received by the processing assembly and processed to further control the motorized actuating arrangement of the robotic arms.

In an embodiment the surgical joint positioning apparatus further comprises a user input interface such as a human-machine-interface (HMI) for receiving user input from an operator, the processing assembly being responsive to the user input interface wherein the processing assembly is arranged to receive the user input and process the user input and the signals received from one or more sensors in accordance with one or more pre-determined or operator determined rules.

In an embodiment the input interface is arranged to receive user input including one or more of the following:

(a) physiological and anatomical parameters of the subject;

(b) three-dimensional model of the subject's joint;

(c) surgical procedural details; and (c) information related to the one or more sensors.

The present disclosure also provides a method for robotic manipulation of one or more limbs of a subject for assisting a surgeon to deliver a surgical procedure to the subject, comprising:

holding the one or more limbs with respective controllable robotic arms;

operating a processing assembly having control of said limbs to receive one or more parameters defining a desired pose for the limbs;

operating the processing assembly to apply the one or more parameters to an inverse kinematic model encompassing the limbs to determine position for at least one of the limbs; and operating the processing assembly to apply the position to a forward kinematic model encompassing the controllable robotic arms and control said robotic arms based on an output from the forward kinematic model to thereby bring the one or more limbs to the desired pose.

The present disclosure also provides a surgical assist method comprising:

capturing at a sequence of times, electronic images ("the captured electronic images") of a target site, the target site having a region of interest (ROI) with a varying dimension associated therewith;

electronically sensing positions ("the sensed positions") from which the electronic images are captured;

applying two or more of the captured electronic images and the sensed positions from which said images are captured to a processing assembly; and operating the processing assembly implement a stereo motion procedure in respect of points of the ROI from the captured electronic images the detected positions of the captured electronic images to thereby determine the varying dimension at each of a plurality of times for presentation to the surgeon.

The present disclosure also provides a surgical assist system comprising:

an optical tracking system including a number of markers for acquiring position of one or more of an arthroscope, robotic arms, limbs of a subject;

a processing assembly responsive to the optical tracking system and to video from the arthroscope; and a robotic joint positioning assembly under control of the processing assembly; wherein the processing assembly controls the robotic joint positioning assembly with reference to the optical tracking system and one or more kinematic models of the leg and/or the robotic joint positioning assembly.

BRIEF DESCRIPTION OF THE DRAWINGS

FIG. 28*aa* is a view of the human knee.

FIGS. 35A-Z illustrate mathematical equations, formulae, expressions or parameters employed by the techniques described herein.

FIGS. 36A-Y illustrate mathematical equations, formulae, expressions, parameters, and tables employed by the techniques described herein.

It will be appreciated that one or more of the embodiments depicted throughout the drawings may have certain components, structural features, and/or assemblies removed, depicted schematically, and/or shown in phantom for illustrative purposes.

DETAILED DESCRIPTION

Before turning to the figures, which illustrate the exemplary embodiments in detail, it should be understood that the present application is not limited to the details or methodology set forth in the description or illustrated in the figures which relates to one or more embodiments only. It should also be understood that the terminology set forth in the detailed description should not be regarded as limiting by the person skilled in the art.

The surgical assist system, which in one embodiment is in the form of or includes a joint positioning apparatus (or as it is sometimes referred to a "medical robot") comprising motorized actuators described herein can be used in any context to position a joint. For example, surgeons or robotic systems may use the joint positioning apparatus prior to or during a surgical procedure. Other medical professionals may use the motorized joint positioner during examination, testing, rehabilitation or imaging of the joint. The motorized joint positioner can also be used to position a variety of different joints, such as a knee, hip, ankle, elbow, shoulder or wrist.

Figure 1:
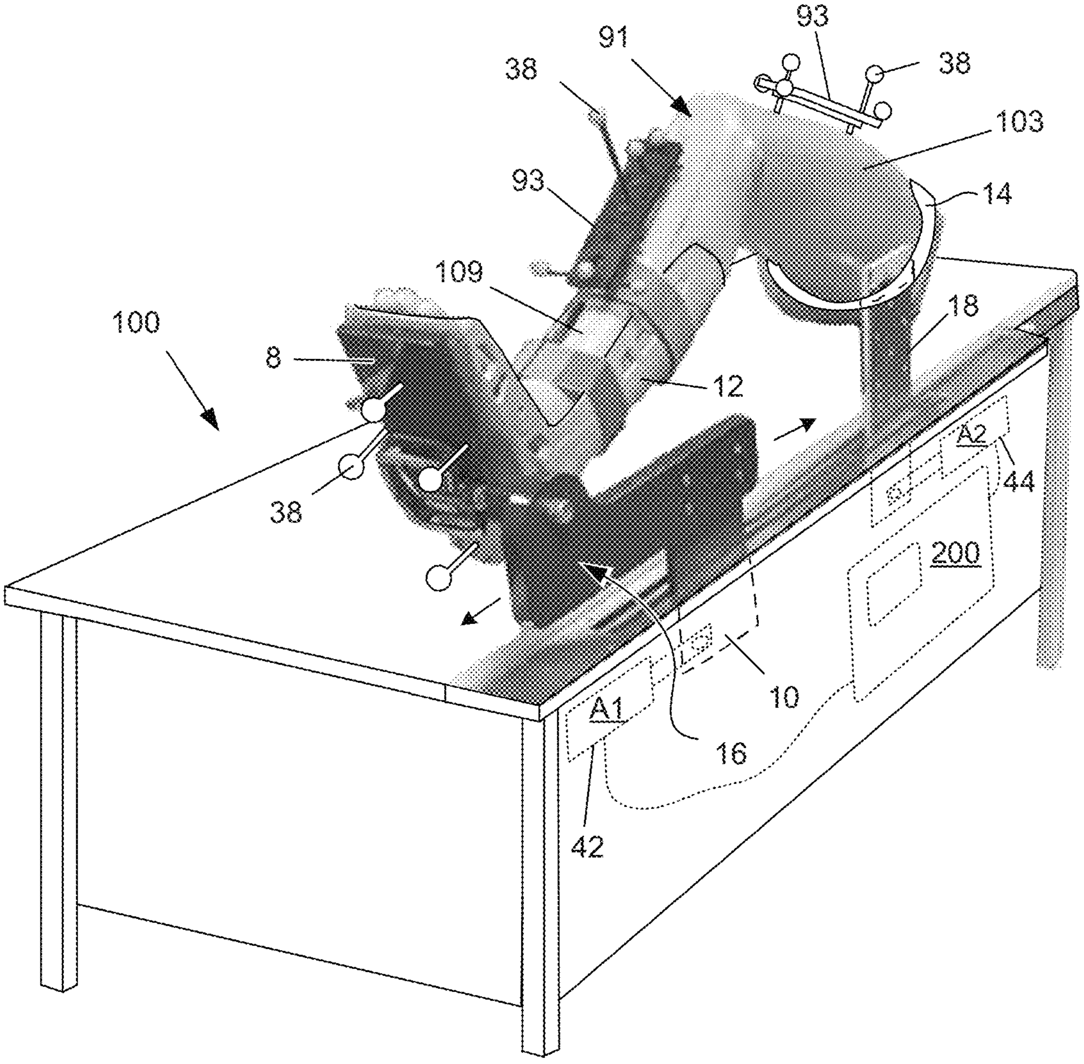
FIG. 1 shows a surgical joint positioning apparatus being a portion of a surgical assist system.
Figure 2:
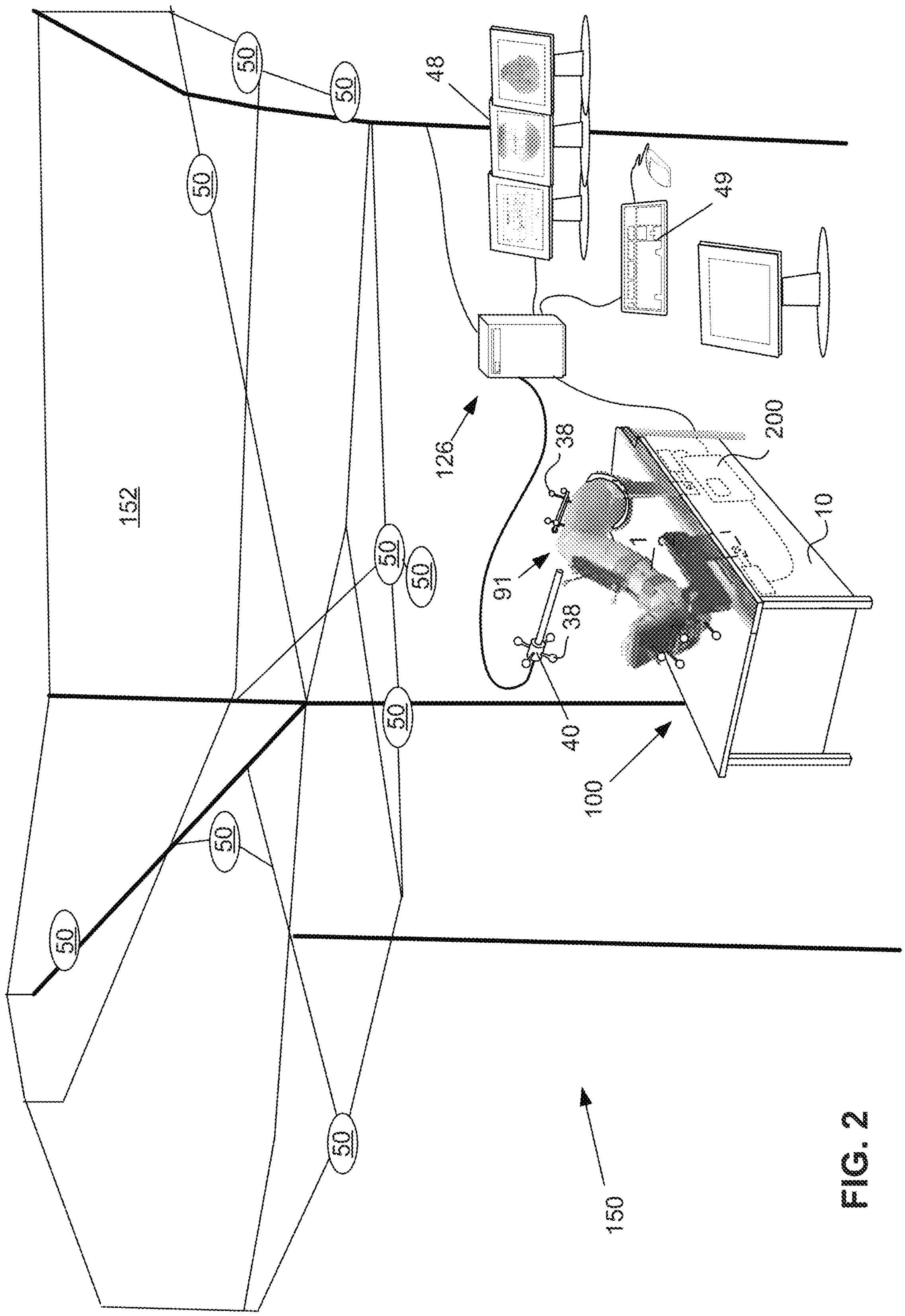
FIG. 2 depicts a surgical assist system including the surgical joint positioning system a processing assembly with a human-machine-interface and a sensing system.

Referring to FIGS. 1 and 2, a surgical joint positioning apparatus 100 according to an exemplary embodiment includes a first holder, in the form of boot 12 for placement about the tibia and a second holder 14 which may be in the form of a thigh cuff or strap about the femur. Other holders may be used for other joints, e.g. ankle or hip joints as necessary. The boot 12 is coupled to a robotic arm 16. The robotic arm 16 includes a pivoting footplate 8 that is pivotally coupled to sliding portion 10 of the robotic arm 16. The pivoting footplate 8 attaches to an underside or sole portion of the boot 12. The second holder 14 is coupled to a second robotic arm 18. The robotic arms 16, 18 may be driven by motorized actuators A1 (42) and A2 (44), such as linear or rotational actuators. One type of actuator which may be used includes series elastic actuators (SEAs). In the figures, provided herein the motorized joint positioning apparatus 100 is illustrated during positioning of a knee joint of leg 91. However, as previously described, embodiments may be utilized for stabilising other joints of the human or indeed many types of non-human animals. The SEAs may be configured to enable force-control and high-precision position control of the robotic arms 16 and 18 and the SEAs may be linked to provide position control in numerous degrees of freedom. In the presently described embodiment, the first robotic arm 16 may comprise six or more degrees-of-freedom (DOF) and the second robotic arm 18 comprises one or more DOF. Each robotic arm 16 and 18 may be provided with numerous joints and could be controlled by actuators such as SEAs or a series of stepper motors corresponding to each joint. Accordingly, numerous joints (and corresponding actuators to control the joints) as desired may be linked to form the robotic arms with the desired degrees of freedom. In that regard FIG. 28 illustrates a robotic arm that the Inventors have modelled after the human leg which will be discussed later.

The first and second holders 12, 14 can be any suitable structure for holding a portion of a patient. In the embodiment shown in FIG. 1, the holders 12, 14 are a boot and a cuff or strap. The patient's upper leg (e.g., thigh) is restricted by holder 14, and the patient's lower leg (e.g., ankle) rests in holder 12. The holders 12, 14 may further include one or more straps for securing the patient to the holders 12, 14.

FIG. 2 shows a diagram of a surgical assist system 150 incorporating the joint positioning apparatus 100. The joint positioning apparatus 100 may be used in connection with one or more controllers 200 which may be mounted in the housing or base 10 of the joint positioning apparatus 100. The one or more controllers 200 may control the actuators 42, 44 (e.g. SEAs) that move the robotic arms 16 and 18 and may be operated in communication with a processing assembly or "processing circuit" (represented in the figures as a computer 126). The processing assembly 126 may also be provided in the form of an onboard processor integrated into the controller 200 of the joint positioning apparatus 100. Accordingly, in some embodiments the processing assembly 126 incorporates the controller 200. Throughout this disclosure, the terms one or more controllers can be interchangeable with processing assembly or processing circuit.

The processing assembly 126 is configured, by instructions comprising a software product that it executes, to receive and process signals from one or more sensors or sensing devices such as an image capture apparatus in the form of a knee arthroscope 40 and/or one or more cameras 50 that, in conjunction with position markers 38, comprise a sensing system 152.

As will be explained in the foregoing sections, the knee arthroscope 40 and the cameras 50 can sense conditions associated with the image capture apparatus and the target site, e.g. the knee joint, including a plurality of physiological parameters of a patient undergoing a surgical procedure (such as but not limited to a knee replacement surgery). In particular, the conditions include physiological parameters such as the positions of each of the markers and thus the positions of bones to which the markers are attached. As will be discussed in more detail shortly, the processing assembly 126 is configured to receive and process the signals related to these physiological parameters and in response provide outputs such as a display indicating joint gap distance and/or control signals to the controller 200 to control movement of the one or more robotic arms 16 and 18 based on the physiological parameters sensed by the knee arthroscope 40 and sensing assembly 152.

In some embodiments the sensing system 152 does not include markers that are attached to bones but rather, as will be discussed, the processing assembly 126 refers to forward and/or inverse kinematic models that it accesses.

Arthroscopes such as the knee arthroscope 40 are currently used by surgeons during arthroscopic surgery to provide real-time information about the internal knee geometry of the patient, via a video feed from a camera, that is coupled by fibre optic to a leading tip of the arthroscope from whence the sequence of images comprising the video are captured. When a surgical procedure on the knee is carried out by a surgeon, the leg angle and position of the upper (femur) and lower (tibia) portions of the leg often need to be changed as a result of which different parts of the inner knee are exposed. Such arthroscopes use the same path to provide light into the knee joint as the cameras viewing direction to record video of the inner knee.

Figure 3:
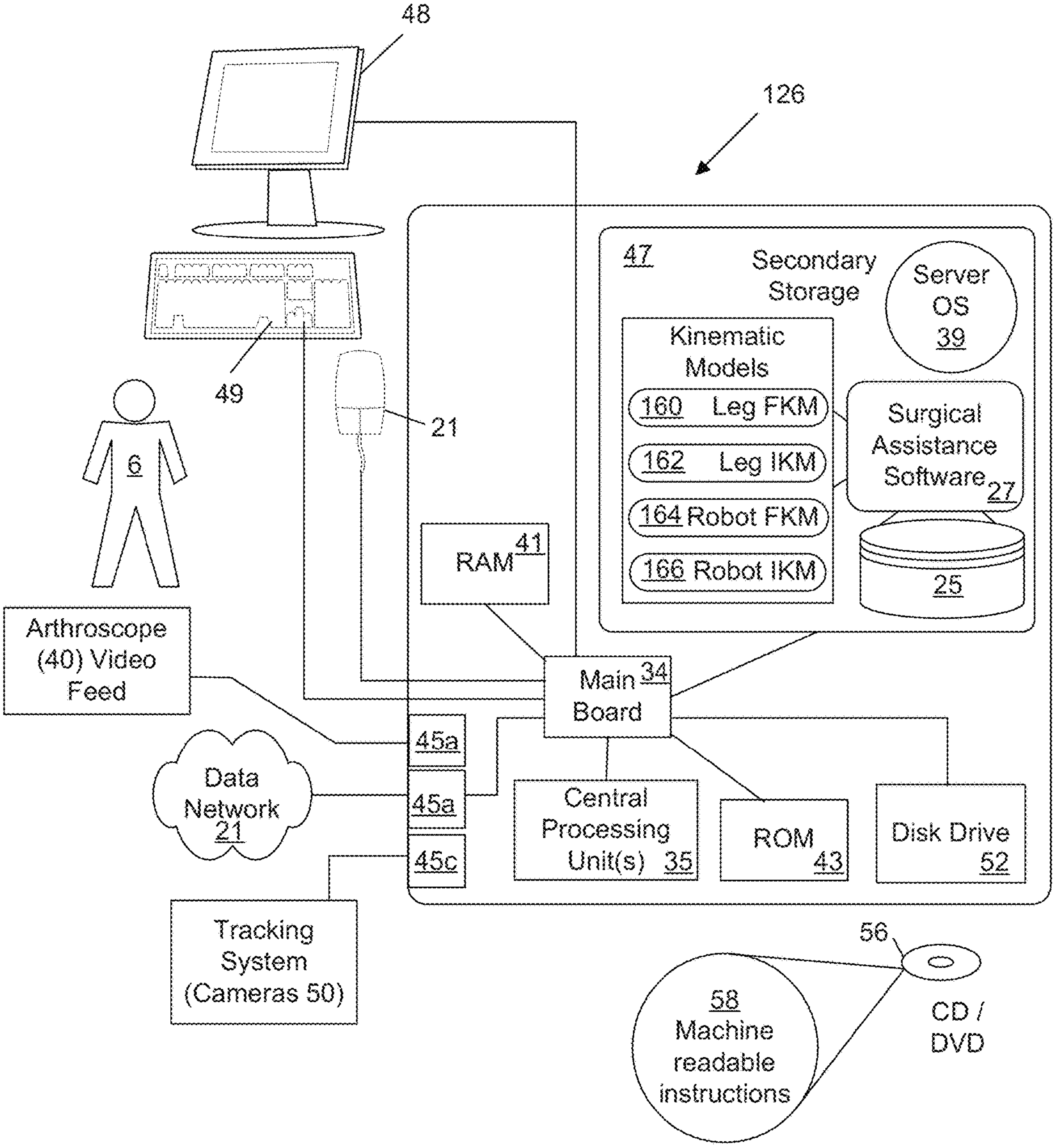
FIG. 3 is a block diagram of the processing assembly.

FIG. 3 comprises a block diagram of the processing assembly 126 which is programmed with surgical assistance software product 27 to thereby configure the processing assembly 126 to undertake its various tasks as described herein. Processing assembly 126 includes secondary storage 47, which is implemented by a magnetic or solid state data drive and which stores an operating system, for example Microsoft Windows, Ubuntu Linux and Apple OS are examples of such an operating system.

The processing assembly 126 includes a main board 34 which includes circuitry for powering and interfacing to at least one onboard central processing unit or "processor" or "microprocessor" 35. The at least one onboard processor 35 may comprise two or more discrete processors or processors with multiple processing cores.

The main board 34 also communicates with random access memory (RAM) 41 and read only memory (ROM) 43. The ROM 43 stores instructions for a Basic Input Output System (BIOS) or UEFI which the CPUs 35 access upon start up and which prepares the CPUs 35 for loading of the operating system 39 from secondary memory 47.

The main board 34 will include one or more communications ports, 45*a*,-45*c*. For example, port 45*a* may be a high-speed data port for receiving video signals from arthroscope 40. Port 45*c* may be configured for receiving signals from marker tracking cameras 50 of sensing system 152, whereas port 45*a* may be a LAN adaptor that places the processing assembly 126 in data communication with a computer network such as the Internet 21 via a router or other suitable network interface device.

The processing assembly 126 includes a human-to-machine interface (HMI) in the form of keyboard 49, mouse 21 and display 48 which enables operator 6 to directly enter commands, read output, and generally interact with the processing assembly 126 as the CPUs 35 execute various operating system and application software instructions.

The secondary storage 47 also establishes a data storage arrangement, such as a database 25 that is implemented by the surgical assistance software 27. As will be explained in some embodiments the database 25 stores records correlating marker positions with joint angles. During operation of the processing assembly 126 the CPUs 35 load the operating system 39 and then load the surgical assistance software 27. In other embodiments the database 25 may be stored at a remote location and accessed by data communications via port 45*a*.

The surgical assistance software 27 may be provided as tangible, non-transitory machine-readable instructions 58 on a media such as a magnetic or optical disk 56 for reading by disk drive 52.

In some embodiments the sensing system 152 includes markers 38 that are attached to bones ("bone markers") of a subject in order that the sensing system 152 is able to track the position of the bone markers and thus the bones. However in other embodiments the surgical assistance software 27 interfaces with kinematic models (and corresponding inverse kinematic models) of the leg and robot 100 (i.e. joint positioning apparatus 100) in order to determine the position or "pose" of the legs and also to acquire a desire pose. Consequently, secondary storage 47 stores leg forward kinematic model 160, leg inverse kinematic model 162, robot forward kinematic model 164 and robot reverse kinematic model 166. In a subsequent section of this specification the development of a forward kinematic model will be described in detail. Once the forward kinematic model is known there are techniques that can be used for approximating an inverse kinematic model, for example one technique is the Jacobian inverse technique. An analytic solution to provide an inverse kinematics model may also be used or alternatively software tools such as IKFast exist for analytically solving robot inverse kinematics equations.

It will be realized that the exemplary processing assembly 126 that is illustrated in FIG. 3 comprises a discrete hardware machine that is suitably programmed. In other embodiments the server may be implemented by a virtual machine, e.g. a "cloud server" that uses shared hardware resources of a "server farm" as required.

Figure 4:
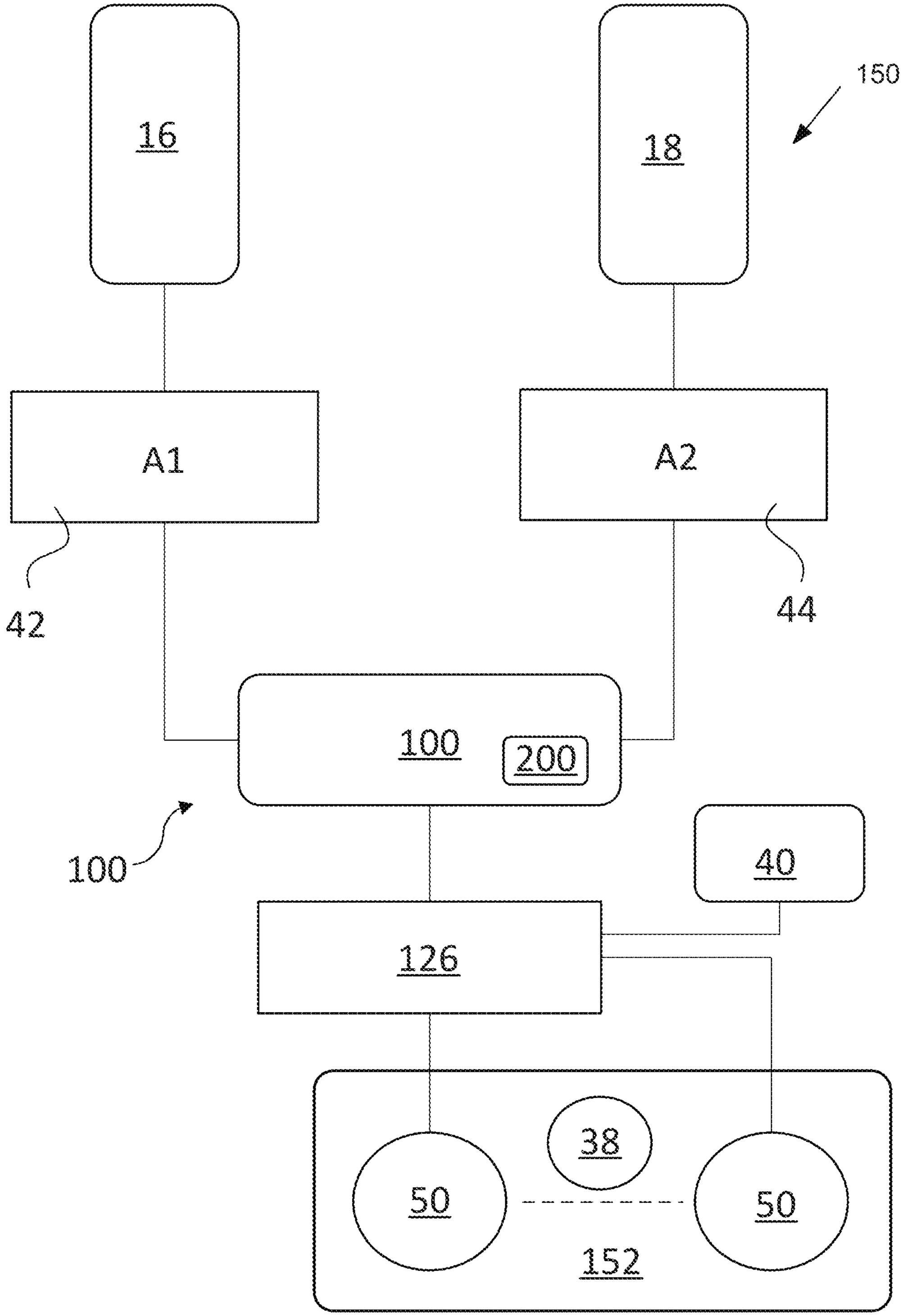
FIG. 4 is a high-level diagram of a surgical assist system.

FIG. 4 is a high-level block diagram of an embodiment of a surgical assist system 150 according to an embodiment.

Figure 5:
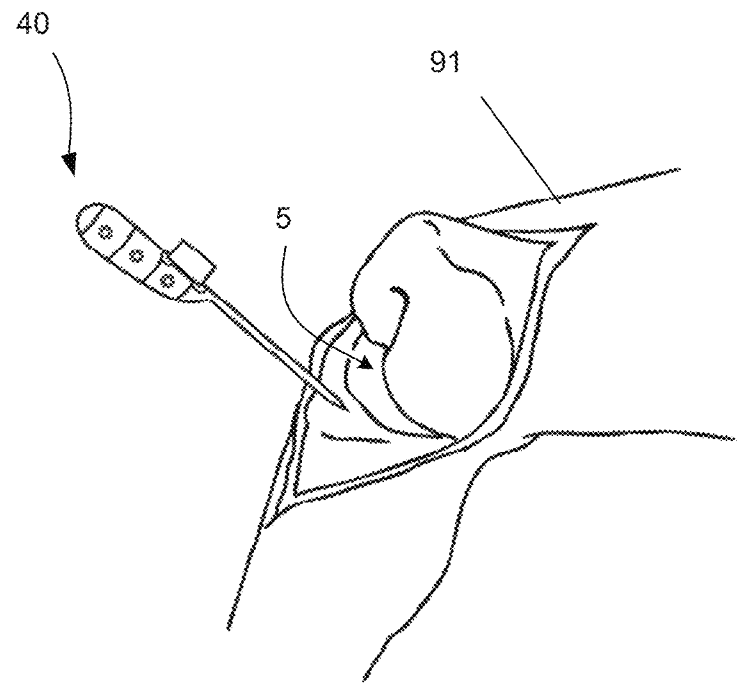
FIG. 5 depicts an arthroscope during an arthroscopy of a knee joint.

With reference to FIG. 5, during arthroscopic surgery, a region of interest (ROI), such as gap 5 is created within the knee joint by changing an angle of the knee joint, which allows access to surgical tools and a visual inspection of the area. The size of this gap is a varying dimension associated with the ROI that may range from zero (e.g. when the patient is standing) to a few millimeters as the leg is flexed. A region inside the knee, which may be referred to herein as the 'instrument gap', as viewed through the arthroscope 40, is the space between the main structures inside the knee, through which surgical instruments can be moved. The instrument gap 5 can form between the femur and tibia, patella and femur or other features that are observed through the arthroscope (3.9 mm in diameter). As will be discussed, in an embodiment, upon insertion of the knee arthroscope 40, a dimension of the instrument gap may be computed by the processing assembly 126 and presented on display 48 for and/or, in some embodiments, compute one or more control signals that may be generated to autonomously control the robotic arms 16 and 18 to further impart motion to the patient's leg for maintaining or increasing the instrument gap 5.

A user input interface such as the keyboard 49 which may be operated by the surgeon or an instrument operator to receive specific user input (such as physiological parameters of the patient, three dimensional model of the patient's knee joint, information related to the knee arthroscope 40 or the cameras 50) which may be used by the processing assembly 126 to determine the manner in which it processes feedback received from the knee arthroscope 40 or the cameras 50 of the sensing system 152 and generate controlling signals to control the motorized movement of the robotic arms 16 and 18 or alternatively a display on monitor 48 of information such as a width of the instrument gap 5 for the surgeon's reference. It will be understood that the constant movement of the knee arthroscope 40 by a surgeon results in the instrument gap 5 varying constantly. To compensate, the leg motion changes the gap to ensure the gap in front of the arthroscope is large enough. A set of rules, comprising the surgical assistance software 27, may be programmed into the processing assembly 126 (by way of using non-volatile secondary memory 47) to maintain a desired instrument gap 5 in the patient's knee by imparting movement to the robotic arms 16 and 18 when necessary, for example when the instrument gap 5 falls below a certain pre-determined dimension, associated with a surgical instrument intended to be inserted into the gap. In some embodiments the processing assembly 126 may be pre-programmed with one or more of many different rules and/or algorithms comprising surgical assistance software 27 to impart autonomous or semi-autonomous control of the robotic arms 16 and 18 during surgery without requiring any physical effort on the part of the surgeon in manipulating the joint of the patient.

As discussed, surgical assist system 150 includes a tracking system in the form of sensing system 152 to track a portion of a patient's anatomy (e.g., the portion held by the joint positioning apparatus 100). The tracking system 152 may be optical or mechanical. As previously discussed with reference to FIG. 2, the tracking system may be an optical tracking system that includes detection devices or sensors in the form of cameras 50 and trackable markers 38 fixed to items to be tracked such as the portion of the patient's anatomy (e.g., the patient's bones) held by the joint positioning apparatus 100 and also the arthroscope 40. The trackable markers are detectable by the detection devices/cameras 50. The trackable markers 38 are affixed to the tracked objects (e.g., the patient's bones or parts of the manipulator and/or the arthroscope), in a secure and stable manner. As will be discussed in more detail later, specific rigid bodies may be used for attachment of the markers to anatomy and to the arthroscope. In one embodiment, the trackable markers 38 may be fixed to the patient's bones with bone pins. In operation, the cameras 50 detect positions of the trackable markers 38, and the pose of the tracked object (e.g., the orientation of the patient's bones) can be calculated based on the trackable markers' positions. The surgical assist software 27 may include instructions for configuring the processing assembly 126 to receive and process tracking related information from the trackable markers 38 and compute one or more control signals to autonomously control the movement of the robotic arms 16 and 18 to further impart motion to the patient's leg to maintain or position the patient in a desirable position to assist the surgeon during a surgical procedure.

Figure 6:
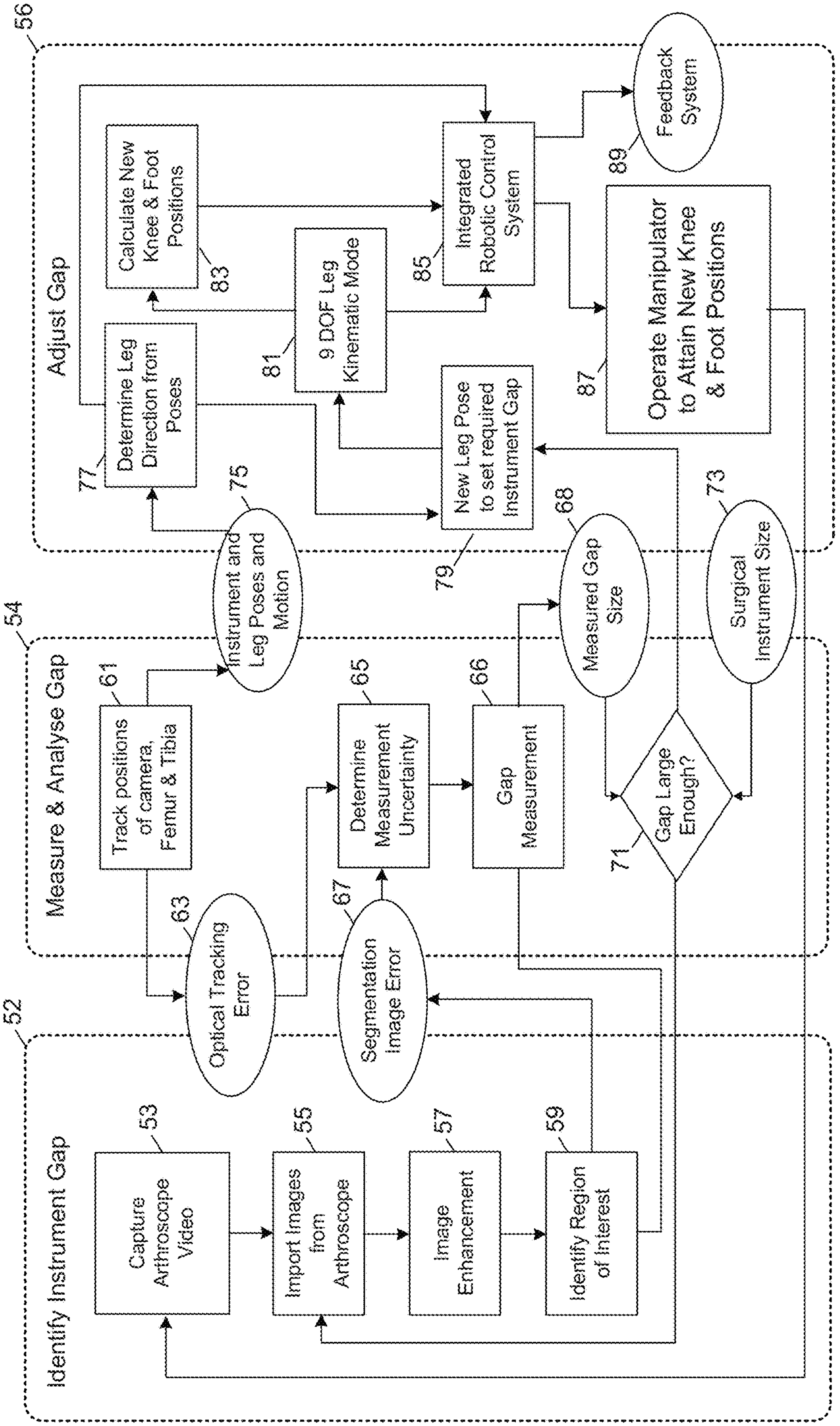
FIG. 6 is a flowchart depicting an exemplary set of steps implemented as instructions of a software product that configures the processing assembly.

FIG. 6 is a flowchart of a method of operation that is coded as machine readable instructions of surgical assistance software 47 for processing assembly 126 to execute according to an embodiment. The software comprises three main functional blocks being a first block 52 for identifying an instrument gap of a joint, which in the present exemplary embodiment is the knee joint. The second block 54 is primarily concerned with measuring the instrument gap taking into account optical tracking error and image segmentation error. The third block 56 involves operating motorized actuators such as actuators 42 and 44 comprising a joint manipulator to move the first holder 12 and the second holder 14 in order to attain new knee and foot positions and thus an adjusted instrument gap.

The various boxes making up each the blocks are as follows:

a. Arthroscope capture Image (box 53)
b. Images are captured into a computer in real-time (box 55)

Image Enhancement
a. Arthroscopy Images at computer are processed (box 57):
   i. Changed into greyscale
   ii. Histogram levelling
   iii.
b. Field of View center image Identify Region of Interest (ROI) (box 59)
a. Segment Image—instrument gap Track Camera and Leg (box 61)
a. Setup Optical tracking volume
b. Mount Rigid Bodies on femur and tibia
c. Mount camera to continuously track markers
d. Record reference video synced with marker tracking data Determine Measurement Uncertainty (box 65)
a. Errors from segmentation (box 67)
   iv. Average of ROI
   v. Around direction of scope motion
b. Optical tracking errors (box 63)
   vi. Translation
   vii. Rotation Instrument Gap Measurement (boxes 66, 68)
a. Motion Stereo measurement
b. Deep Learning measurement
c. display measured gap size on monitor 48.

Check that Instrument Gap is sufficiently large (box 71) compared to current Surgical Instrument Size (box 73)

New leg pose (box 79)
a. Determine new leg pose to set gap to desired size
b. Angles and translation similar to the decision a surgeon makes 9 DOF Kinematic Model
a. 3 DOF hip model
b. 6 DOF knee model
   i. 3 rotations
   ii. 3 translation Knee and Foot position (box 83)
a. From kinematic model calculate foot position
b. New foot position is the same as where robot needs to move to
c. Robot inverse kinematics provide motor rotations to get to foot position Leg Move Direction (box 77) using instrument and leg poses and motion data (box 75).
a. Depending of the arthroscope position the leg move direction change to change gap
b. Inner knee database around rotational axis
c. Determine in which quadrant the camera is
d. Use inner knee positional database to determine move direction to increase or decrease gap Robot Control (box 85)
a. Inputs:
   i. Kinematic model (box 81)—tell robot how to move the leg to prevent injury and to position the foot and knee in the desired position to set the gap as required
   ii. Foot and knee position (box 83): xyz position for the knee (condyle center) and foot (bottom center of tibia at AJC)
   iii. Leg move direction (box 77)
b. Calculate inverse kinematics of robot using foot and knee position
c. Move robot (leg manipulator) arm (box 87)
d. Image change—check new image and position to determine gap size (box 68)
e. Feedback signals Feedback System (box 89)
a. Output to surgeons or robotic systems:
   i. Haptic feedback—e.g. use of tactile alerts and/or vibratory mechanisms.
   ii. Screen updates
   iii. Robot control
   iv. Instructions to staff Boxes 53-59—Capture Arthroscope Video Initially, at box 53 the processing assembly 126 establishes communication with the arthroscope via communications port 45*a*. At box 55 the processing assembly imports captured images from the arthroscope as a series of frames of video which are stored in secondary storage 47 in an image storage format file. At box 57 image enhancement is performed. Initially the processing assembly 126 applies a masking procedure because subtracting the background (square frame around the arthroscope image) from the arthroscope image is highly preferred for accurate image analysis. Tachibana et al. compared the sum of squared differences (SSD), the sum of absolute differences (SAD) and normaliszed cross-correlation (NCC) for template matching. It was found that for greyscale images SDD and SAD performed better than NCC [Tachibana et al., 2012] H Tachibana, Y Uchida, and H Shiizuka. "Determination of the optimized image processing and template matching techniques for a patient intrafraction motion monitoring system". *Medical Physics,* 39(2):755-764, 2012.

Figure 7:
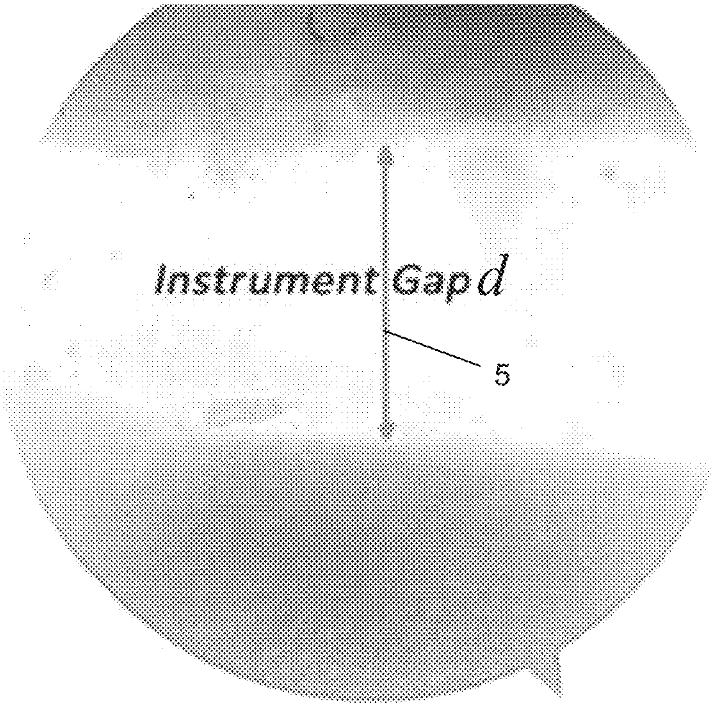
FIG. 7 is a color inverted arthroscopic image of a gap of a knee joint or "instrument gap.

As previously discussed, during arthroscopic surgery, a gap is created within the knee joint as illustrated in FIG. 7. Detecting the instrument gap is very advantageous because gauging the instrument gap and displaying it on display 48 provides the surgeon with information as to whether or not a surgical instrument will fit through the gap without damaging its cartilage. Being able to determine the size of the instrument gap is also needed in the preferred embodiment wherein the automation and control of the leg movement by the robotic arms 16 and 18 is implemented.

One or more of the Inventors have previously analysed the performance of three different segmentation procedures in the paper: Strydom, Mario, Jaiprakash, Anjali, Crawford, Ross, Peynot, Thierry, & Roberts, Jonathan (2016) *Towards robotic arthroscopy: 'Instrument gap' segmentation*" In Pounds, P & Kurniawati, H (Eds.) Proceedings of the 2016 Australasian Conference on Robotics and Automation: Australian Robotics and Automation Association, Australia, pp. 1-10 the contents of which is hereby incorporated in its entirety by reference.

Figure 12:
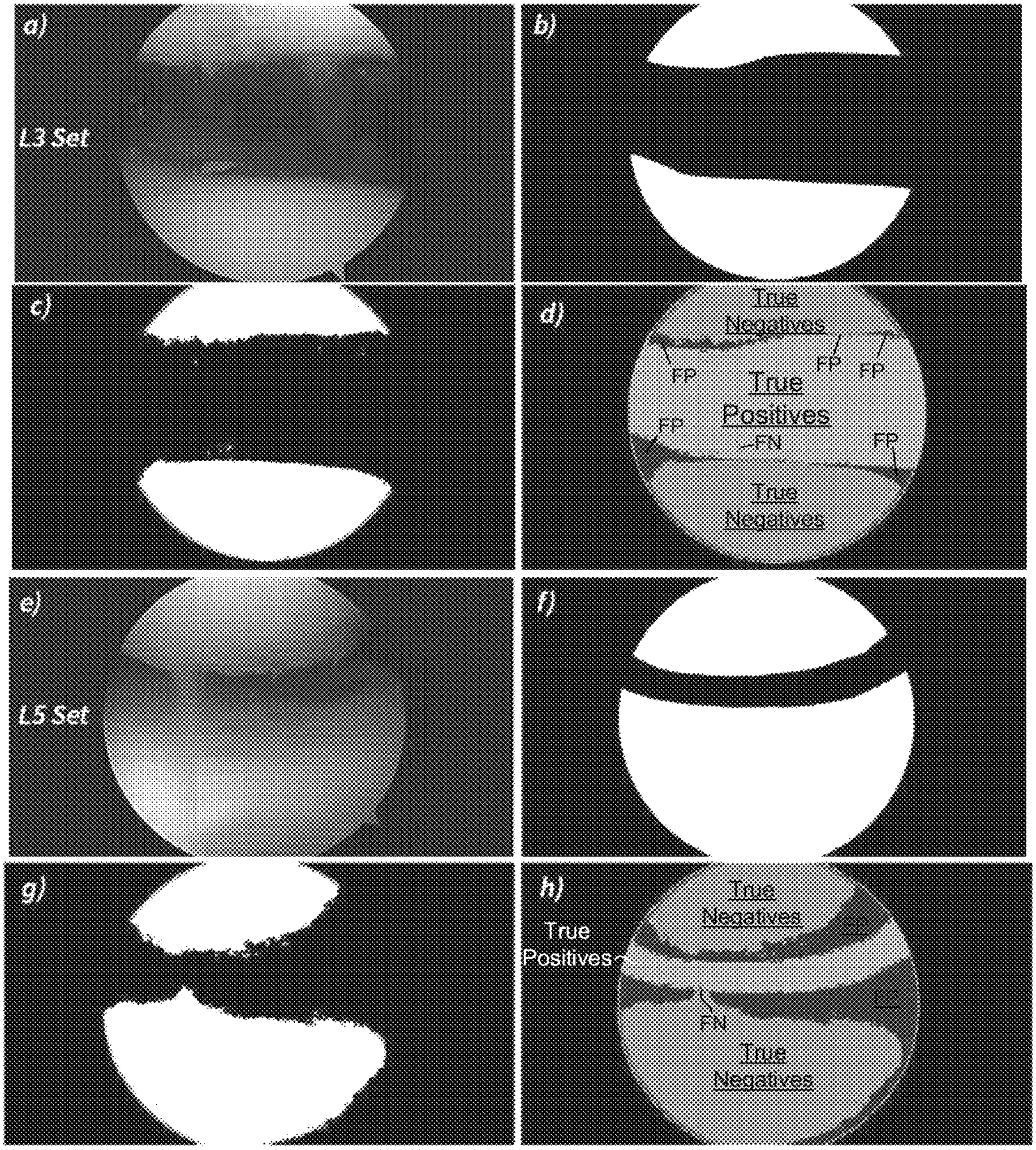
FIG. 12 shows a number of segmentation and image errors of the instrument gap for two areas inside the knee joint using the OTSU algorithm: (a,e)—arthroscope image unsegmented; (b,f) images marked up by human expert; (c,g) OTSU Mask; (d,h) SAD output with image errors false positives (FP) and false negatives (FN).

In that paper it is explained that cadaver experiments were performed in which, arthroscopy videos were recorded to capture a sequence of images. These sequences were used to create ten sets of one hundred images to test the segmentation algorithms against. Image sets were manually marked-up by an expert surgeon as a quasi-ground truth. Segmentation is the procedure by which an image and in particular a ROI of an image is processed so that the instrument gap can be distinguished from anatomical structures on either side. FIG. 12, which will be discussed in more detail later, illustrates the results of different segmentation algorithms on arthroscope images.

Three segmentation algorithms were examined and implemented to test their suitability to segment the instrument gap. It was found that the Chan and Vese Level Set Active Contour algorithm (Chan and Vese, 2001] T F Chan and L A Vese. Active contours without edges. *IEEE Transactions on Image Processing,* 10(2):266-277, 2001) is easy to initialise, has a high average accuracy level and is robust across all image sets. Using its a priori shape capability the level set active contour can be a great option for segmenting the instrument gap if its performance can be optimized. The Watershed algorithm ([MathWorks, 2016a] MathWorks. *Marker-Controlled Watershed Segmentation,* 2016) performed sporadically well across the image sets, and needs to be tuned for each set to work well. It is not suited to be used for segmenting the instrument gap. The OTSU adaptive thresholding algorithm ([Otsu, 1979] N Otsu. A Threshold Selection Method from Gray-Level Histograms. *IEEE Transactions on Systems, Man, and Cybernetics,* 9(1):62-66, 1979 (the disclosure of which is hereby incorporated in its entirety by reference)) was preferred because it was found to perform fast and accurately across the image range, and low resolution images can be used to improve the processing speed if required. Overall the OTSU algorithm was found to outperform the watershed and level set algorithms in segmenting the instrument gap.

Accordingly, surgical assistance software 27 includes instructions for processing assembly 126 to apply the OTSU procedure for segmenting the gap and thus identifying the region of interest (ROI) at box 59.

Segmentation Image Error (Box 67)

In Minimal Invasive Surgery (MIS) applications only single-lens cameras (motion) is currently available for arthroscopy. It is a significant challenge to use a standard motion arthroscope camera to measure the instrument gap or hip joint.

The knee joint has many diagnostic points (e.g., fifteen) used during arthroscopy, and each of these points has different features, colour and lighting, resulting in a specific image error for that area. From cadaver data sets, one thousand frames were segmented and manually marked-up by an expert surgeon as a ground truth. Comparing segmentation results with the arthroscope image ground truths, the root mean square (RMS) segmentation image errors can be calculated in pixels.

Figure 8:
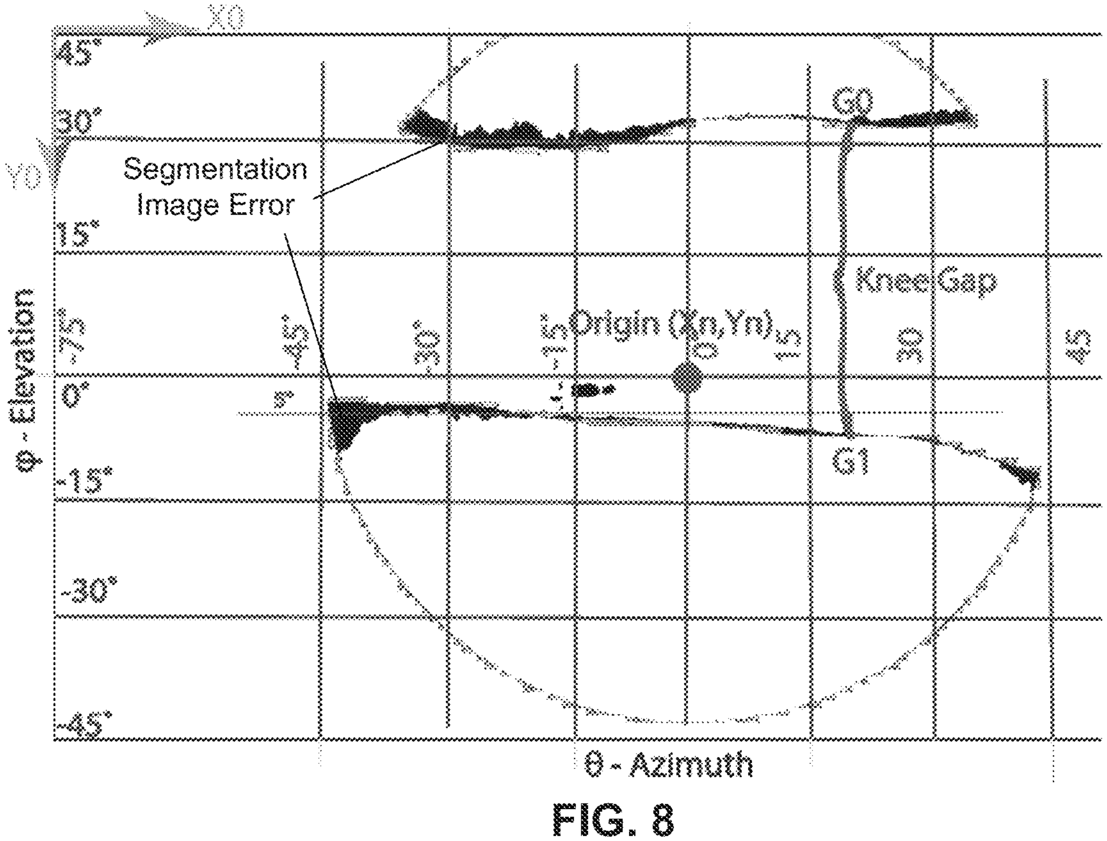
FIG. 8 is a graph of the angular error for imaging within the knee gap with an arthroscope having an azimuth angle of 90 degrees and an elevation angle of 90 degrees. Due to a 30-degree offset angle of a tip of the arthroscope the direction of the movement (where the gap is), is not in the image center. Image errors from segmentation are indicated adjacent the image knee gap.

FIG. 8 is a graph illustrating how the errors can be measured from the images and the angular image error calculated for the Stryker Arthroscope. The Stryker Arthroscope is available from https://www.stryker.com/us/en/endoscopy/products/ideal-eyes-hd-autocalvable-eyepiece-arthroscopes.html.

The Stryker arthroscope uses the same optical path to provide light into the knee joint and to record video of the inner knee. It has a field of view (FOV) of 90° at an angle of 30° at the tip. The video frame rate for the arthroscope camera is 60 frames per second, with a full resolution of 1280×720 pixels for each frame.

The degrees per pixel (DPP) in each direction are calculated with the equations shown in FIG. 35A, with the total image error a combination of DPPx and DPPy. The surgical assistance software 27 contains instructions that configure the processing assembly 126 to calculate the segmentation image error (box 67) using the above equations.

Track Positions of Arthroscope Camera, Femur and Tibia (Box 61)

Arthroscope motion is required to triangulate and calculate the instrument gap size and so the measurement accuracy of the motion from one frame to another has a direct impact on computing the instrument gap.

The Inventors have previously used an optical tracking system 152 during cadaver and laboratory tests to measure leg movement and arthroscope translation and rotation. One such system is the OptiTrack system. In those tests high-resolution cameras were used to reliably monitor ten OptiTrack markers (https://optitrack.com/products/motion-capture-markers/) placed on the arthroscope rigid body and on the cadaver leg. The motion capture system was run at up to 120 frames per second (fps), with a resolution of 1280×1024 pixels for each of the 1.3 megapixels flex 13 cameras. The system can provide the precision of less than one millimeter when used in a set environment.

Whilst a preferred form of the sensing system 152 is optical tracking, there are many options for measuring the translation, such as using magnetic sensors or high-quality inertial measurement unit systems, all with different error metrics. If improperly set up, the OptiTrack Motive system can significantly skew the sub-ten milli-meter range of the instrument gap. For these type of systems, the number of cameras and calibration of the system largely define the accuracy and precision. To study the optical tracking error the Inventors used ten cameras to ensure robust coverage and precise tracking of the markers between frames during the surgery. To determine the OptiTrack system precision, stationary and moving markers were analysed during cadaver experiments and each of the root mean square (RMS) errors calculated for five sets of over six thousand measurements. The error vector lengths from these measurements provide accurate metrics to establish the error volume or error point cloud "PtC" due to inherent translation errors during arthroscope movement.

In the following, the discussion with reference to FIGS. 9 to 16*d* will analyse the PtC. However, the Inventors found that a problem that arises is that calculating the PtC is too intensive for real-time implementation. Consequently, a subsequent section of the specification discusses an approximation "PtA" or "PCA" of the PtC with reference to FIGS. 17 to 19*b*, which can be implemented in real time and which is implemented in box 65 of the flowchart of FIG. 6.

Figure 9:
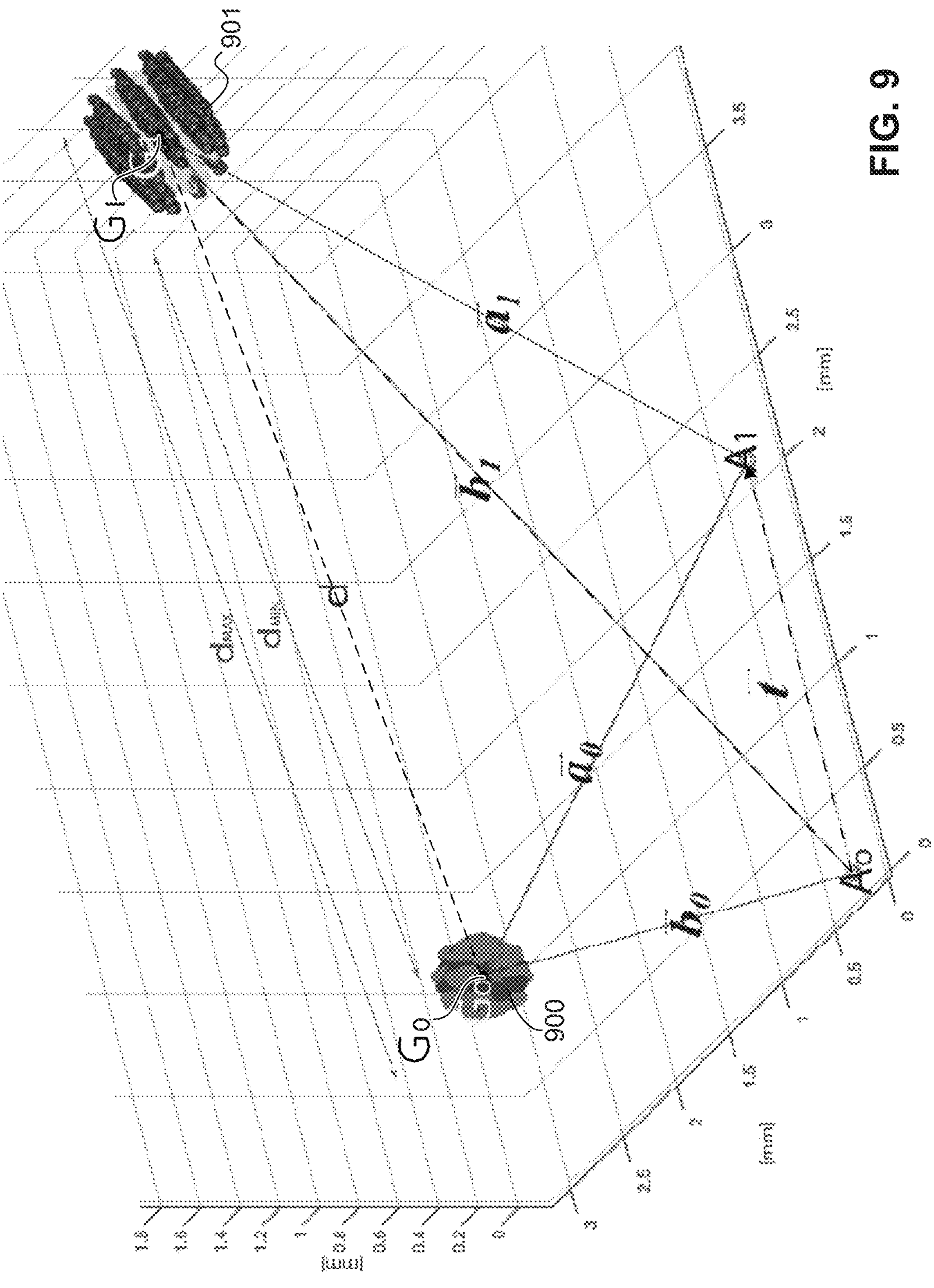
FIG. 9 is a graph indicating an output format for vectors between an instrument gap defined by opposed gap points Go and G1 and arthroscope translation points (Ao and A1) with error cloud points formed around each gap point from each of the vector pairs.

FIG. 9 illustrates the output format for vectors between Instrument gap ($G_0$ and $G_1$) and Arthroscope translation points ($A_0$ and $A_1$) with Error cloud points 900, 901 formed around each gap point $G_0$ and $G_1$ from each of the vector pairs.

Figure 10:
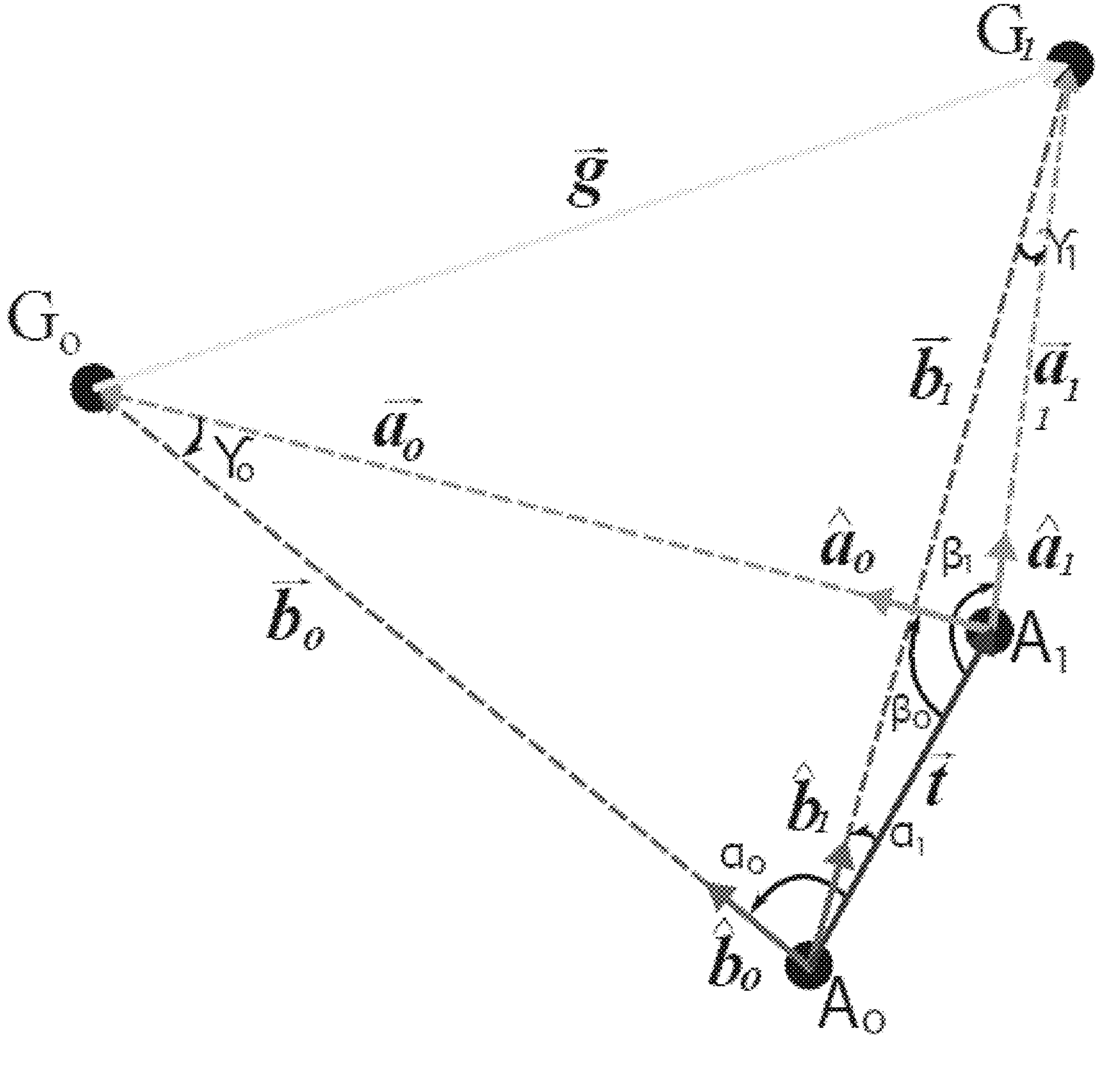
FIG. 10 is a diagram showing measurement of an instrument gap represented by points $G_o$ and $G_1$ from arthroscope camera positions (i.e. the position of the tip of the arthroscope at different times) $A_o$ and $A_1$ with vector $\vec{t}$ the translation of the arthroscope from $A_o$ to $A_1$.

The error clouds were calculated to measure the instrument gap uncertainty; however, the following convention needs to be defined or inferred from FIG. 9:

a) the instrument gap is from $G_0$ to $G_1$ b) the 3D translation vector $\vec{t}$ of the arthroscope is from point $A_0$ initial position to $A_1$ a subsequent position and c) the unit vectors from $A_0$, $A_1$, to the edges of the instrument gap $G_0$, $G_1$ are $\hat{a}_0$, $\hat{a}_1$ $\hat{b}_0$ and $\hat{b}_1$ with angles as shown in FIG. 10.

Each vector configuration has an error volume result—the two error volume pairs, e.g. 900 and 901 are formed from $\vec{a}_0$, $\vec{a}_1$ and $\vec{b}_0$, $\vec{b}_1$ around each gap point $G_0$, $G_1$, respectively. For the test cases, the vector configuration from the instrument gap ($G_0$ and $G_1$, being points on opposite sides of the Gap) relative to the translation path of the arthroscope ($A_0$ to $A_1$) is varied to determine the impact of the translation direction on the error volume.

H. Validation Scenarios

To determine the feasibility of their approach to measure the instrument gap, the Inventors tested the following scenarios:

I. Translation is perpendicular to the line projected onto the x-y plane joining the two gap locations II. Translation is 45 degrees to the line projected onto the x-y plane joining the two gap locations III. Translation is 30 degrees to the line projected onto the x-y plane joining the two gap locations IV. Translation is parallel to the line projected onto the x-y plane joining the two gap locations V. Parameters the same as in scenario 2; however, in this scenario, both the translation and image errors have been set to the maximum values measured to demonstrate a worst-case scenario.

VI. Parameters the same as in scenario 5; however, in this scenario, both the translation distance is increased from 2 mm to 8 mm to determine the change in uncertainty with an increase in translation distance.

VII. Parameters are the same as scenarios 1. However, the translation distance is varied from 0.1 mm to 8 mm to determine the SNR graph.

Scenarios 1-5 were validated over one thousand runs with randomized translation and angular errors to highlight the overall accuracy of the approach. During these scenarios, the instrument gap and translation distance were held constant. The variation in the angle of incidence was deliberate to determine the effect it has on the measurement accuracy. The instrument gap positions were set at 4 mm for $G_0$ to $G_1$ to simulate an actual arthroscope size. The arthroscopes translation magnitude was set to 2 mm, with the vector starting at $(-T \sin(\rho) - T \cos(\rho))$ and ending (0,0,0) mm.

The final scenario demonstrates the signal to noise ratio (SNR) relationship of the gap size compared to the translation distance when the incidence angle is 45° and 90° degrees. The instrument gap size was held constant during scenario 6. However, the translation distance was varied. Parameter values used for the simulations were measured during cadaver experiments.

FIG. 10 illustrates the measuring of the instrument gap distance vector $\vec{g}$ and thus the scalar distance d between points $G_0$ and $G_1$ from camera positions $A_0$ and $A_1$, with $\vec{t}$ the translation of the arthroscope. Once the translation vector and instrument gap direction vectors are known, the vectors from the camera position as detailed in FIG. 10, to the instrument gap coordinates are calculated from the Sine rule as expressed in the equations of FIG. 35B and FIG. 35C, where n represents either the initial or final coordinate (i.e. n=0 or 1). The vector angles, $\alpha_n$, $\beta_n$ and $\gamma_n$ and the distance d between the two edges of instrument gap are expressed using the equations as set forth in FIGS. 35D, 35E, 35F, and 35G, respectively.

The above demonstrates that the distance d between $G_0$ and $G_1$ can be computed using a translation and the direction vectors to the instrument gap coordinates. The next step is to understand the sensitivity characteristics and derive the errors for imperfect measurements.

Error analysis was conducted to form an understanding of how the errors in the measurements of $\vec{t}$ $\hat{a}_0$, $\hat{a}_1$ $\hat{b}_0$ and $\hat{b}_1$ affect the accuracy (or error range) of d. The error analysis enables calculation of the gap range. The arthroscope size (4 mm) relates to the minimum possible dimension of the gap (that will accommodate the arthroscope tip), and the maximum gap dimension is limited by the largest anatomically feasible motion of the patient's joint.

Figure 11:
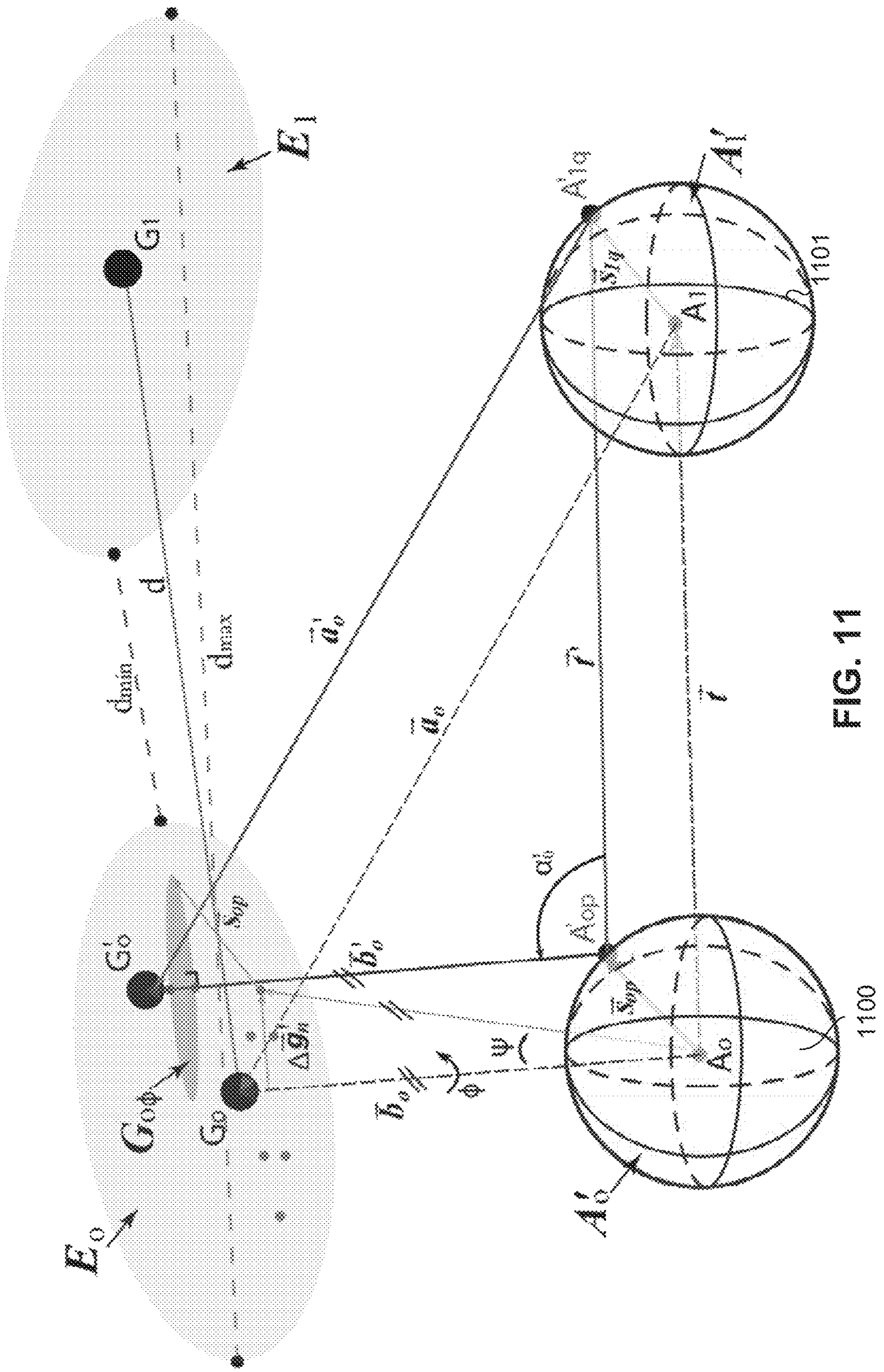
FIG. 11 is a diagram showing error volumes associated with points $G_o$, $G_1$, $A_o$ and $A_1$ of FIG. 10.

The two key measurement errors are: (1) the optical tracking rotation and translation errors and (2) the error in the direction vectors to the instrument gap coordinates. These errors induce a variance in the calculated vector lengths and directions (i.e. errors in $\hat{a}_0$, $\hat{a}_1$, $\vec{b}_0$ and $\vec{b}_1$), which ultimately creates an error volume with an offset close to points $G_0$ and $G_1$ as illustrated in FIG. 11. FIG. 11 illustrates the error volumes, where the translation is $\vec{t}$ and the error translation vector array is $\vec{t}'$. The resulting translation error volumes $A'_0$ and $A'_1$ surround $A_0$ and $A_1$. The total angular error ($\psi$) is the sum of the image ($\theta$) and arthroscope rotational error ($\omega$). $E_0$ and $E_1$ are the final error volumes (shown as the elliptical regions) around the two instrument gap points $G_0$ and $G_1$.

The error analysis will first derive the variation of the magnitude of $\vec{b}_n$, then the angular error due to segmentation and translation rotational errors. From these, the instrument gap error volume is computed, as well as the signal to noise for the instrument gap measurement.

1) Instrument Gap Vectors Length Sensitivity:

Referring to the equation shown in FIG. 35H, if we let the magnitude of $\vec{b}_n$ (or $\vec{a}_n$) be L and the magnitude of the translation ($\vec{t}$) be $\tau$, then L can be expressed as shown in the equation shown in FIG. 35I. The variation in L, $\Delta L$ is then expressed as shown in FIG. 35J. Terms denoted with $\Delta$ are small perturbations in the measurements and the worst case is considered from the equation of FIG. 35J where: $\Delta\alpha_n \cos \alpha_n \leq \Delta\alpha_n$ and where ΔL can be expressed again as shown in FIG. 35K. Note that in FIG. 35K $L=\tau \sin \alpha_n/\sin \gamma_n$ and that second order terms are dropped (i.e. any two small perturbations in measurements multiplied by one another). From the equation of FIG. 35L, it is apparent that as $\gamma_n$ (or $\alpha_n+\beta_n$) approaches 90°, ΔL reduces to a minimum. For a very short translation distance, that is where $\gamma_n$ approaches zero, ΔL become large and the error overshadows the measurement. The translation error changes $\vec{t}$ influence the angles $\alpha_n$ and $\beta_n$, which then change L by ΔL (FIG. 35L), with the Δ values of these angles. However, as we have selected the gap for the simulation and translation points, we can calculate the error in L using these points as ground truth. During an arthroscopy this will not be possible as the actual measurement is unknown.

$$L_{error}=L_{GT}-(L+\Delta L) \tag{1}$$

2) Error Volumes:

Three sets of errors are introduced through measurement conditions:

(1) the error in $\alpha_n$ and $\beta_n$ due to the arthroscope translation measurement, (2) the arthroscope rotational error (ω) around $\vec{\alpha}_n$ and $\vec{b}_n$; and (3) the angular image error (θ) around the computed direction vectors, $\hat{a}_n$ and $\hat{b}_n$.

First the errors due to the translation will be derived. For simplicity, we define the translation measurement error as a spherical volume surrounding $A_0$ and $A_1$, with radius ΔT. Therefore, the start and end points of the translation vector can lie anywhere within these two volumes, respectively, as shown in FIG. 11. To determine the effects of the translational error on the final gap error volumes, we need to determine the effect of 'all' translation vector start and end points.

$A'_0$ is an array that donates all the possible starting points for $\vec{t}'$ and $A'_1$ an array that donates all the possible end points for $\vec{t}'$, where $A'_0$ and $A'_1$ can be expressed as shown in FIG. 35M, wherein ΔT, the translational measurement error, is the measurement precision of the arthroscope translation tracking and randomly varies from zero to a maximum translation error. It is used to scale the unit vector $\hat{r}$, as expressed in FIG. 35N. The azimuth (az) has a range of (−π, π) and elevation (el) has a range of [=−π/2, π/2]. Both $A'_0$ and $A'_1$ are spherical surfaces for a constant ΔT, however as ΔT varies within the measurement system's precision range, an error volume is created around $A_0$ and $A_1$ as seen in FIG. 11 as the spherical volumes 1100 and 1101.

The numerous potential translation vectors $\vec{t}'$, are calculated through iterating through each set of two points p and q in the two translation error volumes $A'_0$ and $A'_1$ respectively. The arrays $A'_0$ and $A'_1$ define a combination of translation vectors so that $\vec{t}'_{p,q}$ can be expressed as shown in FIG. 35O, and where P and Q are the number of points in $A'_0$ and $A'_1$ respectively. With the angular error (ψ), the new translation vector array creates a new set of $\alpha_n$ and $\beta_n$ angles such that $\alpha'_n$ and $\beta'_n$ can be expressed as shown in FIG. 35P. These $\alpha'_n$ and $\beta'_n$ angles can be used to calculate the $\Delta\alpha_n$ and $\Delta\beta_n$ errors, which are required for the equation of FIG. 35L to determine ΔL for calculation of the final error volumes ($E_0$ and $E_1$) around $G_0$ and $G_1$ (see FIG. 35Q).

3) Error Volumes for Knee Arthroscopy:

Image gap measurement errors (θ) and arthroscope rotational errors (ω) both present as angular errors around $\hat{a}_n$ or $\hat{b}_n$ and with the total error range, ψ=±(θ+ω). Through using the previously discussed derived errors (referring to the previous equations as shown in FIG. 35), the final error volumes around the two instrument gap points $E_0$ and $E_1$, can be calculated with the equations as shown in FIG. 35R, respectively, wherein $G_{n\varphi}$ is the array of points that are obtained when rotating $\Delta\vec{g}_n$ around $\vec{a}_n$ and $\vec{b}_n$ and then translating with $\vec{s}_n$, the vectors from $A_0$ to $A'_{0p}$ and $A_1$ to $A'_{1q}$. A magnitude for $\Delta\vec{g}_n$ is expressed as shown in FIG. 35S, where $L=\|\vec{b}_n\|$ and the direction for $\Delta\vec{g}_n$ can be expressed as shown in FIG. 35T so that the result can be expressed as shown in FIG. 35U.

The instrument gap error; which takes into account the measurement errors; between two set of error cloud points is expressed as shown in FIG. 35V. The signal to noise ratio of the instrument gap can be expressed as shown in FIG. 35W. For simulation, the variables can be selected in the ranges and with step sizes as specified in FIG. 35X.

C. Implementation for Reliable Measurements

The $SNR_d$ ratio (FIG. 35W) can be used to decide if more translation is required or if the gap is defined to an adequate degree to decide on a specific action for the operator. The level for $SNR_d$ will need to be set for a specific procedure and conditions to ensure successful transition to a specific part of the knee.

The analysis can be viewed from both the $\vec{a}_n$ or $\vec{b}_n$ or a combination can be used to determine the best $SNR_d$ value.

Results are now provided for the six test cases in a format as detailed in FIGS. 9 and 11.

A. Image Errors

The instrument gap was segmented for a thousand images selected from different regions of the knee and compared against images marked-up by an expert surgeon as seen in FIG. 12.

FIG. 12 depicts Segmentation and image Errors of the instrument gap for two areas inside the knee joint using the OTSU algorithm: (boxes a,e) Arthroscope Video frame, (b,f) Markedup Image, (c,g) OTSU Mask, (d,h) SAD output with image errors FP (false positives) and FN (false negatives).

The calculation of the image angular error (ψ) is then computed, as the angular resolution of each pixel is known.

The average image errors (θ) was calculated as detailed in Table 1 for selected diagnostic points inside the knee. The medial compartment is one of the first spaces seen during an arthroscopy and its image error (item 2) of 2.36° will be used for detailed analysis in this study.

TABLE 1

Image errors at specific diagnostic points inside the knee joint. Errors around the two gap points are calculated, with the average between these points provided.

| No. | Image Set | Location Inside the Knee Joint | $G_0$ Gap Error | $G_1$ Gap Error | Ave Image Error |
|---|---|---|---|---|---|
| 1 | 2 | Medial Compartment | 5.215 | 3.388 | 4.302 |
| 2 | 3 | Patellar Femoral Joint | 1.961 | 2.774 | 2.367 |
| 3 | 6 | Lateral Compartment | 4.048 | 7.125 | 5.586 |

The RMS error for the Optitrack translation (ΔT) is 0.0367 mm recorded over all the ten data sets. The average arthroscope rotational error (ω) is 0.03° over the data sets. The translation measured during the cadaver experiments are detailed in Table 2.

FIGS. 13*a* and 14*a*-14*d* are the results for scenarios one to five (from 0° to 90°) for the cloud points with vectors, and FIG. 9(*b*) the delta L error for zero degrees translation (12). The results from these figures are shown in Table 2.

TABLE 2

Simulation Parameters.

| Set | Translation Angles | ΔT [mm] | Gap (d) [mm] | t [mm] | Θ | ω |
|---|---|---|---|---|---|---|
| 1 | 0°, 30°, 45°, 90° | 0.0367 | 4 | 2 | 2.36° | 0.004° |
| 2 | 45°, | 0.0698 | 4 | 2 | 5.586° | 0.177° |
| 3 | 45°, | 0.0698 | 4 | 8 | 5.586° | 0.177° |
| 4 | 90°, | 0.0367 | 4 | 0.1:0.1:8 | 2.36° | 0.004° |

Set 1 is the average errors, set 2 the maximum measured translation and image errors, set 3 with a fixed 8 mm translation and with set 4 the translation distance is varied.

TABLE 3

Instrument gap Error Analysis Results

| Parameter | Translation | Uncertainty (Range) | | Gap Measurement Error | | Scenario |
|---|---|---|---|---|---|---|
| Set | Angle | Min | Max | Mean | Std Dev | # |
| 1 | 0° | 3.351 | 4.724 | −0.0052 | 0.0147 | 1 |
| | 30° | 3.492 | 4.525 | −0.0032 | 0.0086 | 2 |
| | 45° | 3.346 | 4.562 | −0.0067 | 0.0052 | 3 |
| | 90° | 3.515 | 4.497 | 0.0221 | 0.0054 | 4 |
| Average Set 1 | | 3.426 | 4.577 | 0.0018 | 0.0085 | |
| 2 | 45° | 2.875 | 5.256 | −0.019 | 0.0016 | 5 |
| 3 | 45° | 3.525 | 4.495 | 0.0063 | 0.0013 | 6 |
| 4 | 90° | SNR Graph | | | | 7 |

With scenario one to four (set 1 of Table 2) the measurements from changing the translation angle (using image set 2). Scenario five (set 2) use 2 mm translation with the maximum measure errors at 45° for both translation and image. Scenario six (set 3) used the same parameters as scenario 5, but with an 8 mm translation and in scenario 7 the translation is varied from 0.1 mm to 8 mm to plot the SNR graph.

Figure 13A:
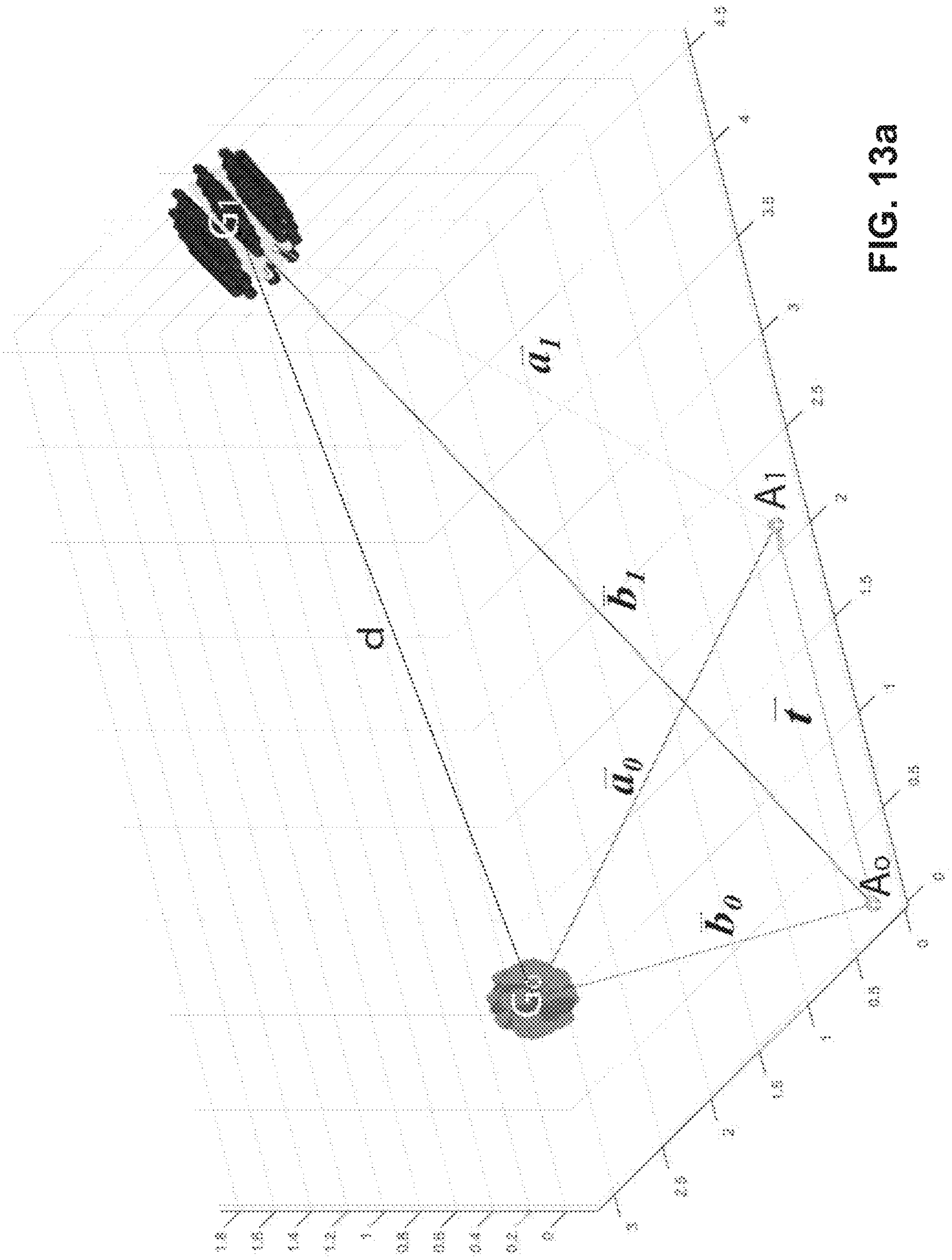
FIG. 13*a* is a graph showing a point cloud around each gap point Go, G1 with a fixed translation distance of 2 mm and gap of 4 mm.
Figure 13B:
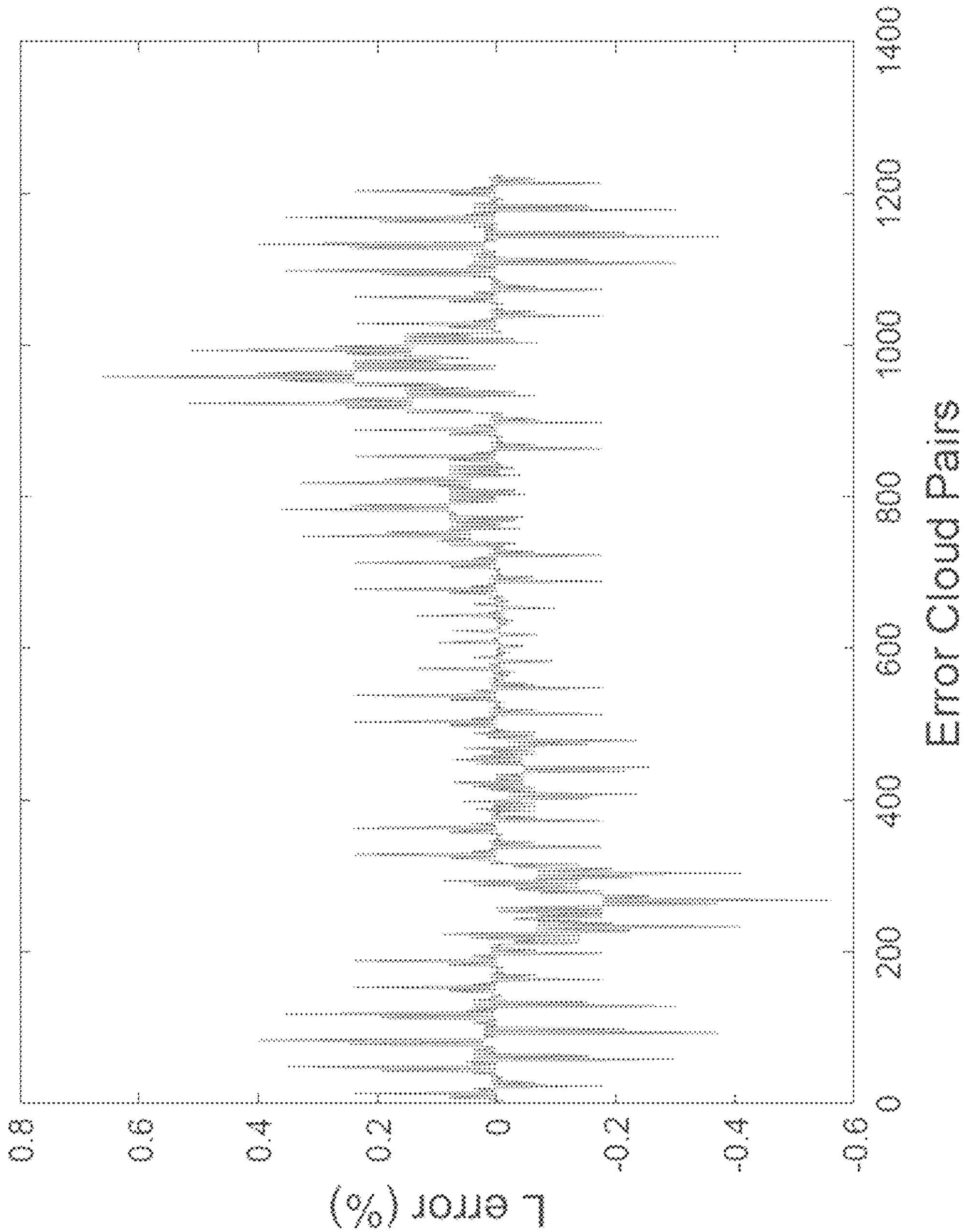
FIG. 13*b* is a graph of L Error showing the variation of delta ΔL+L from the ground truth Length for L.

FIG. 13*a* shows the Point Cloud around each Gap point, with a fixed translation distance of 2 mm and gap of 4 mm with 0° translation (i.e. the $\vec{t}$ vector is parallel to the x axis). FIG. 13*b* is a graph of the L Error showing the variation of ΔL+L from the ground truth Length for L with 0° translation.

Figure 14A:
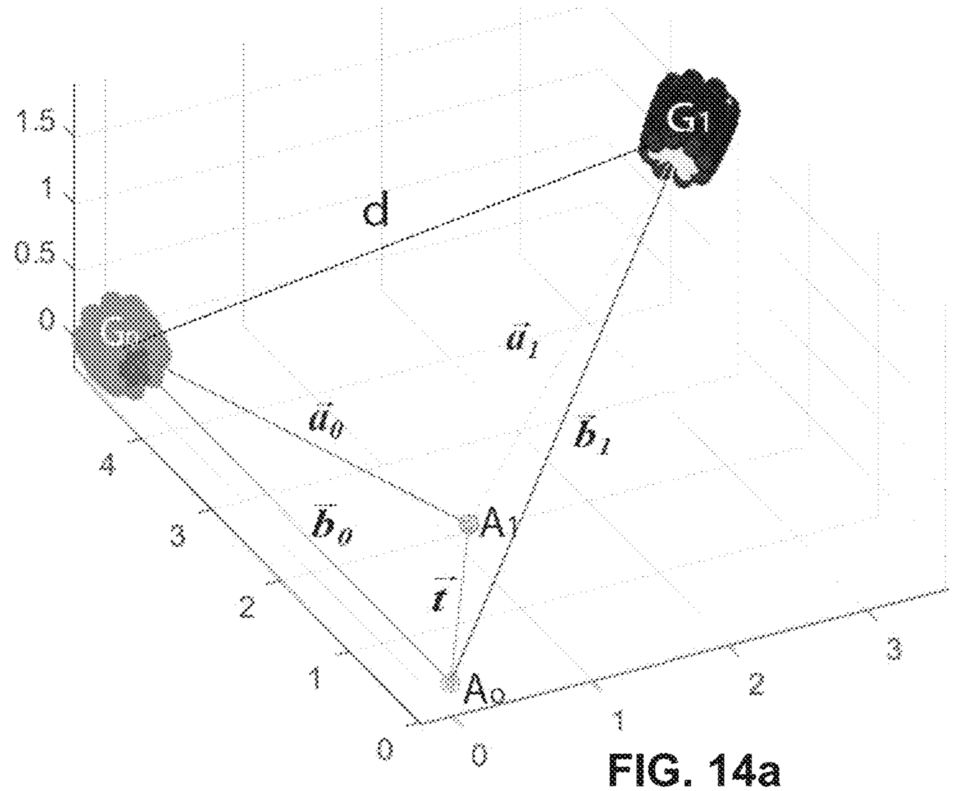
FIG. 14*a* is a graph of showing translation error point clouds around the gap points of 4 mm at 30° with 2 mm translation of the arthroscope.
Figure 14B:
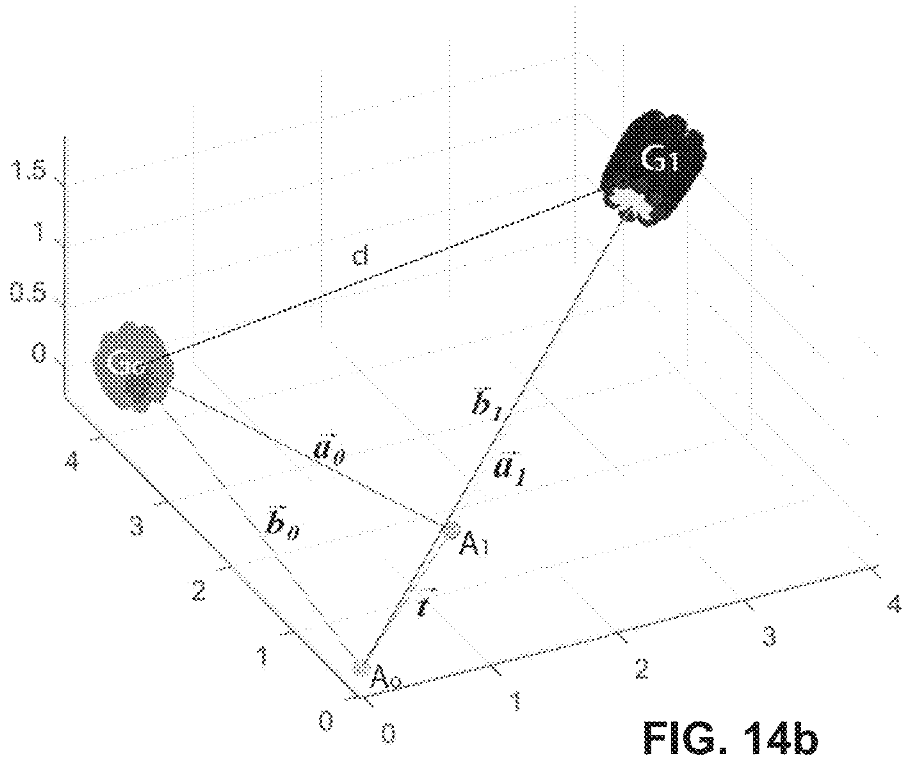
FIG. 14*b* is a graph of showing translation error point clouds around the gap of 4 mm at 45° with 2 mm translation of the arthroscope.
Figure 14C:
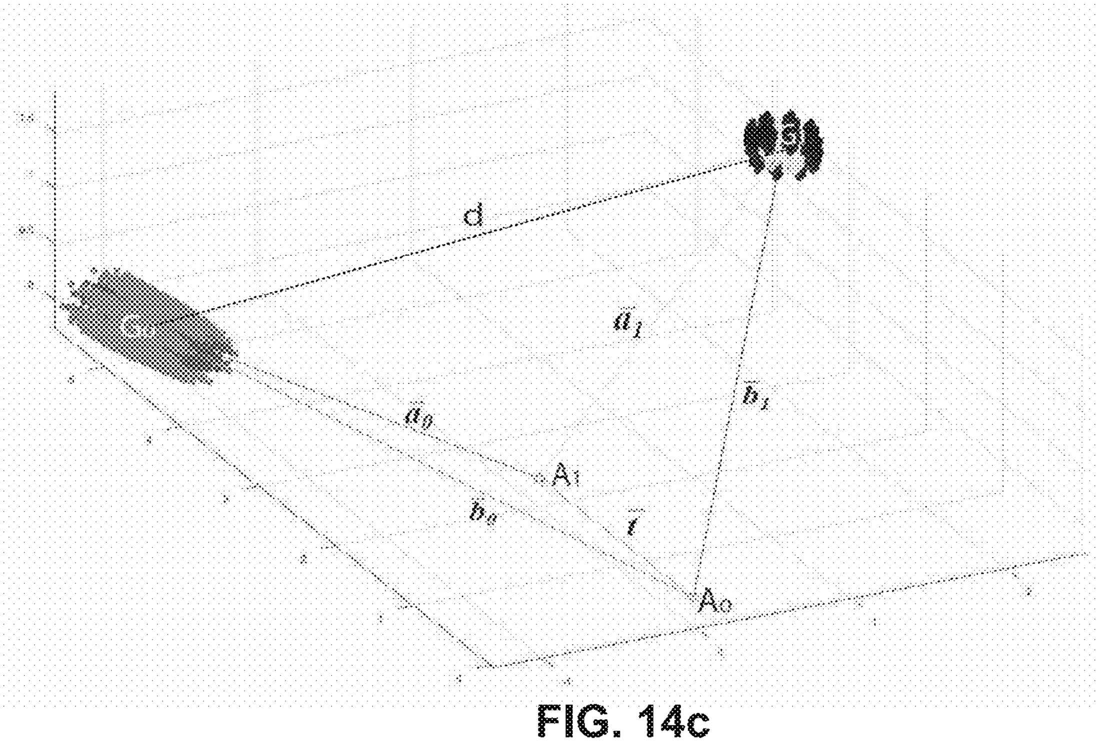
FIG. 14*c* is a graph of showing translation error point clouds around the gap of 4 mm at 90° with 2 mm translation of the arthroscope.
Figure 14D:
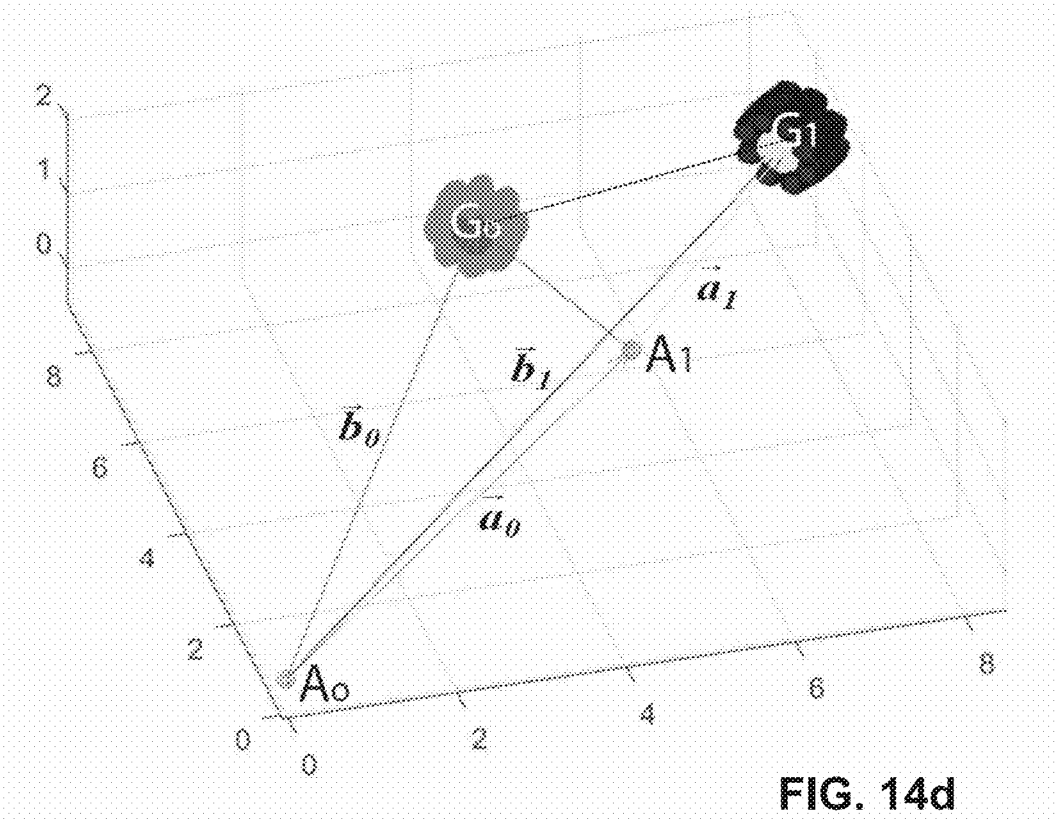
FIG. 14*d* is a graph of showing translation error point clouds around the gap of 4 mm at 45° with 8 mm translation of the arthroscope.

FIGS. 14*a*-14*d* graphically represent translation point clouds around the gap of 4 mm. In FIG. 14*a* the cloud points at are calculated for 30° with 2 mm translation. In FIG. 14*b* the cloud points are calculated for 45° with 2 mm translation. In FIG. 14*c* the cloud points are calculated at 90° with 2 mm translation.

Figure 15A:
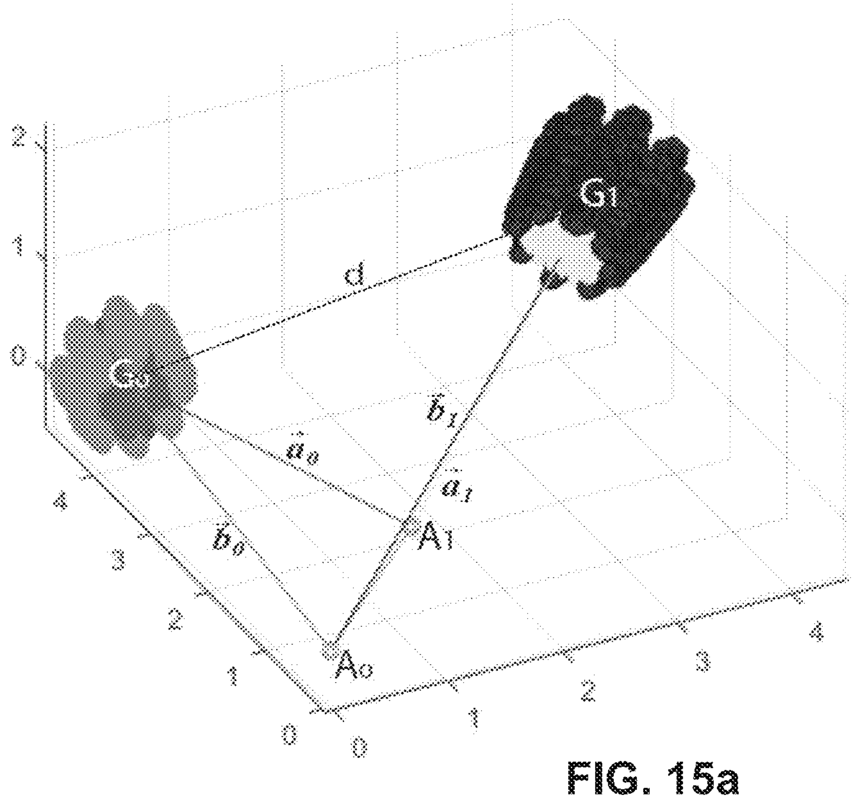
FIG. 15*a* is a graph with parameters as detailed in Image Set 2 of Table 2.
Figure 15B:
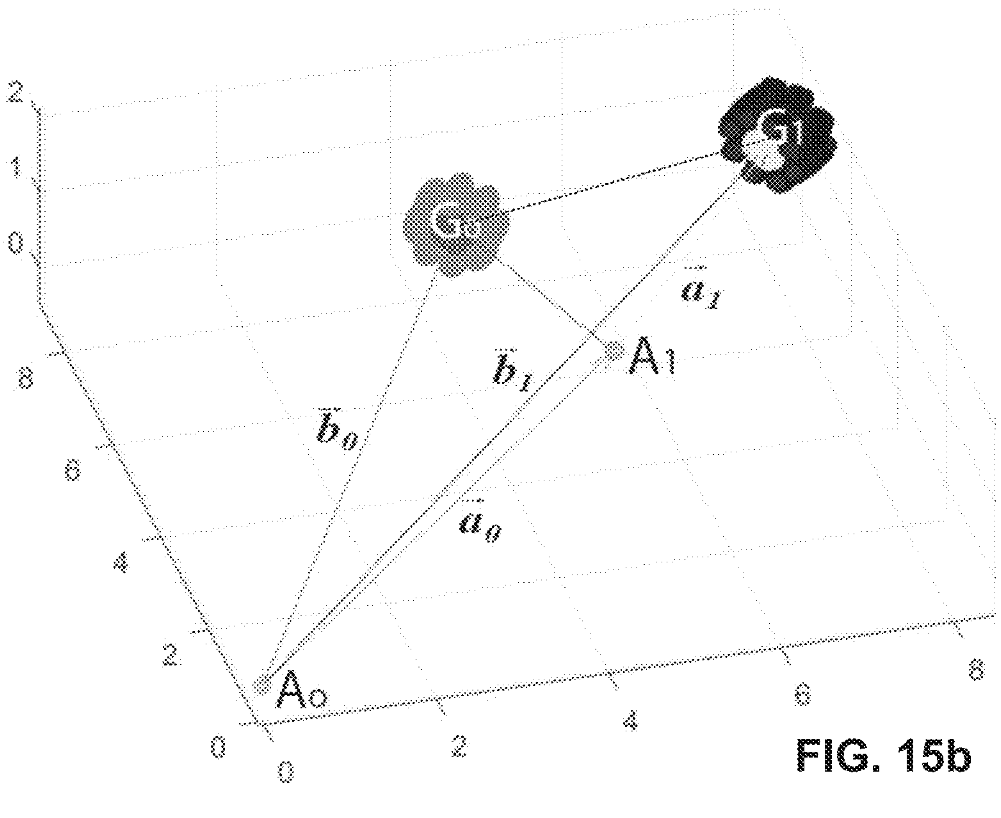
FIG. 15*b* is a graph with parameters as detailed in Image Set 3 of Table 2.

FIGS. 15*a* and 15*b* illustrate the impact on the error clouds of an increase in translation from 2 mm (FIG. 15*a*) to 8 mm (FIG. 15*b*), with parameters as detailed in Image sets 2 and 3 in Table 2. The translations are at 45°, with an instrument gap of 4 mm and a ΔT of 0.0698 mm.

Scenarios 5 and 6 in Table 3 are presented in FIG. 11 and are the results for the maximum measured error ranges (Table 3—Set 2 and 3) and emphasize translation distance influence on the error point cloud. Table 3 includes the gap for various angles, and the mean and standard deviation error of the motion stereo over one thousand test runs. The uncertainty was calculated from the point cloud extremes and the average gap over the thousand runs provided for each translation angle (each with a random translation and angular error bounded by sensing system parameters, namely image resolution and frame rate).

Figure 16A:
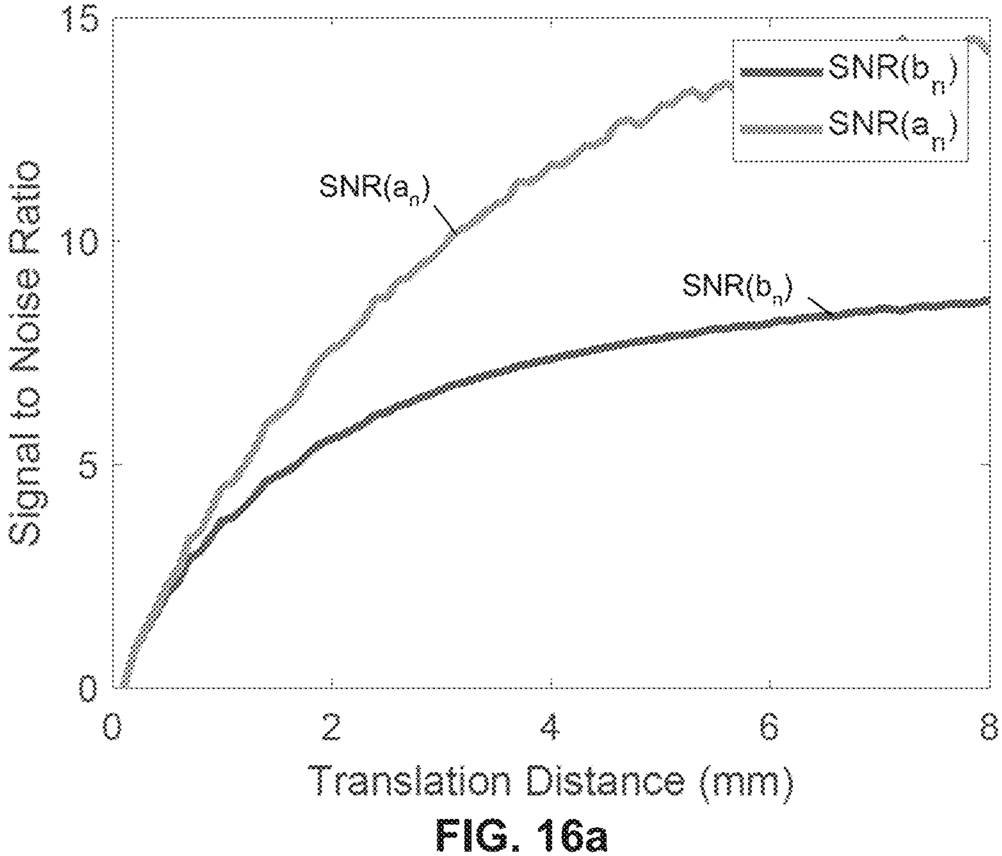
FIG. 16*a* is a graph of signal to noise rations (SNR) of the measured gap distance (ground truth distance) compared to gap range using a calculated error cloud uncertainty as per set 2 in Table 2 with 2 mm translation.
Figure 16B:
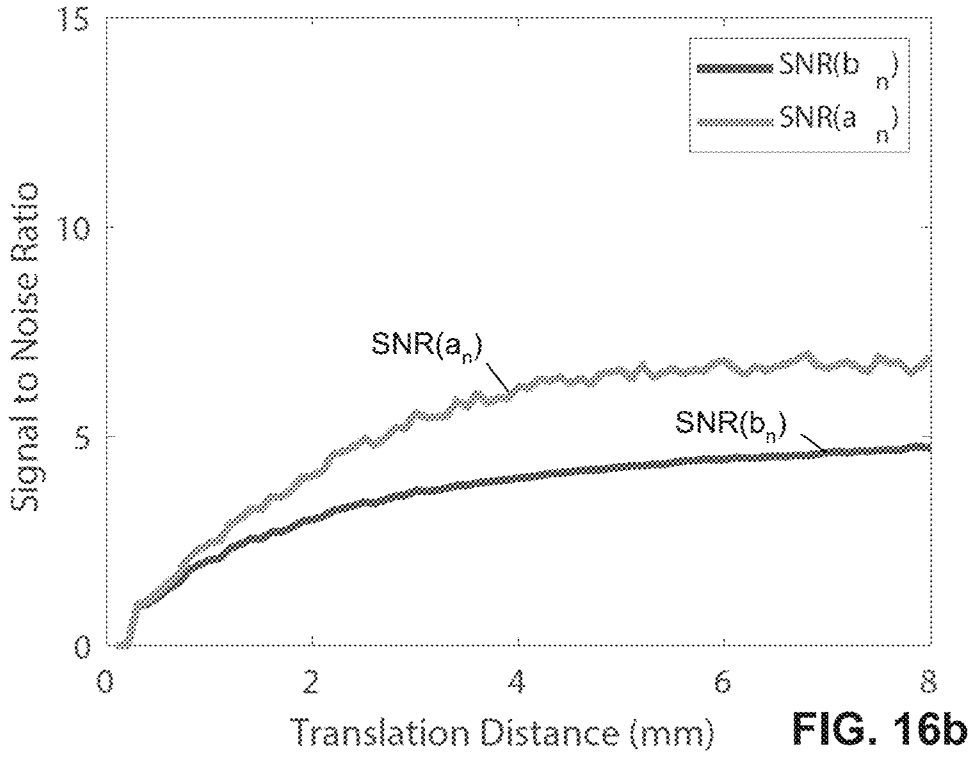
FIG. 16*b* is a graph of signal to noise rations (SNR) of the measured gap distance (ground truth distance) compared to gap range using a calculated error cloud uncertainty as per set 2 in Table 3 with 2 mm translation.

FIGS. 16*a* and 16*b* show SNRs for set 2 in Table 2 and set 3 in Table 2 respectively. As the arthroscope moves through the knee during surgery, it is necessary to constantly adjust the patient's leg position to create the appropriate space for the surgical equipment. The anatomical joint safe range (or upper limits) of the patient is known to control the maximum force that can be applied to a joint at each leg position. Surgeons currently "feel" the limb resistance. In conjunction with 'feeling' the force they apply to the leg, surgeons further estimate the joint space from a 2D video steam in front of them. In many cases, they over or underestimate the instrument gap, resulting in damaging to the knee joint by applying excessive force to it or pushing the instrument through a gap that is too small. Computer vision is ideally placed to reduce trauma to patients, by measuring this "instrument gap" and provide feedback to the operator, whether it is a robot or surgeon. The previous discussion provides a procedure for determining the uncertainty or range of measuring the instrument gap inside the knee joint. It is a minimum where surgical tools need to pass through and a maximum at the joint motion limits.

Optical sensor and image processing noise were measured during cadaveric experiments and used to verify the approach through simulation. The results show that under perfect conditions and using motion stereo, we can accurately measure the instrument gap.

Although, under perfect conditions and using motion stereo, it is possible to accurately measure the instrument gap, a high level of uncertainty is introduced with the image processing and arthroscope motion measurements, impacting the actual instrument gap measurement by ±14%.

The results in Table 3 demonstrate that motion stereo accurately measures the instrument gap. The average of the measurements has a mean of −0.0028 mm and standard deviation of 0.0096 mm. These results are well within the accuracy range that can be achieved by surgeons or robots. However, from cadaver measurements, significant noise is present in the form of image segmentation and translation measurements errors that influences the motion measurements. These errors were analysed, and algorithms developed to measure the uncertainty range of the instrument gap.

The range measurement is defined by the errors inherent to an arthroscopy setup and conveniently reflects the two extremes for any surgery: (1) the minimum size required for the arthroscope to pass through the space safely and (2) the maximum gap size due to the human's anatomical limit. A practical outcome of this research is that the uncertainty range can effectively be used as a guide during the surgery.

Image errors from segmentation were converted to spherical coordinates, and from Table 1 these errors are significant and have an impact on the uncertainty range. The OTSU segmentation method used is fast and with an adequate level of accuracy [4], providing a good indication of how the identification of the instrument gap influences the gap measurement accuracy. However, in developing techniques such as using deep learning algorithms [29], these errors will reduce over time, improving the overall uncertainty range of the instrument gap measurement.

Tracking the arthroscope introduced translation and rotation errors as presented in Table 2 that form point clouds around the translation points and vectors to the instrument gap. Optical tracking precision is high, with the translation error 0.0367 mm. However, it has an amplification impact on the rotational error volumes, translating them in all directions around the gap points. The optical tracking rotational error is insignificant (0.004°) and negligible in comparison to the image error.

FIGS. 16*a* and 16*b* graph the Signal to Noise Ratios of the measured gap distance (ground truth distance) compared to gap range, using the calculated error cloud uncertainty. In FIG. 16*a* the errors are as per set 2 in Table 2 with a 2 mm translation. In FIG. 16*b* the errors are as per set 3 in Table 2 with an 8 mm translation.

Error volume results in FIGS. 13*a* to 14*d* show that images with a combination of rotation and translation errors and different translation directions have different error point clouds surrounding the two gap points. Each volume is relative to a set of vectors $\vec{a}_0$ and $\vec{b}_0$ or $\vec{a}_1$ or $\vec{b}_1$ and is independent in shape and size due to the unique noise and error characteristics of each triangulation vector. Indeed, the best combination of the four error volumes can be used for feedback and control purposes. The minimum and maximum instrument gap range values calculated from these point clouds are presented in Table 3, for the four translation angles (using $\vec{b}_n$). The larger the image and translation errors, the larger the volumes as shown for 45° between FIGS. 14*b* and 14*d*.

The results in Table 3 shows the best angle to be 45° and that in general, the higher angles are slightly worse than the lower angles. The change is marginal, and the translation angle doesn't have a significant impact (maximum 0.169 mm) on the uncertainty range. The actual gap size was set at 4 mm during the simulation and indicated that by taking into account the uncertainty, the gap size is underestimated by 13.91% and overestimated it by 14.03% as shown in Table 3. The total uncertainty range is on average 1.1172 mm or 27% of the actual gap size. At the minimum side, we thus need to increase the gap until it is more than 4 mm to ensure the arthroscope can safely pass through, however, the anatomical limits of the patient's joint needs to be considered.

Using a signal to noise approach it is possible to change the measurement accuracy through controlling the arthroscope translation distance as shown by the signal to noise graphs in FIGS. 16*a*, 16*b* and the resulting cloud volumes in FIGS. 15*a*, 15*b*. The potential benefit of the $SNR_d$ value is that it provides a single metric to determine the accuracy of the gap measurement. The length of the $\vec{a}_n$ or $\vec{b}_n$ vectors depends on the gap position and the initial and final translation points. These vector lengths change the size of the error clouds, and different vector combinations will result in a higher or lower $SNR_d$. Using this $SNR_d$ graph, a threshold can be set at the desired noise level for a specific surgical procedure. Once the desired noise to signal is reached, the measurement values are within the predefined tolerances for the surgery. Larger error volumes for the same translation lower the $SNR_d$, reducing the accuracy and control range as shown between FIGS. 16*a* and 16*b*.

The primary focus of the uncertainty analysis that has been set out is to calculate the noise parameters during motion stereo measurement of the instrument gap to determine the uncertainty in the gap size. Using imperfect state information in real environments (from low cost or existing sensors), can be used to provide sufficient information for a range of applications, including: Measuring system inside the knee joint using a standard arthroscope for surgeon feedback, or robotic applications during automated knee arthroscopy; Minimal invasive surgery of other joints in the body; and Land and any underwater robotic applications to accurately measure range with motion cameras, while characterising the uncertainty Measuring the surgical space, i.e. the instrument gap, inside the knee joint for minimally invasive surgery has significant benefits for both the patient and surgeon. The Inventors have found that that using computer vision, images from a standard arthroscope can be used to measure the instrument gap and calculate the uncertainty range of the measurement.

Approximation of the Uncertainty Point Cloud to Determine Measurement Uncertainty (Box 65)

The uncertainty point cloud "PtC" about $G_0$ and $G_1$ that has been discussed shows in detail all the combinations of vectors impacting the minimum and maximum instrument gap range, however it is not processed in real-time and thus not beneficial during an actual arthroscopy. It is desirable to implement a method to approximate the PtC to enable the processing assembly 126 to perform real-time analysis of the knee joint, measuring the instrument gap as the surgery progresses, and thus significantly reduce patient trauma. The gap size and uncertainty range can be used, in some embodiments, to provide feedback to a surgeon while moving surgical instruments through the knee joint, for example by means of a visual display, or, in other embodiments, to enable control of robotic leg manipulator 100.

In the following it is assumed that a standard arthroscope (used during four million surgeries per year) is used, i.e. arthroscope 40, and the joint in question, e.g. a knee joint, is not moving while the point-cloud is approximated. The time and accuracy between the calculation of measuring the uncertainty using a PtC or using an approximation of the PtC, i.e. ("PtA" or as it is sometimes referred to herein "PCA") in measuring the front, medial instrument gap will be analysed. Segmentation and optical tracking error as previously discussed will form part of a mathematical approximation model. The instrument gap (d) between points $G_o$ and $G_1$ and the variation in L, ΔL is given by equations as previously discussed.

The distance (d) can be computed using a known translation and the direction vectors to the instrument gap coordinates. The sensitivity characteristics and the errors for imperfect measurements will now be discussed.

Figure 17:
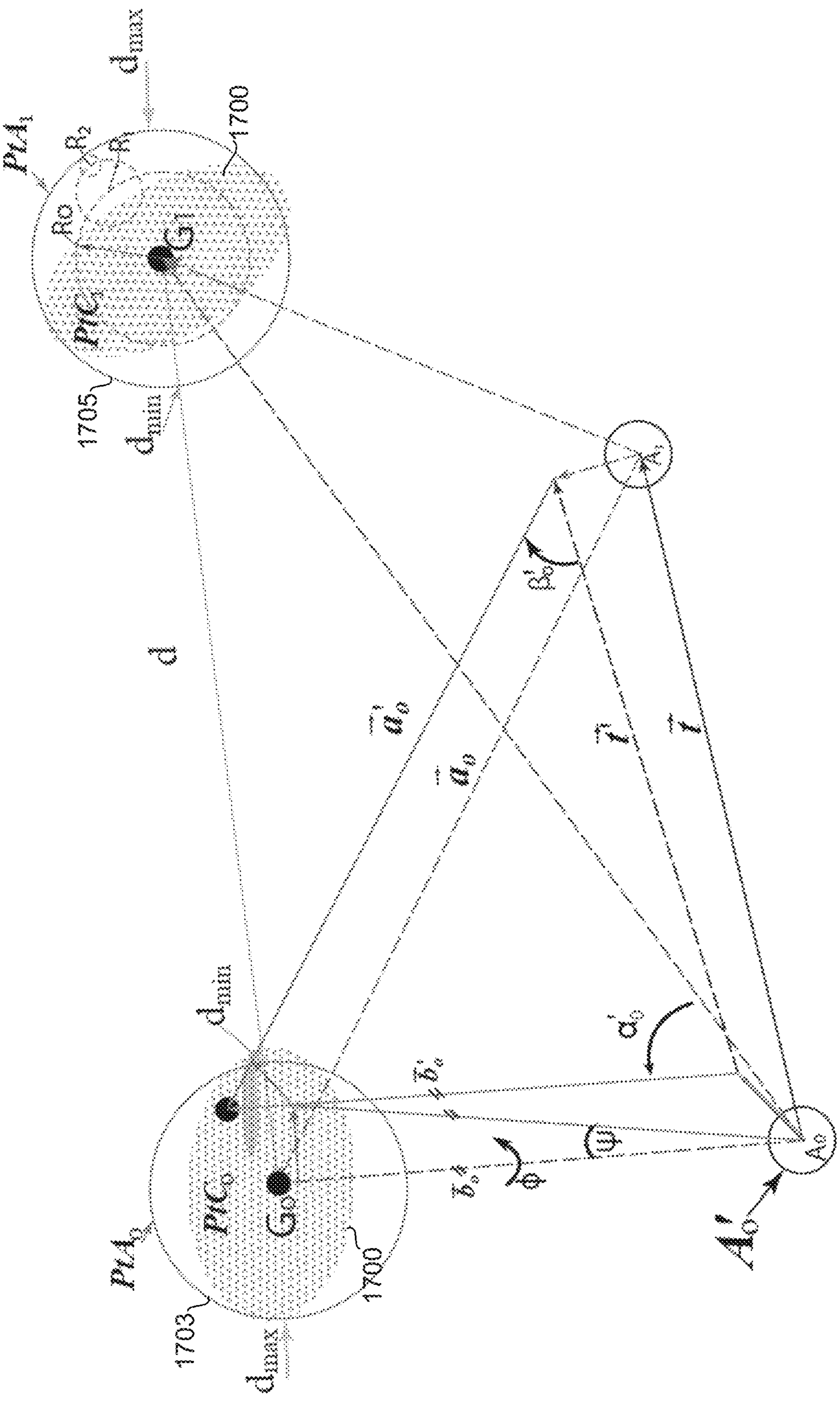
FIG. 17 is a diagram graphically illustrating the determination of approximation error clouds $PtA_0$ and $PtA_1$ around two instrument gap points $G_0$ and $G_1$.

FIG. 17 is a diagram illustrating measurement of the instrument gap represented by point $G_0$ and $G_1$ from arthroscope camera positions $A_0$ and $A_1$, with $\vec{t}$ the translation of the arthroscope. The point cloud error volume setup is shown around $G_o$ with the translation $\vec{t}$ and the error translation vector array $\vec{t}'$. The resulting translation error volumes $A'_0$ and $A'_1$ surround $A_0$ and $A_1$. The total angular error (ψ) is the sum of the image (θ) and arthroscope rotational error (ω). $PtC_0$ and $PtC_1$ are the final error point cloud volumes (shown as the dotted areas 1700 and 1701). The approximation cloud $PtA_0$ and $PtA_1$ are shown as the spheres 1703 and 1705 around the two instrument gap points $G_o$, $G_1$. The approximation error volume setup is shown around $G_1$, with the $R_0$ the radius of the segmentation error, $R_1$ the radius of the optical tracking translation error, $R_2$ the radius of the optical tracking rotational error.

The error PtC as shown in FIG. 17 around the two instrument gap points is E0 and E1 can be expressed as shown in FIG. 35Y, with $G_{n\varphi}$ being the array of points obtained when rotating $\Delta\vec{g}_n$ around $\vec{a}_n$ or $\vec{b}_n$ and then translating with $\vec{s}_n$, the vectors from $A_o$ to $A'_{op}$ and $A_1$ to $A'_{1p}$. We find the instrument gap, as expressed om FIG. 35Z, which takes into account the minimum and maximum measurement errors between two set of error cloud points.

For the cloud point approximation, we rotate the translation error around the segmentation error as illustrated in FIG. 17 to find the outer surface of the uncertainty $\theta_T$ (as shown in FIG. 36A). From the equation of FIG. 35L, we obtain the expression of $r_{n2}$ as expressed in FIG. 36B and $r_{n1}$ as expressed in FIG. 36C. From here, we can find the range for $d_{min}$ and $d_{max}$, as shown in FIG. 36D.

Surgical assistance software 27 includes instructions that configure processing assembly 126 to estimate the distance d between the gap points $G_o$, $G_1$ and then find the $d_{min}$ and $d_{max}$ value taking into account uncertainty in the arthroscope translation and image segmentation. These instructions are executed by processing assembly 126 at boxes 63 and 65 of the flowchart of FIG. 6 (using the segmentation image error from box 67) to calculate a gap measurement at box 68 and output a Measured Gap size at box 68 taking into account the approximated error PtA.

The Inventors determined the feasibility of the approximation approach to measure the instrument gap by varying the translation from 0° to 90° to the line projected onto the x-y plane joining the two gap locations as detailed in Table 4 shown in FIG. 36E, showing the average segmentation error is used and during set 4 the translation is 8 mm in Table 4, scenarios 1-4 are were processed for both the PtC and PtA (i.e. approximated uncertainty point clouds) and the time recorded for each. The instrument gap ($G_0$ to $G_1$) and translation distance ($A_0$ to $A_1$) were held constant at 4 mm and 2 mm for the first three sets with 8 mm translated during set 4.

Figure 18A:
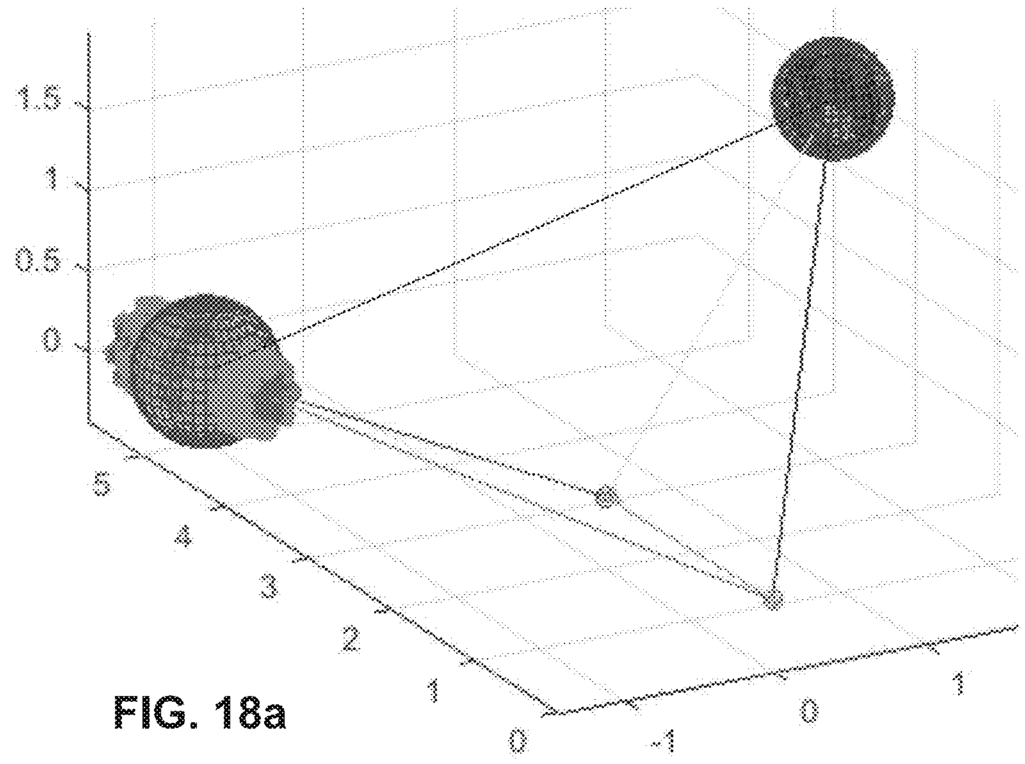
FIG. 18*a* depicts an error approximation cloud for cloud points at 0° with a gap of 4 mm and arthroscope translation of 2 mm.
Figure 18B:
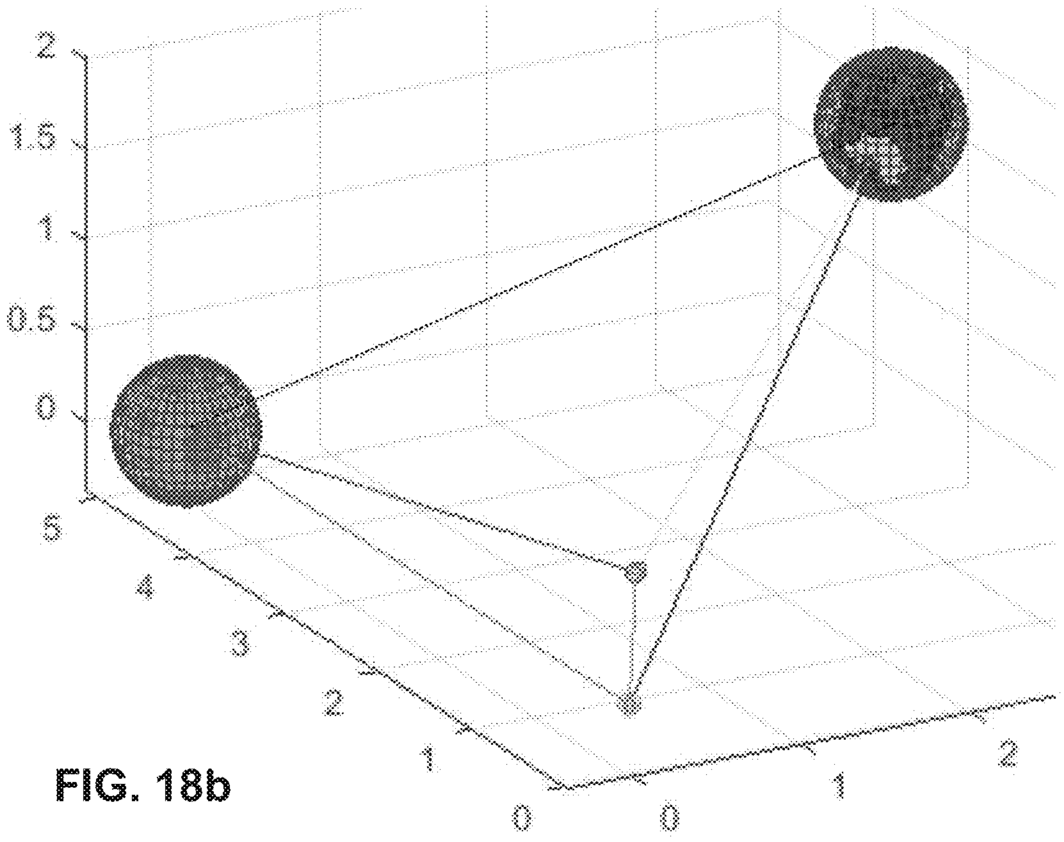
FIG. 18*b* depicts an error approximation cloud for cloud points at 30° with a gap of 4 mm and arthroscope translation of 2 mm.
Figure 18C:
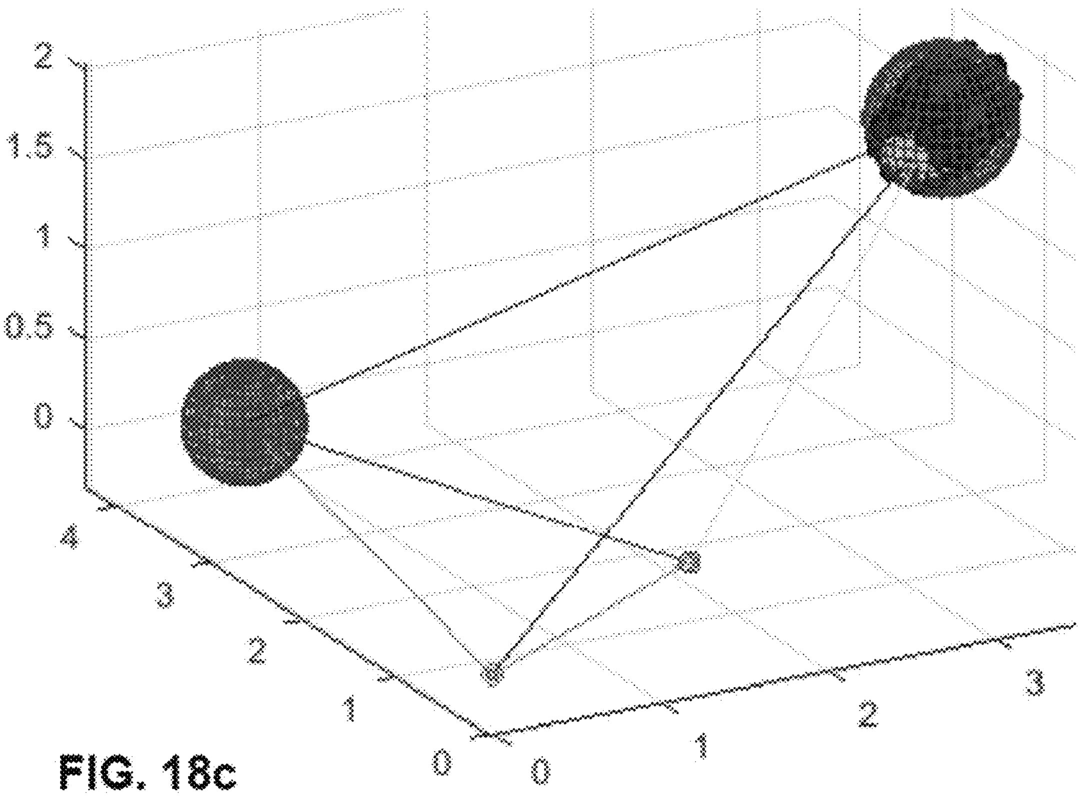
FIG. 18*c* depicts an error approximation cloud for cloud points at 60° with a gap of 4 mm and arthroscope translation of 2 mm.
Figure 18D:
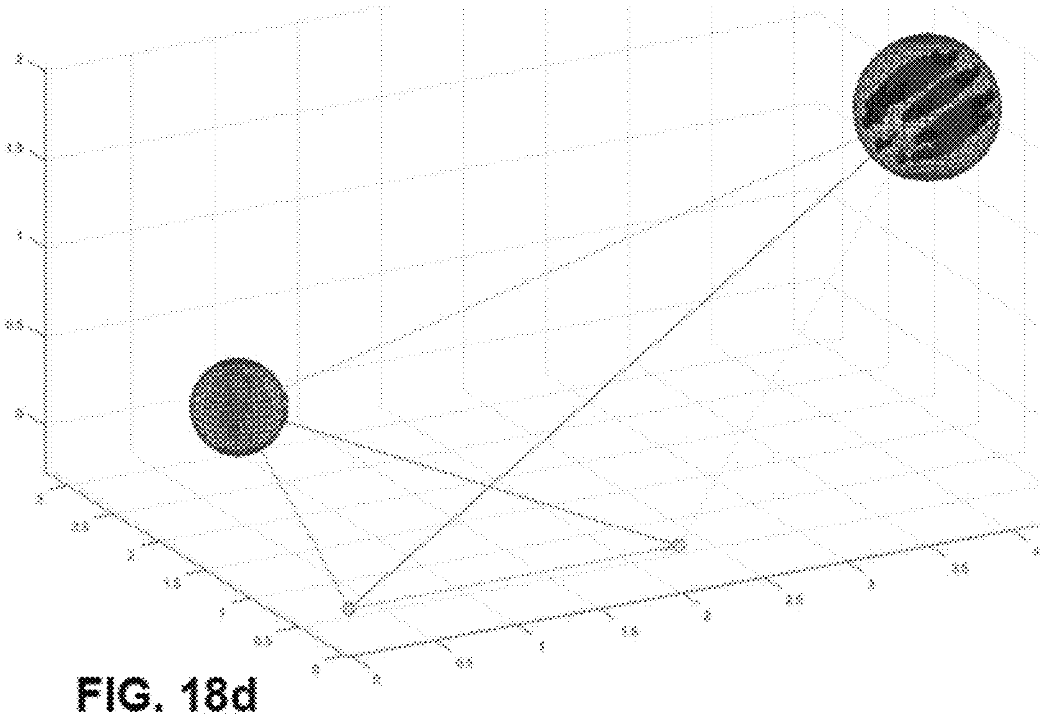
FIG. 18*d* depicts an error approximation cloud for cloud points at 90° with a gap of 4 mm and arthroscope translation of 8 mm.

FIGS. 18*a* to 18*c* are the results for scenarios 1 to 3 (from 0° to 60°) in Table 4 for the cloud points with vectors. FIG. 18*d* shows the error clouds for scenario 4, i.e. sixty degrees with an 8 mm translation and shows the influence of the translation distance on the error clouds.

The complexity of the knee cavity and unintended damage to patient knees support research to automate leg manipulation or to provide feedback to surgeons during a knee arthroscopy. As a first step it is necessary to measure the instrument gap to ensure free movement of surgical instruments without causing damage. Motion stereo has been found to be a viable and accurate method to measure the joint using images from a standard arthroscope. However, measurement errors are introduced from segmentation and optical marker tracking, from which an error point cloud can be calculated. The Inventors sought to approximate the error cloud as shown in FIG. 17, to improve processing time while retaining the measurement accuracy of the instrument gap for real-time surgical applications. The segmentation error, the intersection of the travel direction and the gap is significantly smaller than the average for the image sets and will be evaluated to determine the impact of an approximation of the cloud points to the overall accuracy of the gap.

Using spherical surface approximations of the point cloud, support the worst-case scenario as only the outer surface is considered. The approximation error clouds for the parameters as detailed in Table 4 for scenario 1 are shown in FIGS. 18*a* to 18*d*, where both the point clouds and the approximation clouds for each vector combination are shown. These volumes are due to the measured errors and a set of vectors $\vec{a}_0$ and $\vec{b}_0$ or $\vec{a}_1$ and $\vec{b}_1$. Any combination of the error volumes on each side of the gap can be used to measure the instrument gap. From the figures the approximation clouds closely encase the point clouds, however for a 0° translation the point cloud stretches along the vector, where the approximation cloud doesn't, impacting the accuracy of the instrument gap measurement.

In some approximations, optical translational and rotational tracking errors can be 0.0367 mm and 0.004° respectively. Although both these are negligible in comparison to the average image segmentation error of 3.6°, the optical translational error amplifies the segmentation error to form the point cloud, which can be approximated as shown in FIGS. 19*a* and 19*b*.

Figure 19A:
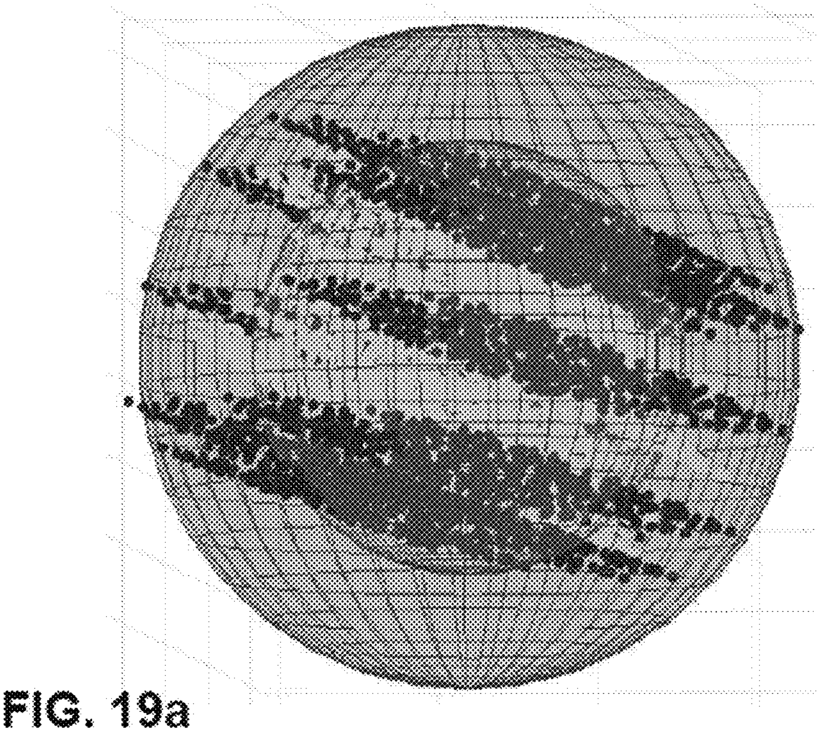
FIG. 19*a* depicts PtC (error cloud) and PtA (approximated error cloud) volumes at 60° at the $G_0$ side of the gap corresponding to FIG. 18*c*.

FIG. 19*a* shows PtC and PtA Volume 0 at 60° (FIG. 18*c*) showing the two approximation and point clouds on the $G_o$ side due to the two vector combinations.

Figure 19B:
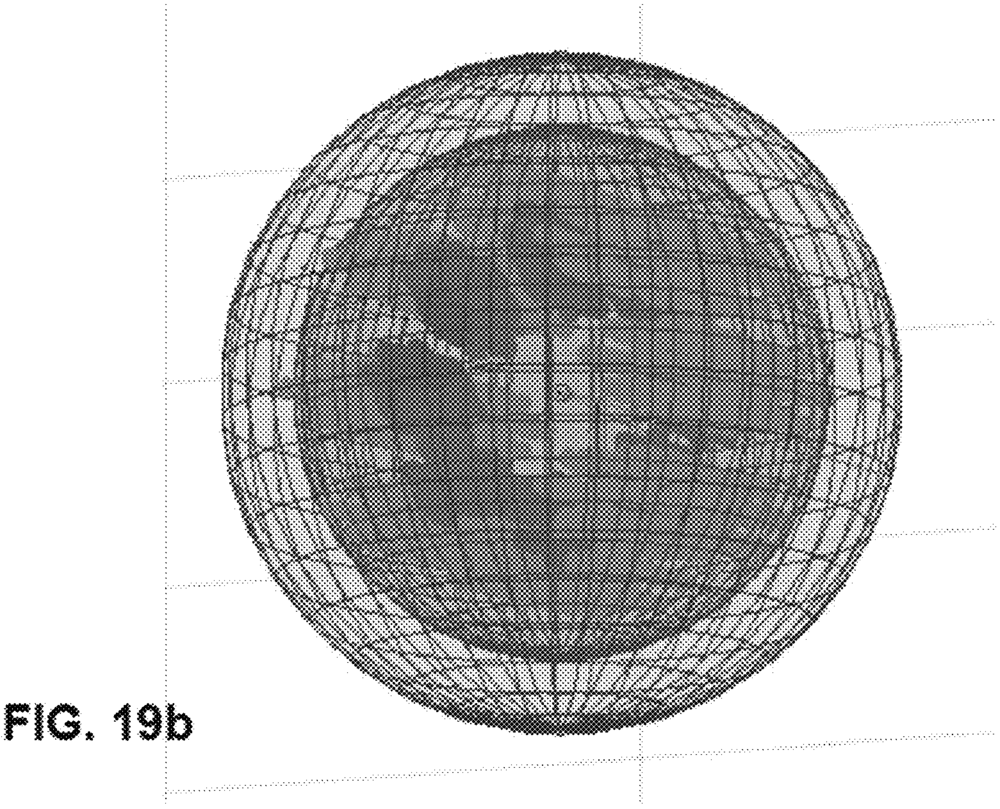
FIG. 19*b* depicts PtC (error cloud) and PtA (approximated error cloud) volumes at 60° at the $G_1$ side of the gap corresponding to FIG. 18*c*.

FIG. 19*b* shows PtC and PtA Volumes at 60° (FIG. 18*c*) showing the two approximation and point clouds on the $G_1$ side due to the two vector combinations.

The approximation is the extremes of the range and effectively reflects:

(1) the minimum gap size necessary for the arthroscope move through the knee joint safely; and (2) if the joint's anatomical limit has been reached.

Motion stereo in simulation measures the instrument gap with a mean of −0.0028 mm and standard deviation of 0.0096 mm. With the uncertainty introduced due to the image processing and arthroscope motion measurements, an instrument gap has a range of ±14% around the motion stereo measurement. Approximating the point cloud was found to increase the error range to ±16%, which is slightly worse than calculating the point cloud, but within the motion range of the joint to support knee arthroscopy instrument of 4 mm. These results are well within the accuracy range that can be achieved by surgeons or robots.

Measurement of the Instrument gap needs to be in real-time, whether it is to provide feedback to a surgeon or a robot manipulating the patient's leg. Calculating the point cloud, irrespective of the translation distance or direction, is too slow for real-time analysis. In comparison the approximation cloud takes on average 5 milliseconds—a fraction of the time to calculate the point cloud and well within limits for feedback to surgeons or robots.

For the approximation cloud calculations, 45° is the best angle, which align with the point cloud results, although the other angles are only slightly worse and both accuracy and processing speed acceptable. Changing the translation angle doesn't have a significant impact (maximum 0.169 mm) on the Instrument gap range or processing speed. Relative to the instrument size (diameter), the simulation gap size was set at 4 mm and when we take into account the uncertainty, the gap size range for the approximation cloud is −15.2% to 16.2%, and for the point cloud −13.91% to 14.03% as shown in Table II. The total uncertainty range for the approximation cloud is on average 1.3172 mm or 29% of the actual gap size, which in comparison is 2.2% more than the point cloud.

On a 4 mm instrument, larger range implies that the gap needs to be adjusted slightly larger to ensure the gap is at least 4 mm, however in reality a surgeon will need to adjust the gap as a minimum 4.5 mm but in most cases 5.5 mm to ensure they don't scrape the sides of the gap when navigating from a 2D image. For robotic systems the gap can be set smaller if the tolerance, but still needs to be relative to the arm's precision, which for most robots is also be in the millimeter range with the arm extended. In summary it is necessary to increase the gap of the lower side of the range until it is more than 4 mm to ensure the arthroscope can safely pass through, and on the high side check if the anatomical limits of the patient's joint are not exceeded.

Future technologies such as using deep learning might improve segmentation results or learn to more accurately measure the gap, however motion stereo, as discussed, accurately measures the gap and the approximation of the uncertainty of the segmentation and optical tracking errors are small relative to the 4 mm surgical instrument size, delivering an accurate real-time surgical applications.

The Inventors have succeeded in approximating the uncertainty point cloud and evaluating it for accuracy and processing performance against a point cloud solution. Approximations can be used effectively and in real-time for applications, including: Real-time measurement system inside the knee joint using a standard arthroscope; Minimal invasive surgery of other joints such as the shoulder; and other robotic measurement applications with single cameras, under water or in small spaces.

It has been demonstrated that using images from a standard arthroscope, the uncertainty can be approximated with a measurement accuracy similar to calculating the point cloud, however with a significant improvement in processing performance. The approximation of the uncertainty range can be used to in real-time for surgical applications to provide feedback to surgeons while moving surgical instruments through the knee joint or for the control of a robotic systems such as an automated leg manipulator. This study approximates the measurement uncertainty of the instrument gap range for small gaps including knee and other joint arthroscopy.

Compare the Measured Gap to Surgical Intended Size Boxes 71, 73 and 79

Once the gap has been measured, taking into account the approximated measurement uncertainties calculated at box 65, then at box 71 (FIG. 6) the processing assembly 126 compares the gap width d to the size of the surgical instrument (stored in box 73) that is intended to be used in the gap. If the gap is sufficiently large, then control diverts back to box 53 and more images from the arthroscope 40 are imported and processed until the processing assembly 126 decides at box 71 that the gap is not large enough for the surgical instrument. In that case control diverts to box 79 where a procedure to set a new leg pose is implemented. The procedure to set a new leg pose adjusts the angle of the femur and tibia (or other adjacent bones for other joints) in order to adjust the knee gap to a desired width without exceeding a natural limit of the joint, which would be damaging.

For minimal invasive surgery such as an arthroscopy, surgeons physically position and restrict parts of the patient's leg in the coronal, sagittal or transverse planes to allow surgical equipment to reach specific positions inside the body. For knee replacements without robotic support, they manually align the femur and tibia with varying accuracy levels that depends on experience. To control the nine Degrees of Freedom (DoF) of the combined hip and knee motion it is necessary to estimate the poses of these joints in real-time accurately.

Figure 20A:
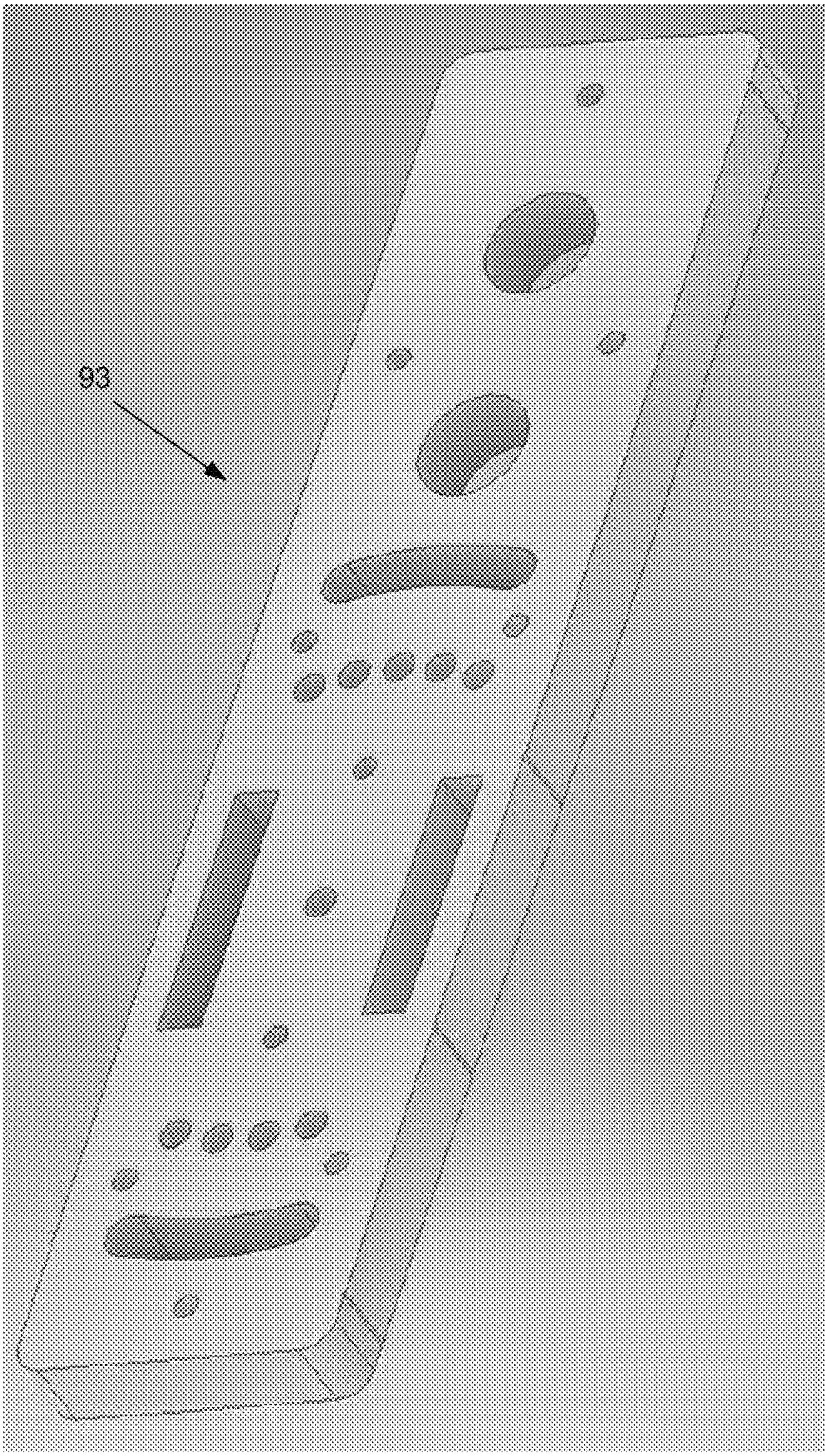
FIG. 20*a* is a view of a rigid body in the form of a mounting plate for attachment of markers and for mounting to a leg.
Figure 20B:
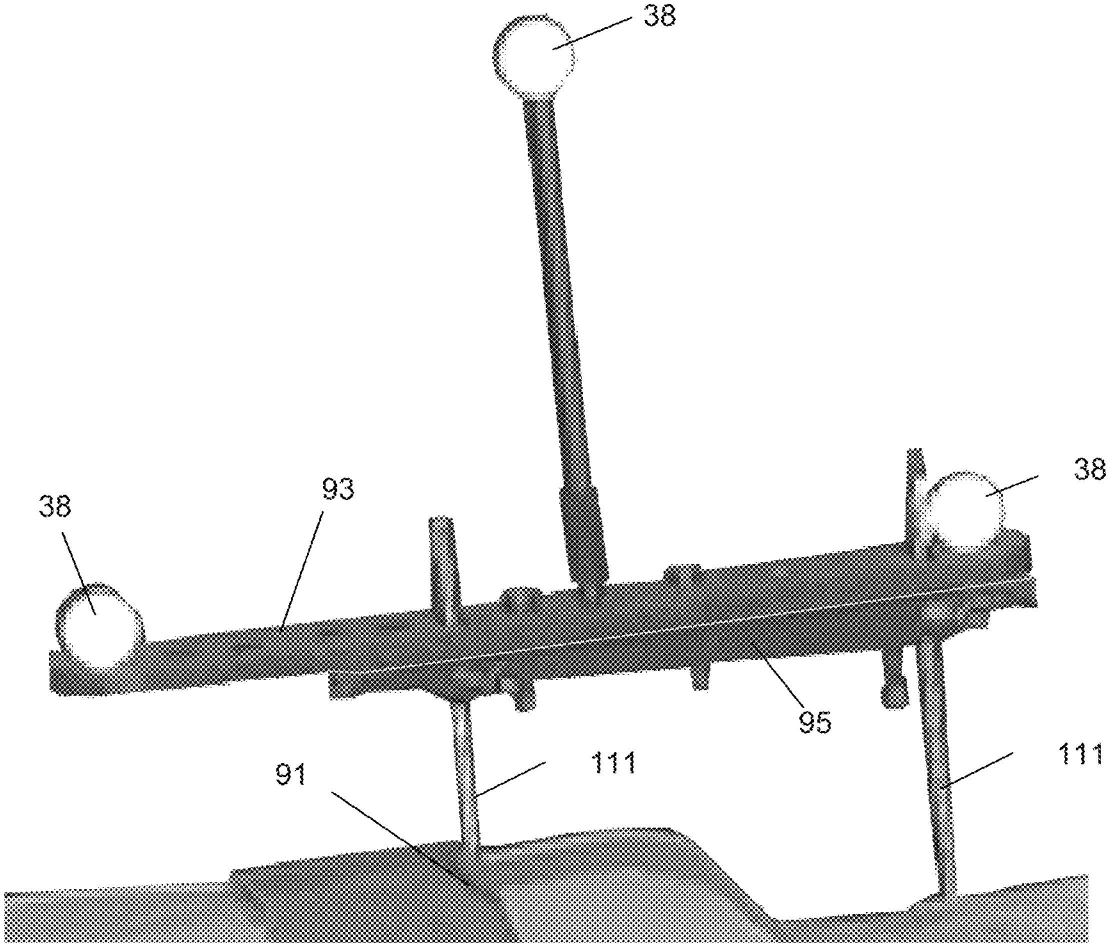
FIG. 20*b* is a view of the mounting plate shown position-adjustable mounted to a base plate, the base plate being attached to a bone of the leg with surgical pins.

As can be seen in FIG. 1, in one embodiment leg mounted rigid bodies (RB) 93 with markers (optical tracking balls) 40 in specific positions are mounted on the patient's leg 91 to both the tibia and femur and to the footplate of the first robotic arm. FIG. 20*b* shows the rigid body 93 mounted to the tibia. RB 93 mounts to, and is positionally adjustable relative to, a base plate 95 that is fastened to the bone with surgical pins 97. As may be seen in FIG. 22*b* the position of the markers 38 relative to a point inside the leg 91 is measured using an imaging procedure such as Computed Tomography (CT) scans of the leg accurately image the rigid bodies 93. The leg pose, i.e. the angles of the leg bones relative to each other is calculated by processing assembly 126 using tracking data acquired from cameras 50 which image the markers 38, and, in some embodiments, from local measurements, for example positional feedback from one or more actuators 42 of the surgical joint positioning apparatus 100 via controller 200 which is in data communication with processing assembly 126. Processing assembly 126 may also reference database 25 which stores the CAT scan positional data.

Figure 20C:
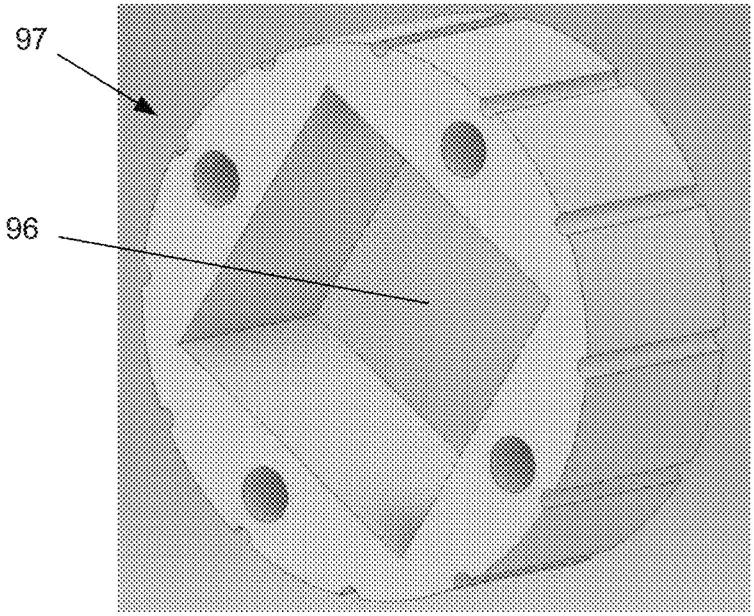
FIG. 20*c* is a view of a rigid body in the form of a cylinder with a lumen therethrough for mounting about a body portion of an arthroscope.
Figure 20D:
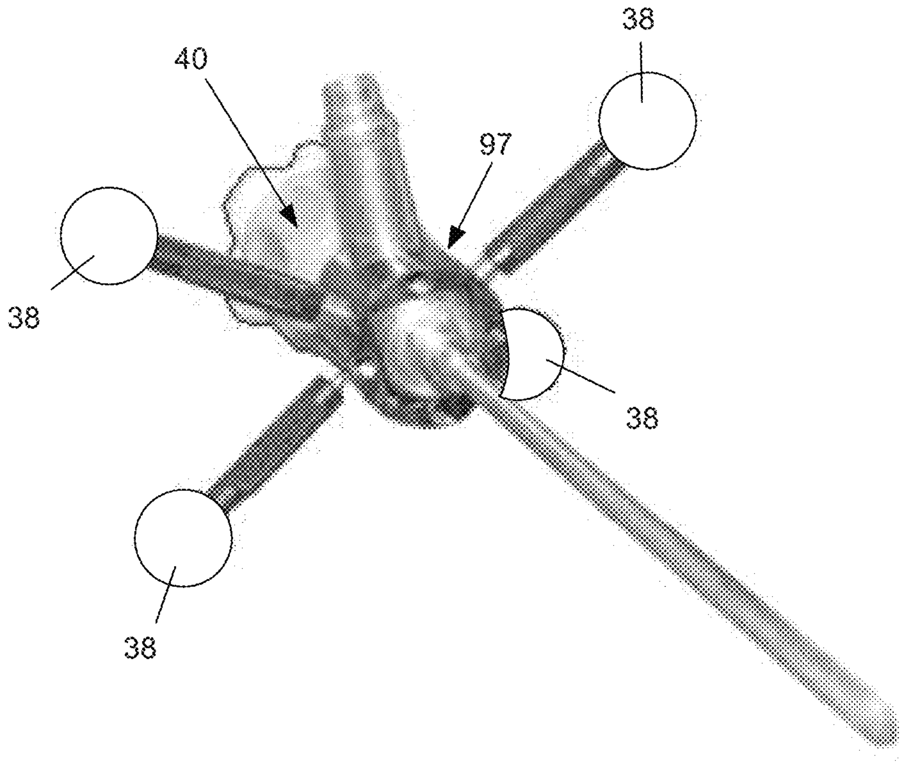
FIG. 20*d* shows an arthroscope with the rigid body of FIG. 20*c* attached thereto and with markers fastened to the rigid body.

In order to track the position of the arthroscope 40, an arthroscope mountable rigid body 97 is provided as depicted in FIG. 20*c* which fits onto the arthroscope 40 as shown in FIG. 20*d* with markers 38 attached thereto.

Figure 21:
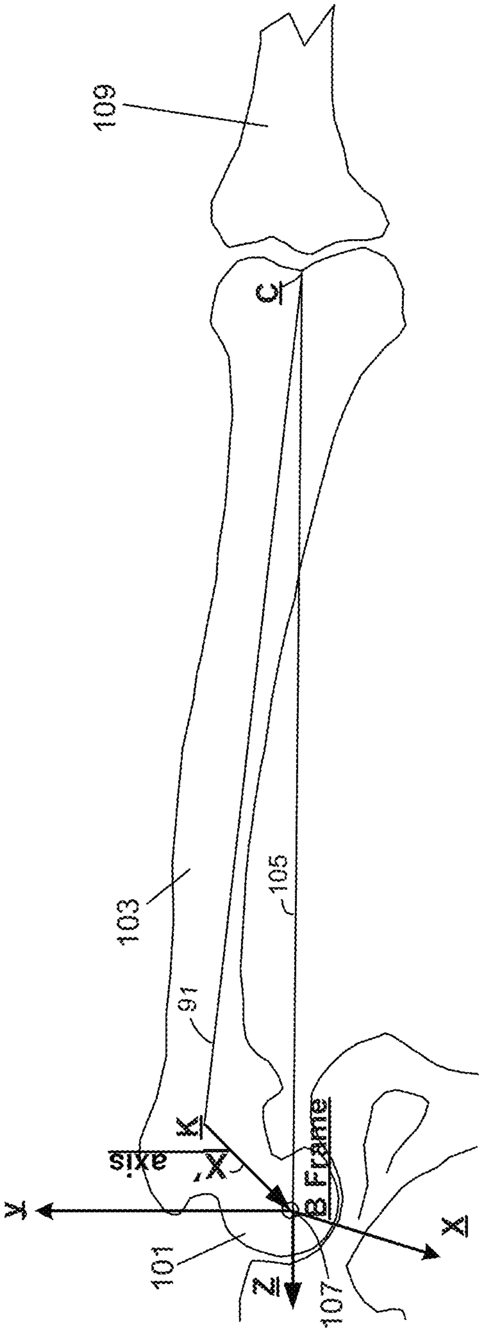
FIG. 21 is a diagram illustrating a “B frame” being a rectangular axis system set up on the femoral mechanical axis (FMA) using ball joint to femur (point K) to determine the frame’s x and y axes.

As illustrated in FIG. 21 (and in the marked-up CAT scan of FIG. 24*a*), the femur anatomical axis 91 follows the femoral head 101 and femur 103 structures, while the femoral mechanical axis 105 (FMA) is the axis that links the hip ball joint center 107 to the center of the condyles C on the knee. The FMA 105 determines the hip to knee joint motion, even though tracking devices are mounted to the femur.

For automation and to minimize interference in the surgical area, the subject's leg may be moved robotically by applying force to the heel as shown in FIG. 1 by robotic arm 16. Marker data from the rigid bodies 93 mounted on the femur 103 and tibia 109, together with CT scans of the leg 91, stored in database 25, are used by the processing assembly 126 as configured by software 27 to determine positions relative to the anatomy of the leg 91.

The Inventors considered the following criteria for optimal rigid body designs and marker setup:

I. Maximize marker visibility during an arthroscopy
II. Markers from OptiTrack need to fit the RBs
III. No damage to RBs due to surgery
IV. Fit to existing surgical pins and instruments
V. Optimal size, material and shape
VI. The system needs to have a positional accuracy in the sub-millimeter range locally and across joints
VII. Support setup of dynamic (real-time) frames A. Femur and Tibia Rigid Bodies From experimental trials on artificial and cadaver legs and joints, various rigid bodies were developed for mounting markers to both the femur and the tibia. As previously mentioned, FIG. 20*a* is a view of a rigid body (RB) marker plate 93 which may be sized to fit on either the tibia 109 or the femur 103 and which does not interfere with surgical manipulation. The RB marker plate 93 for the femur or tibia has a limited (5 mm) adjustment when mounted, to allow alignment on the leg. A mounting base (baseplate) 95 is attached to the surgical 111 pins with the RB marker plate 93 that fits on the base plate 95, as shown in FIG. 20*b*. The marker plate 93 adjusts relative to the base plate 95 in all directions relative to the leg 91. Once the markers 38 are installed on the plate 93, it forms a rigid body that can be tracked in real-time via cameras 50 of sensing system 152 to support analysis of leg motion. Mounting the rigid body 93 with markers 38 on the femur 103 or tibia 109 requires the use of surgical pins 111 and drilling two of them through into the femur and tibia bones to ensure a solid fixture. The Inventors added markers 38 on the robot boot 14 (i.e. leg holder 14), that is rigid relative to the tibia, which can be used instead of the tibia RB to track positions in the lower leg or foot. The results that are set out later are for an RB attached to the tibia.

Tracking of surgical camera/instruments is significant for autonomous navigation, monocular measurements or 3D reconstruction of the cavity. The design of the arthroscope rigid body 97 (FIGS. 20*c* and 20*d*) is based on experimenting with standard OptiTrack RBs during cadaver surgeries and improving on rigidity, size and placement of the markers for continuous tracking during surgery. The rigid body on the arthroscope has a square lumen 96, as shown in FIG. 20*c* that tightly fits onto the arthroscope 40. The markers 38 are positioned on arthroscope 40 such that they do not obstruct the motion of the instrument or interfere with the surgeon.

The optical volume setup determines the tracking accuracy. To effectively reconstruct the RB layout (if some markers are occluded) at least three markers 38 (which can be different markers over time) need to be visible from three of the cameras 50 at all times, irrespective of staff and equipment placing. Marker and RB layout can increase visibility, however increasing the number of cameras 50 achieves a higher accuracy for marker location, and more markers can be tracked during surgical manoeuvres.

Figure 22A:
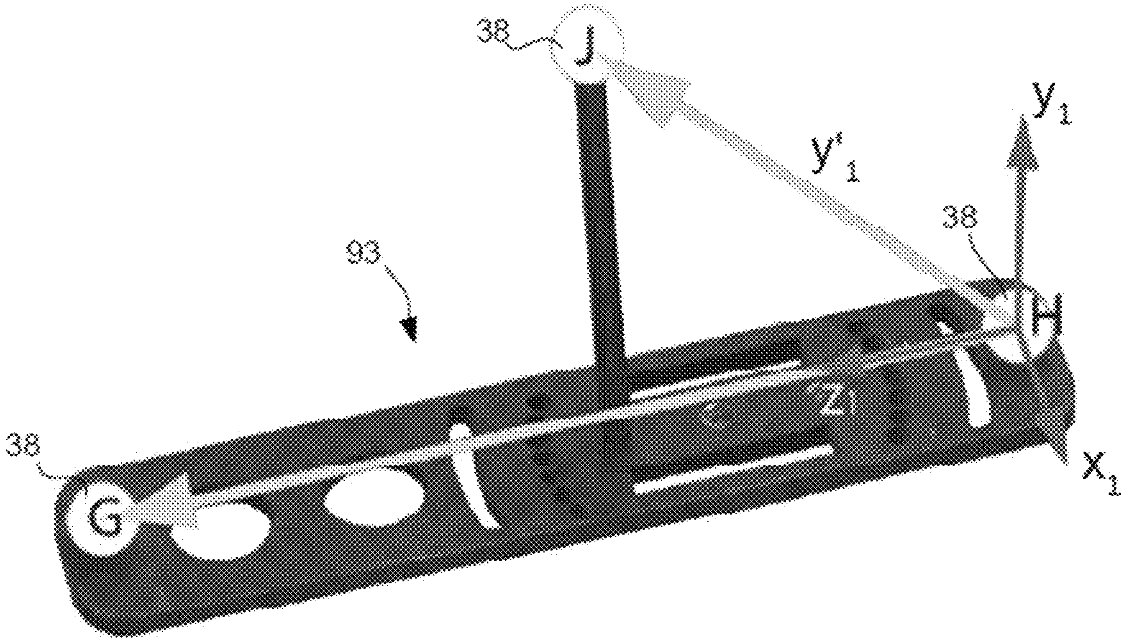
FIG. 22*a* shows markers H, J and G on a femur rigid body RB1 where marker G is for placement closest to the body and H is for placement near the knee.

In order to estimate poses of any chosen point on or inside the leg 91, it is necessary to setup coordinate frames on key position of a rigid body 93 as illustrated in FIG. 22*a*, mounted on the leg 91. In knowing the position of the optical markers 38 with respect to the sensing system 152 global frame (W) and the CT images (e.g. FIG. 22*b*), it is possible to calculate the local transformation between the RBs and points on the leg 91 to provide for the retrieval of the pose of any position on the leg with respect to the global frame (W). Calculus behind the described concept will now be formulated and leg joint angle calculated to demonstrate its use in practice.

A. Marker Coordinate Frames

Instrument and leg pose analysis requires the setup of frames from marker information measured during optical tracking, using the rigid body designs that have been described. The axis for the analysis uses a y-up right-hand coordinate system to align for the optical tracking system configuration, as shown on marker H in FIG. 22*a*.

The generalized homogeneous transformation matrix (using notations as detailed in [19]—P. Corke, *Robotics, vision and control: fundamental algorithms in MATLAB*. Berlin: Springer 2011, vol. 73, no. Book, Whole) of the marker G coordinate frame, relative to the origin (or pose of frame H relative to frame W—see FIG. 23) is $T_H$ as expressed in FIG. 36F, where x, y and z (first three columns) are the local frame axes on the rigid body at point H and i, j and k the unit vector axes of the global frame (W). For a frame on marker H (RB1 in FIG. 23), the axes for the transformation matrix (T) can be calculated directly from the rigid body using marker combinations to create vectors between points that align with the rigid body as shown in FIG. 22*a:*

1) The RB1 z-axis ($z_i$, $z_j$, $z_k$) is a unity vector from H to G
2) The frame x-axis ($x_i$, $x_j$, $x_k$) is: x=y'×z
3) The y-axis ($y_i$, $y_j$, $y_k$) is: y=z×x
4) The position vector (${}^wh_i$, ${}^wh_j$, ${}^wh_k$) is the marker position relative to W.

Using the homogeneous matrix (30), it is possible to setup frames on any of the markers of any rigid body. For example, the transformation $T_B$ defines the pose of a frame on an anatomical point on the femur (B) relative to the world frame (W).

B. Local Transformations

Figure 22B:
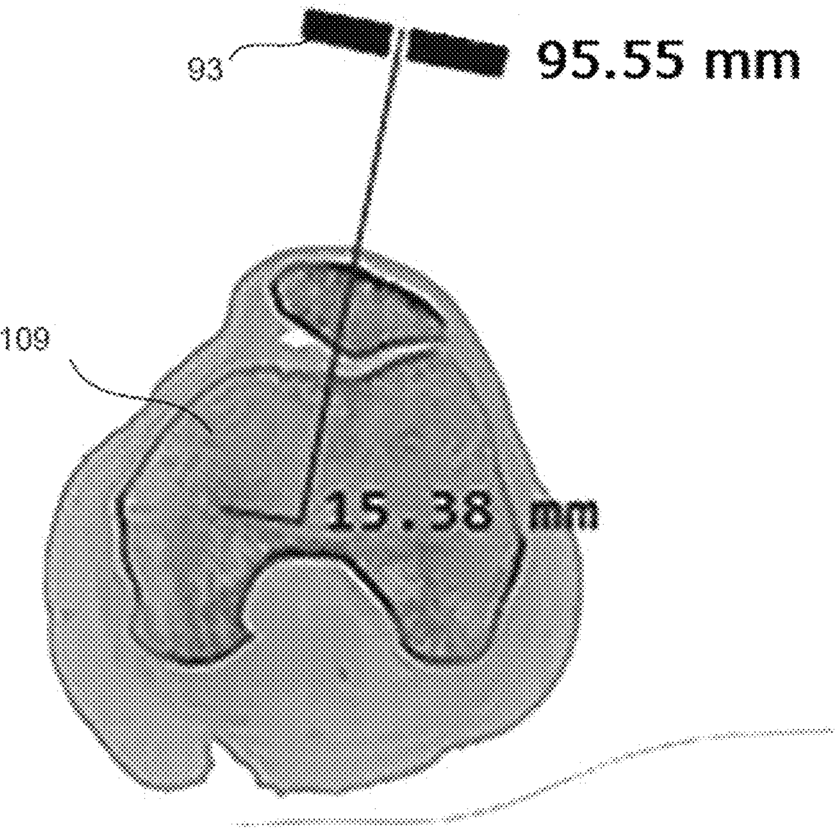
FIG. 22*b* is a color inverted CT scan slice a femoral head with measurements from the rigid body RB1.
Figure 23:
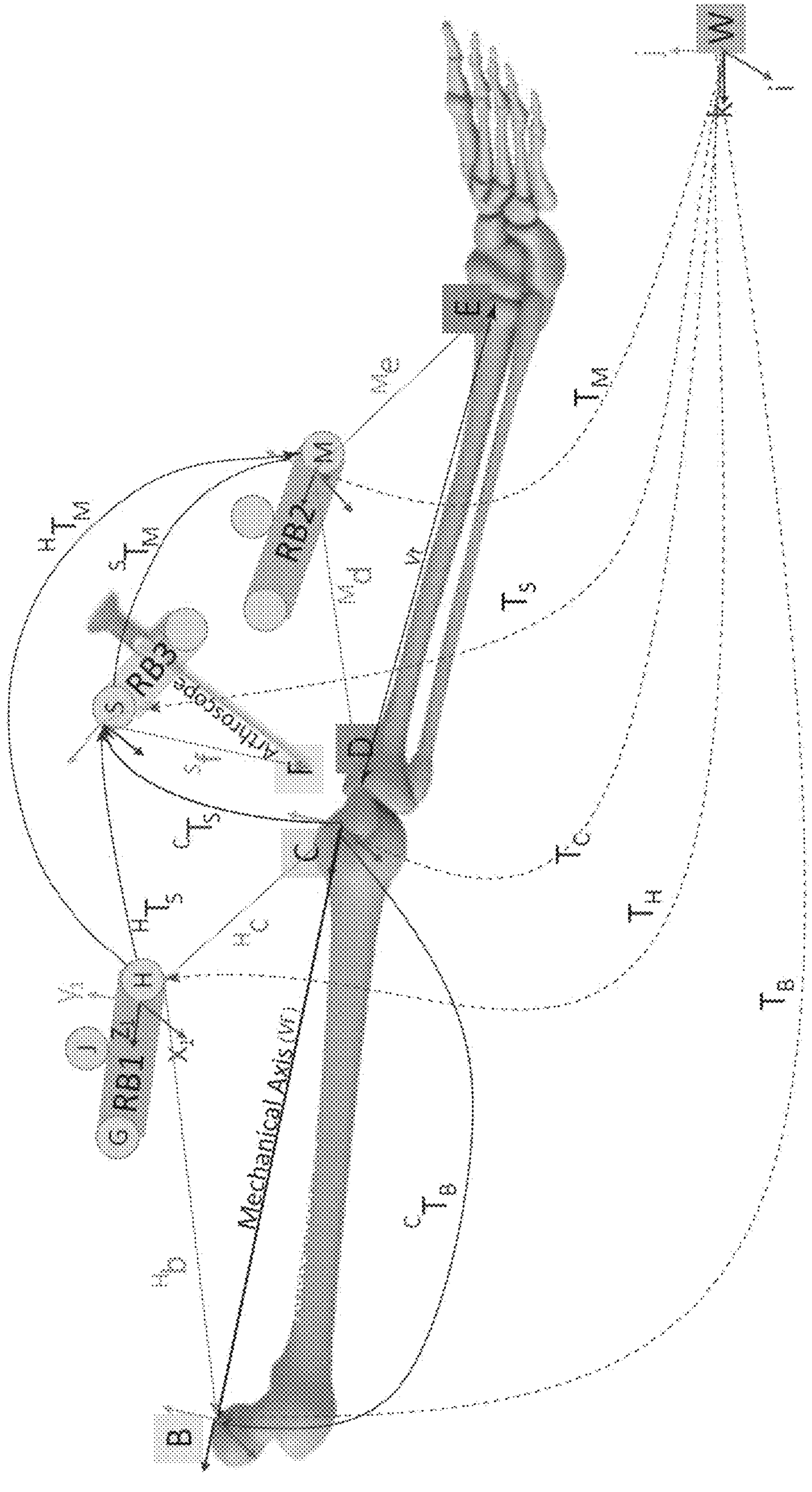
FIG. 23 is a diagram indicating transformations and vectors on the human leg for arthroscopy.

A CT scan of the leg is essential to determine the vectors for any point of the leg with respect to one of the marker frames. It is beneficial to perform the CT scan in various positions to enable measurements of different points of the leg as shown in FIG. 22*b*, where the measurements were taken for the local translation from RB1 to the center of the femoral head. FIG. 21 shows the femur and the relationship between the mechanical and anatomical axes of rotation of the femur relative to the hip. Using dynamic frames on the leg, we can determine any positions on the leg or arthroscope at any point in time, and relative to a specific frame. For instance, point C (or vector from W to C) on the leg relative to W is we as expressed in FIG. 36G, where ${}^Hc$ is the local translation (vector) from frame H on RB1 to C on the leg as depicted in FIG. 23.

C. Transformations Between Legs and Instruments Coordinate Frames

The transformation between rigid bodies can be determined from the relationship between frames on the RBs or leg. As an example, for the transformation from frame M to frame H can be expressed as shown in FIG. 36H. Any point on the tibia in frame M can thus be expressed relative to frame H on the femur. Significantly, the Inventors have found that it is possible to express any point relative to any frame, even across joints.

D. Arthroscope Tip Position

To know in real-time the arthroscope tip position in the femur C frame (${}^Cf$) we observe from FIG. 23 the equation as shown in FIG. 36I.

E. Motion Analysis

A surgery is performed with the patient lying on their back and thus the Inventors choose y-up and z aligned along the body from toe to head. Using the transformations described above, we define vectors between points on the bones, from which knee and hip joint rotations and translations are analysed.

1) Knee Angles:

The tibia vector is defined from the center of the condyles to the ankle center. However, the motion of the tibia is relative to the femur (rotations and translations) and needs to be measured relative to a frame on the femoral condyle center. The rotational matrix on the condyle can be setup using measurements using the CT scan data as shown in FIG. 21. As illustrated, we determine the center of the ball joint (B) and the connection center (K) of the femoral anatomical and femoral head axes. This vector forms the x' axis and we obtain the expressions as shown in FIG. 36J.

The zx' plane is defined by points B, K and C in FIG. 21 with y perpendicular to this plane. The rotational frame (${}^WR_B$) on the FMA is the combination of the x, y and z vectors on point B. For rotations or translations of the tibia relative to the femur, the transformation frame in point C, on the femoral mechanical axis is expressed as shown in FIG. 36K, where ${}^wc_B$ is point C in W via frame B. The vector from the center of frame $T_C$ to point E describes the motion of the tibial mechanical axis, which is: $v_t={}^Ce_M$ (Tibia Vector).

In kinematics the angles of the hip and knee joints are extensively used and is essential for future robotic applications. For this study we will use the rigid body system to calculate the joint angles and use synchronized video from the sensing system 152 to visually compare the results. Using vector analysis, the knee varus (β) and flexion (α) angles can be calculated as expressed in FIG. 36L, where $v_{t_x}$ is the projected $v_t$ vector on the unity vector ($x_n$) of the femur C frame's x-axis and $v_{t_{yz}}$ the $v_t$ vector in the yz-plane. Using these vectors, we can calculate the dot and cross product between $v_{t_{yz}}$ and $v_t$, with the knee varus angle β as expressed in FIG. 36M. Projecting $v_t$ to the xz plane, the knee flexion angle α can be expressed as shown in FIG. 36N.

Using a rotational matrix is an alternative option of calculating the knee angles between vectors $v_f$ and $v_t$. The rotational matrix ${}^{vf}R_{vt}$ between the femur and tibia can be expressed as shown in FIG. 36O, where $t_r=v_f+v_t$. Using the matrix, the knee IE angle γ can be expressed as shown in FIG. 36P.

Knee Translations:

During minimally invasive surgery, the knee gap size between the femur and tibia is required for accessing inner knee areas with surgical instruments. Translations in the joints can be measured by setting up vectors at the condyle joint points C and D, that is using point D in frame C (see Section IV-D). ${}^Cd$ will provide the x (medial/lateral), y (posterior/anterior) and z (knee gap) translation of the knee joint as a result of rotation and translation during motion.

Figure 24A:
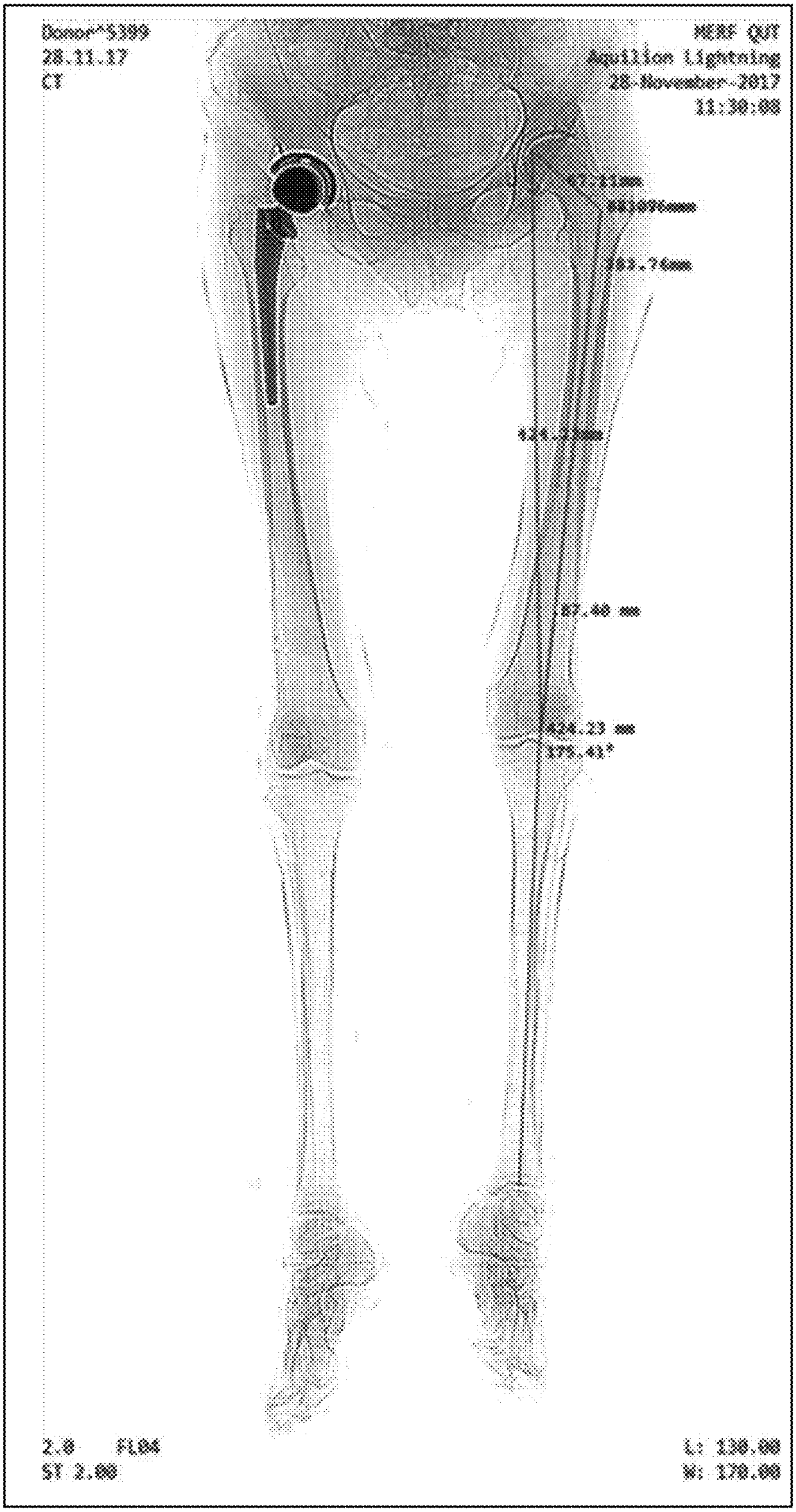
FIG. 24*a* is an inverted-color CT scan of a human leg showing femur anatomical and mechanical axes similarly to those of FIG. 21.

Hip Angles:

The femur mechanical axis is defined as the link from the hip joint center to the center of the condyles on the knee as shown in FIGS. 21 and 24*a*. The femur vector that describes the hip rotations relative to the world frame is: $v_f={}^Bc-{}^Bb$ (Femur Vector). Angles and translations are measured relative to the sagittal (flexion), coronal (varus) and transverse (knee gap) planes. Using vectors, the hip varus (ψ) and flexion (θ) angles are respectively expressed in FIG. 36Q.

For the hip roll angle, we can project $v_{f\,to}$ the yx plane and calculate the angle between the plane and ${}^vf_{yx}$. However, we can also use rotational matrices. Using ${}^WR_C$(33) we get the hip roll angle ψ as expressed in FIG. 36R.

V. EXPERIMENTAL VALIDATION

A. Experimental Setup

Figure 24B:
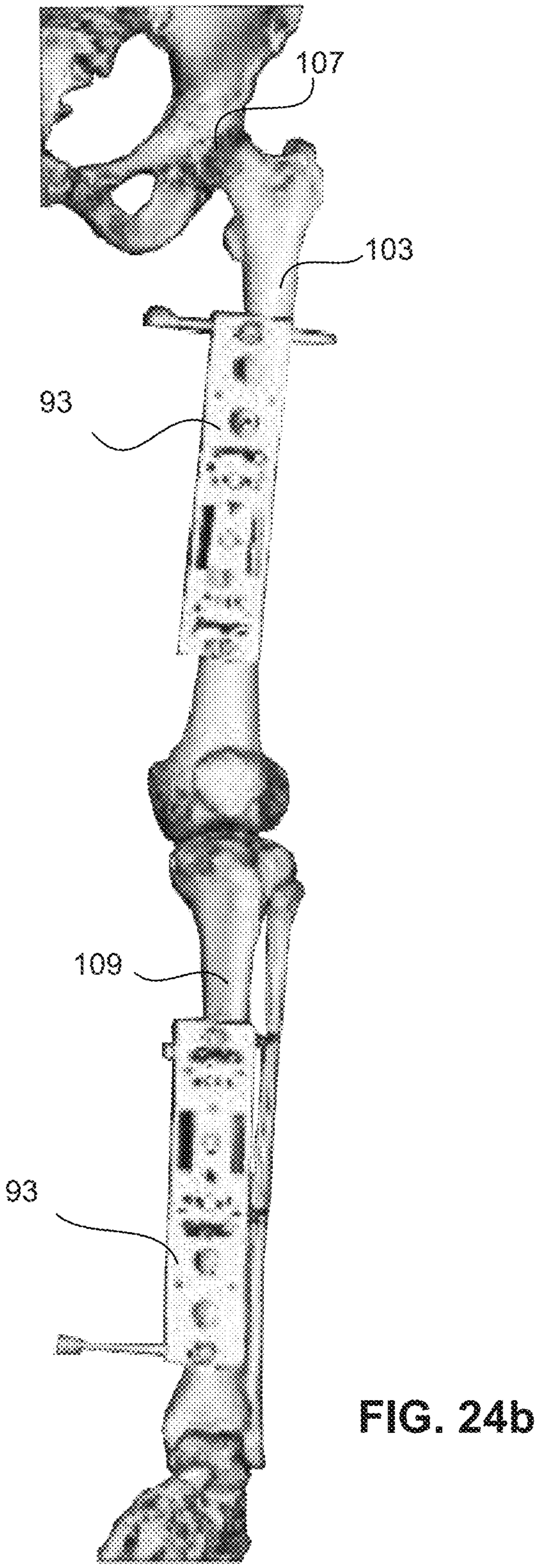
FIG. 24*b* is a CT scan of a human leg with rigid bodies (RBs) mounted thereto.
Figure 25A:
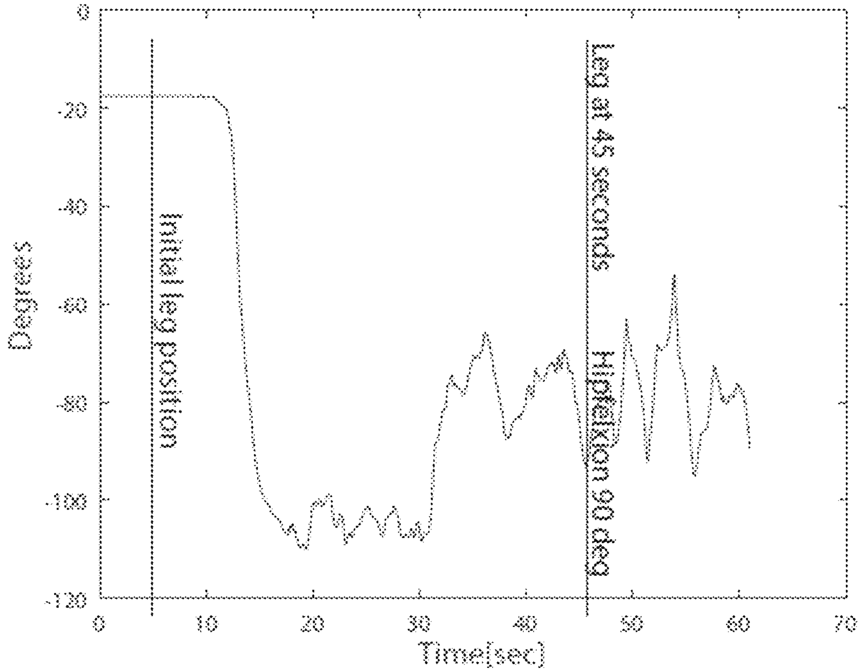
FIG. 25*a* is a graph of hip flexion measured using a sensing assembly versus time for a sixty second period.
Figure 25B:
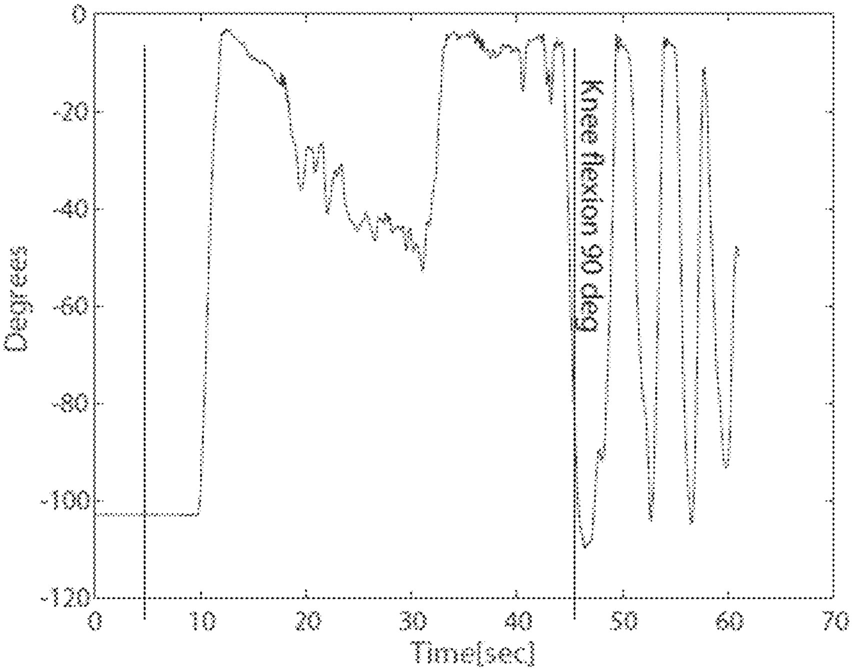
FIG. 25*b* is a graph of knee flexion measured using a sensing assembly versus time for a sixty second period.
Figure 25C:
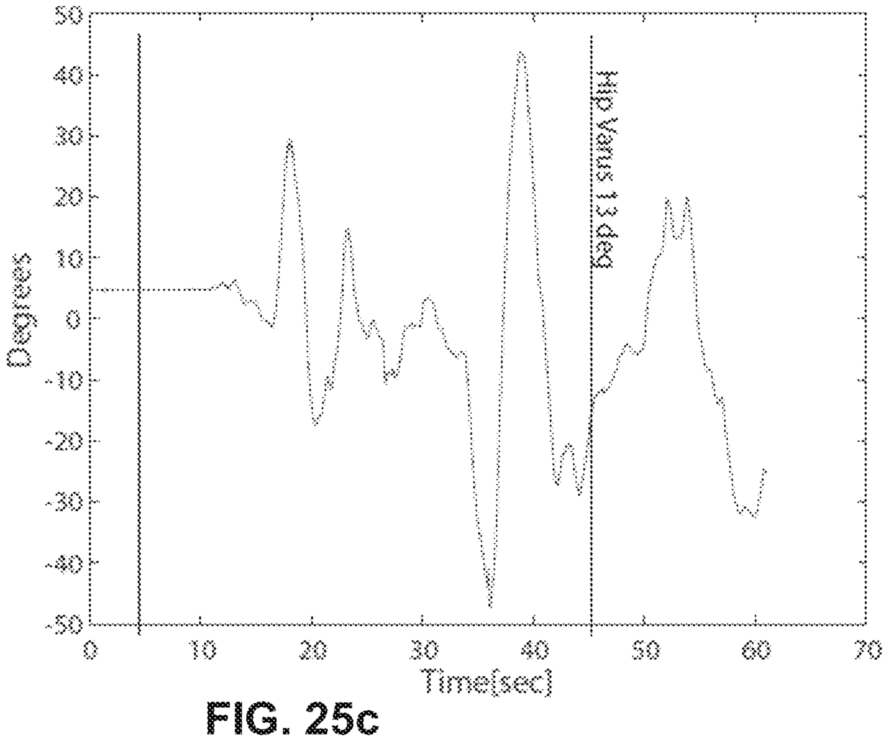
FIG. 25*c* is a graph of hip varus angle measured using a sensing assembly versus time for a sixty second period.
Figure 25D:
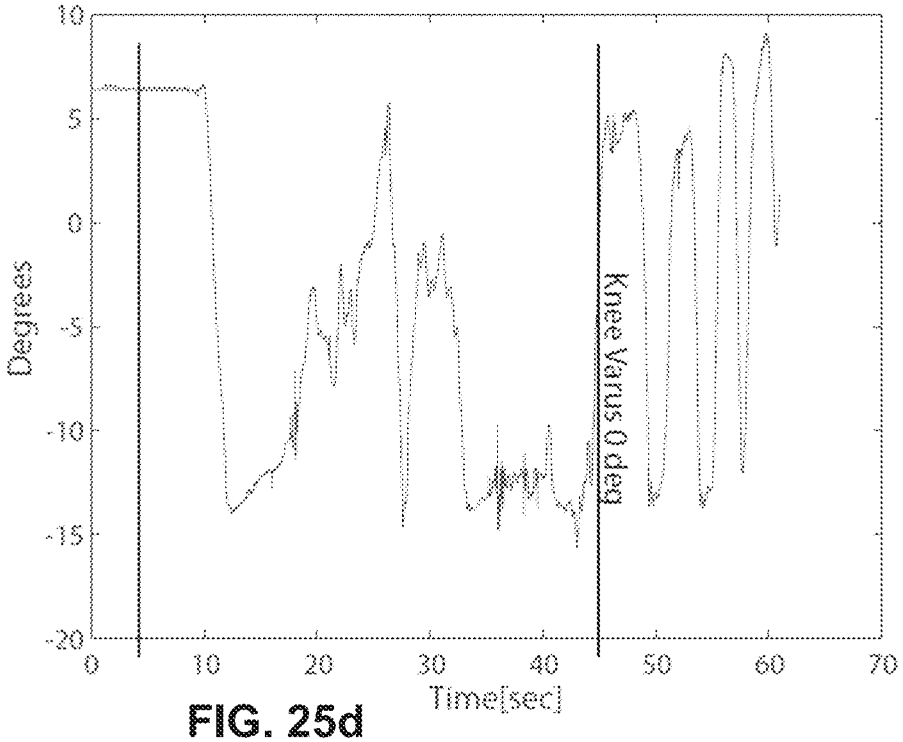
FIG. 25*d* is a graph of knee varus angle measured using a sensing assembly versus time for a sixty second period.

The leg manipulator robot 100 was tested using cadaver legs. Ethical approvals were gained for three cadaver experiments as detailed in Table 6. Firstly, the robustness and accuracy of existing rigid bodies from OptiTrack were tested. An overhead ten camera system was installed on a 3 m×3 m×2.5 m structure (somewhat as illustrated in FIG. 19*c*) and calibrated with an accuracy wand. The second experiment tested the designed RBs and CT scan measurements as shown in FIGS. 24*a* and 24*b*, which are CT scans of a cadaver leg showing femur anatomical mounted RBs mechanical axes and markers.

TABLE 6

Cadaver experiments to test standard rigid bodies from OptiTrack, the newly designed rigid bodies as well as the leg motion.

| Experiment | Cadaver | Sex | Age |
|---|---|---|---|
| OptiTrack Std RB | Left and Right Knees | Male | 80-90 |
| Designed RBs | Left and Right Knees | Male | 60-70 |
| Kinematic Tests | Left and Right Knees | Female | 50-60 |

A 4 mm Stryker arthroscope was used as the image capture apparatus and an OptiTrack System was used as the sensing system during the experiments. The designed RBs were mounted on the cadaver femur, tibia, arthroscope and robot boot. Markers were mounted in for real-time visibility and frame setup.

B. Experimental Results

OptiTrack results show that there is continuous visibility of the markers during a full leg motion experiment of 4 minutes. Enough markers were tracked on each RB for the OptiTrack system to fully recover the position of each marker.

Table 7, as illustrated in FIG. 36S, shows point E relative to the world frame ($\omega_{eM}$) vial local translation from M to point E and then a translation via frame C and M to point E ($\omega_{eB^M}$). Table 8, as shown in FIG. 36T, illustrates local Translation Error length with $\omega_{eD}$ via frame D, compared to $\omega_{eC}$ which is via frame C.

Leg angles as shown in FIGS. 25*a*-25*d* were calculated from the measured marker positions during cadaver experiments. The graphs in FIGS. 25*a*-25*d* show the first sixty seconds of a five-minute cadaver experiment. The leg was tracked using the designed optical rigid bodies. The leg was moved through a range of angles, manually and with the leg manipulator robot.

Providing autonomy for leg positioning and surgical instrument navigation in robotic-assisted orthopaedic surgery requires accurate spatial information. Prior to cadaver experiments, CT scans of the leg were taken and then using the OptiTrack system, marker data was recorded by moving the legs through all possible ranges for leg surgeries. The standard OptiTrack rigid bodies were initially tested and failed physically within a few minutes during the first cadaver arthroscopy. Markers were easily obstructed due to surgeon, staff, patient and instruments motion and manually setting up of frames on specific markers difficult. Rigid body pose data provided by the OptiTrack system is not accurate for multiple leg and instrument tracking, as it relies on manually initialising the rigid bodies with the world frame setup during calibration.

For a knee arthroscopy, millimeter accuracy is required for measurement of the internal joint parameter such as the size of the knee joint gap needed for the 4 mm arthroscope to pass through it. Surgeons regularly overestimate the gap resulting in unintended damage. From testing, the OptiTrack accuracy was found to be 0.03 mm when measured over 33000 samples in dynamic surgical conditions and similar to that reported by Maletsky [12]. The positional accuracy of the OptiTrack and the custom rigid bodies for each part of the leg and instruments, ensure real-time data reliability during the surgery. It supports an accurate setup of frames to track points on the leg or instruments. The accuracy of local points on the leg is dependent on the accuracy of the combination of the OptiTrack and CT scan measurements. With CT scan measurement accuracy of 0.3 mm [15], the accuracy of a point in the leg is largely dependent on that.

As shown in Table 8, the overall accuracy crossing two local measurements is on average 0.75 mm, aligning with the CT scan accuracy, which is small relative to sizes in the knee joint and negligible when calculating parameters such as joint angles.

The volume setup of the optical system is important for visibility. In the presently discussed embodiment at least three markers on an RB need to be visible to know all marker positions. It was found that for an arthroscopy ten cameras placed above and at the sides of the volume, ensured continuous optical marker tracking, irrespective of surgeon or instrument motion. For automated leg manipulation or future robotic surgery, movement around the patient is reduced, and fewer cameras and a smaller volume will be required. The optical tracking accuracy of markers on the leg using the mathematical model is shown in table 7, where the ankle center point (E) is tracked across RBs, showing consistent positional information for the ankle. The combination of CT and optical tracking shows that during surgery, it is possible to accurately and in real-time translate to points across joints and express points in a joint relative to any frame. For other areas of the body or for different surgeries, it is necessary to customize the RBs. However, the measurement and mathematical approach remain the same.

Key parameters for robotic leg manipulation include the rotations and translations of each joint, which is calculated from the combination of CT, optical tracking and the mathematical model. It forms an integrated system during surgery for real-time anatomical measurements. Angles for each joint were calculated from the cadaver data and are shown in FIGS. 25*a* to 25*d*. For clarity, only the first 60 seconds are shown. The accuracy of the vector's positional data (0.3 mm), ensures that the calculated angles are accurate.

For knee surgery, the dynamic space in the knee joint and an arthroscope diameter of 4 mm, make the submillimeter accuracy that has been described suitable for robotic leg manipulation and instrument guidance. Other applications include modelling of the joint surfaces and structures and alignment of femur and tibia axes.

During three cadaver experiments, the leg was moved through surgical positions to provide the full motion ranges for the hip and knee joints. The system was verified by translating to known markers across joints. The rotations of the hip and knee joints are calculated, with an accuracy relative to the accuracy of the positional data of the mechanical vectors, which is 0.3 mm. To reduce patient trauma the foot rigid body can be used to analyse point in the tibia. The cadaveric experiments were approved by the ANHMRC Committee No. EC00171, approval no. 1400000856.

Figure 26:
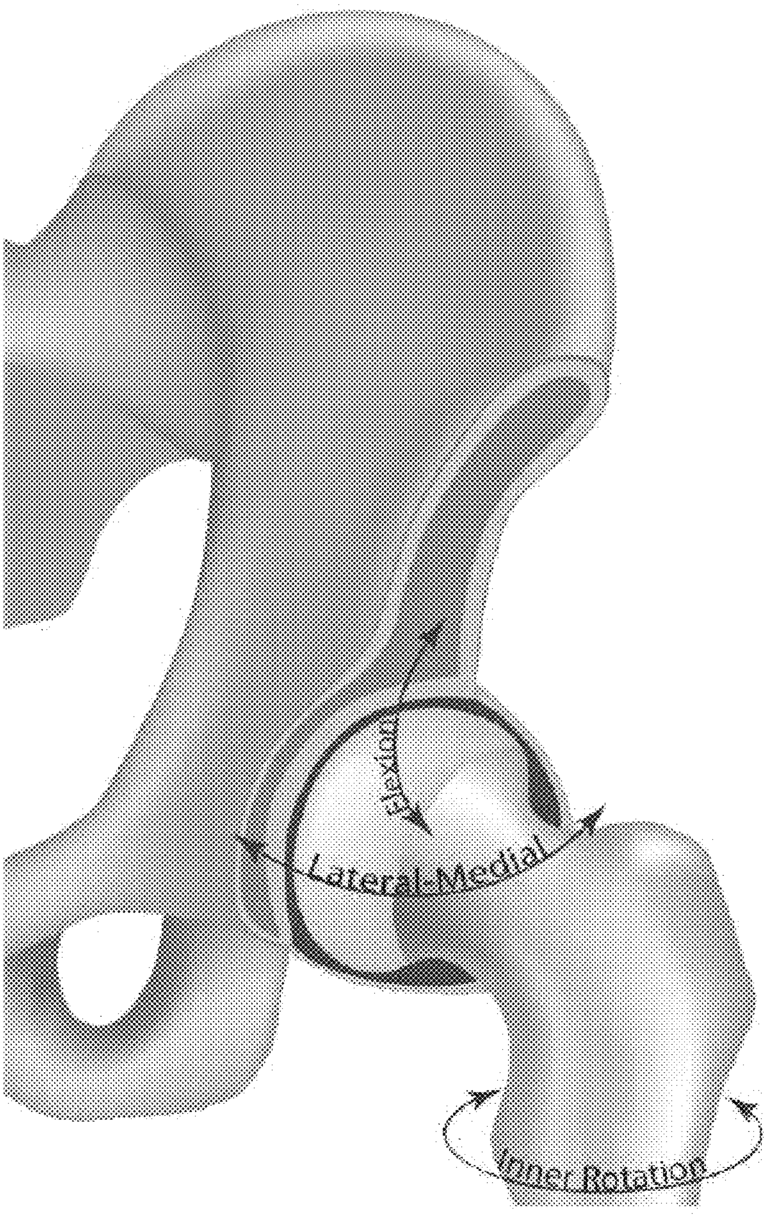
FIG. 26 is a diagram illustrating three degrees of freedom (DOFs) of the hip.

To develop a robotic model of the human leg it is imperative to understand the motion of both the hip and knee joints. The hip is a ball and socket joint with three DOF [6] and as detailed in FIG. 26, can be modelled using three revolute joints. Apkarian et al. noticed that the hip joint leads through the femur head onto the femur with an offset (femoral neck), changing the rotational properties to extent the motion capabilities of the human's hip kinematic range [7], Inner rotation of the ball joint (including femoral head) in the sagittal plane is equivalent to hip flexion. It is the main motion during walking and has the largest range of the hip joint motion [11] and is only restricted by surrounding muscles, tendons and nerves. Anterior/exterior motion of the hip ball joint in the transverse plan results in femur internal and external rotation and is limited by the ball configuration in the hip [12]. Varus or valgus forces on the leg (or femur) rotates the hip joint proximal or distal, resulting in a medial or lateral translation (Abduction/Adduction rotation) of the hip ball joint in the coronal plane [7].

Figure 27:
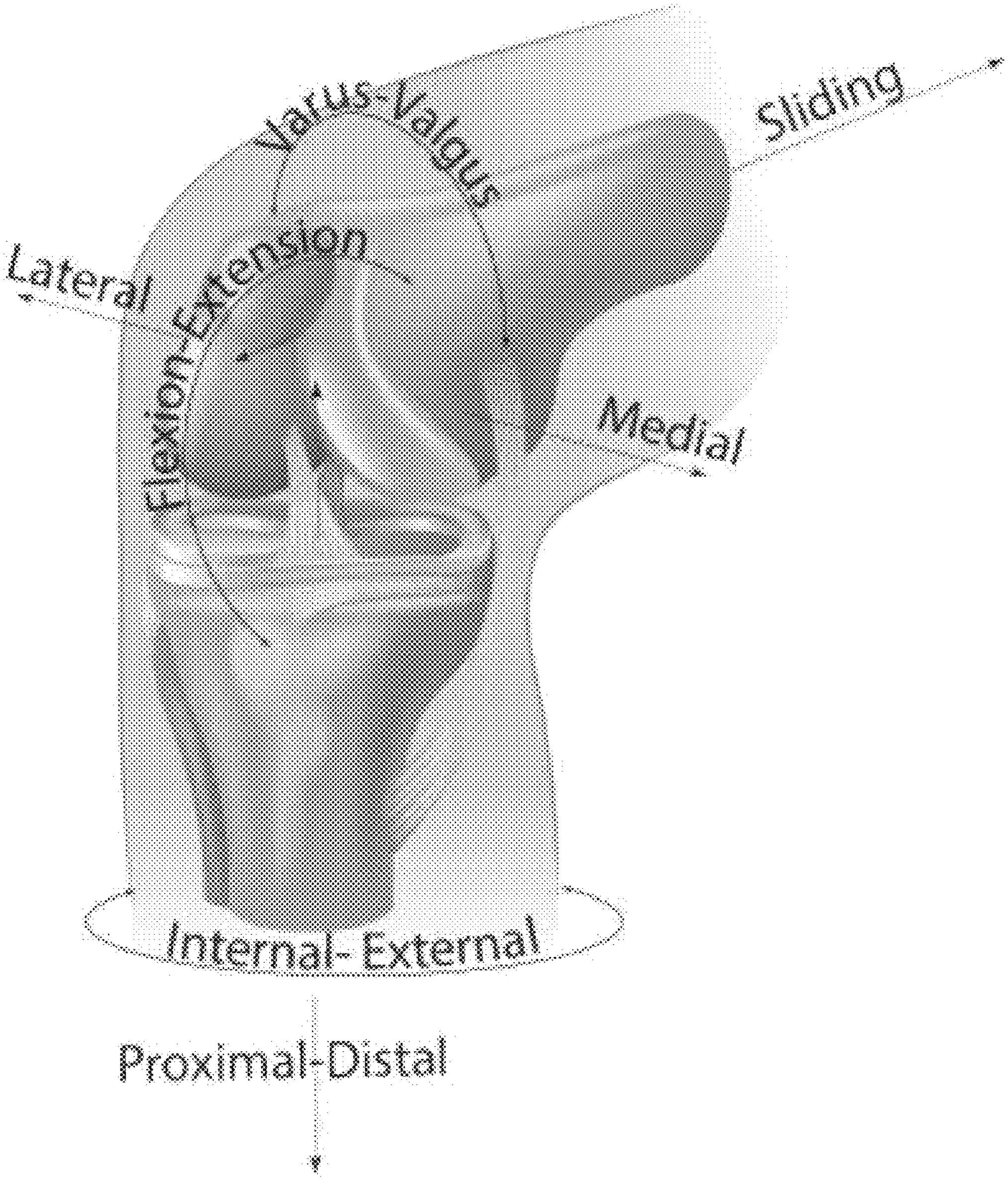
FIG. 27 is a diagram illustrating six DOFs of the knee.

The knee joint has six DOF three rotations and three translations [9] as detailed in FIG. 27. It allows sufficient manipulation for surgical applications and has been extensively studied to determine the kinematic properties and planes each occurs in [13]. Most humanoids use a one DOF hinge model for the knee [14], however for surgical applications the relative motion between variables, such as abduction and inner rotation in relation to flexion angles is required to manipulate a patient's leg to gain access to the inner knee [9].

It is preferable to represent a leg kinematic model in a known format. A range of robot kinematic models exists. The most commonly used model is the Denavit and Hartenberg (DH) model, that was developed with a unique notation to describe a serial robot's joints and links. The DH model is today a 3-dimensional robot pose modelling and computation standard [15]. The notation represents the geometric configuration of each link and joint of the leg completely with four variables (DH Parameters) ($\alpha$, $\theta$, d and a) [16]. With the DH parameters known between two link frames, the homogeneous transformation can be calculated and with all nine sets of link parameters identified, the final position of the foot can be calculated for any joint configuration relative to the base position. Alternative systems exist and have benefits relative to the DH notations. Frank Park shows that the product-of-exponentials (POE) system has several advantages over the DH parameters, however the DH parameters is currently the industry standard [17] and used by many engineers and well-known robot configurations, supporting future integration with the leg kinematic model. Wu et al. developed an analytical approach to convert from POE to DH parameters to support the use of robots defined with the POE system [18]. Fujie et al. developed the six DOF inverse kinematic model of the knee for using advanced testing devices on the knee [19]. Their model only included the knee and is mainly used for leg-attached devices to simulate knee kinematics. For knee and hip surgery, the patient's foot is manipulated to adjust the joint kinematics to achieve a surgical position and to ensure seamless integration with many other robots and applications [19]. For this study the industry standard DH parameter model was selected to define the leg robot model.

To verify a robot model, parameters needs to be identified that shows the accuracy across a data set. Coa et al. defines the workspace of a robot as "the set of points that can be reached by its end-effector" [20], which is ideal to compare the robot model developed in this study of the leg relative to known parameters. The kinematic model of the leg requires an understanding of the workspace that the leg can reach or manipulated in. Leg motion is defined in three categories that include normal muscle motion where a person move their leg, passive motion that exclude all muscle action or external forces, and active motion where the limb or part of it is moved though applying external forces. For surgery a combination of passive and active motion is used by surgeons or a robotic manipulator to increase the range of motion of all the joints. The leg motion has limits impose by bone structure, ligaments and muscle limitations. These influence the workspace of the leg and thus the model. The workspace to expect for robotic surgery during the model validation can be seen from the passive motion research. As detailed by Leardini et al.' Wilson et al. and Blankevoort et al, passive motion defines the coupling that exists between movements, and the limits the leg operates within [21], [10], [22]. It is the motion of the leg joints in the safe region of the total workspace [23], where the knee is moved with a minimal force of, e.g., 3N-30N [24].

Table 9 show the ranges for active manipulation (such as for a cadaver leg) or under passive conditions.

TABLE 9

Passive (loaded) ranges for the knee and hip joints [21], [10], [22], [25], [26] [31], [29], [22]. Movement of the hip and knee depends to different degrees on the flexion in the specific joint as shown in column two.

| Movement | Dependency on Flexion | Range [±15%] |
|---|---|---|
| Hip Rotations | | |
| Hip Flexion\Extension | | −16°-120° |
| Hip Adducon\Abducon | at 90° | −12°-39° |
| Hip Internal/External | at 90° | 8° |
| Knee Rotations | | |
| Flexion\Extension | Negligible | −5°-160° |
| Internal/External | Flexion (F): −5° | 0° |
| | F: −5° to 20° | 10° |
| | F: 10° to 30° | 10° |
| | F: 20°-160° | 18° |
| | Flexion at 90° | 20° to 30° |
| Varus/Valgus | F: 20°-120°-Varus | 8° |
| Knee Translations | | |
| Anterior/Posterior | F: −5° to 0° | 0 mm |
| medial Condyle | 10°-30° | −1.5 mm |
| medial Condyle | −5°-120° | 3.4 mm |
| medial Condyle | 120°-160° | 8.4 mm |
| lateral Condyle | −5°-120° | 21 mm |
| lateral Condyle | 120°-160° | 9.8 mm |
| Medial/Lateral | F: 0°-30° | 1-2 mm |
| | F: 30°-120° | 0 |
| Proximal/Distal | F: 0° | 2-5 mm |
| | F: 0°-20° | 0-2 mm |
| | F: 20°-120° | Minimal |

These ranges will not only influence limitations set during implementation of the kinematic model but govern forces from robotic manipulation not to exceed or alter the joint's natural motion. Flexion or extension is the primary rotation of the knee in the sagittal plane, with the center of rotation on the femur and the range from 0° to 120° [25]. During extension, hyperextension can occur that extends the tibia slightly more than a straight leg (normally to −5°) [26]. Posterior/Anterior translation was observed by Hill et al. that showed that in the sagittal plane the femur rolls and slides on the tibia plateau during flexion [27]. Iwaki et al. and Johal et al. measured cadaver knees using an MRI to show that for passive knee flexion, there is an internal rotational motion through the sagittal plane of the tibia [28], [29]. At any point up to 90° the tibia can achieve inner rotation without flexion in the normal kinematic range [30]. Active rotation of the tibia (such as during surgery) can limit and even reverse the natural rotation from 90° to 10 During extension, a screw home mechanism is initiated for the final 10° to stabilize the knee joint [25], [28] and limiting movement and surgical access to the inner knee [31]. In the coronial plane (on the flexion axis) medial to lateral rotation (varus-valgus force) pivots the tibia sideways relative to the femur, resulting in knee abduction or adduction [32]. Extension below 10° restricts varus-valgus (and most other) motion, locking the leg and limiting access to the inner knee for surgical application [10]. Medial to lateral translation and distraction and compression between femur and tibia is minimal during passive flexion [10] and not a significant factor during surgeries such as knee arthroscopy.

Through leg manipulation the patient's foot needs to be guided in such a way as to ensure setting of specific joint angles. A kinematic model of the hip and knee will allow the use of a leg manipulation robot to automate leg movements and joint positions. The kinematic model will enable the system to move the leg without requiring the use of tracking system on the leg and still have the leg and joint parameters from the model instead of the tracking system. To increase surgical space and reduce interference with the surgery; the patient's foot is used as grip point to manipulate the 9 degrees of freedom (DOF) [3, p. 245] of the combined hip [6] and knee motion [10] as shown in FIG. 1. In developing the kinematic leg model, the following assumption are made: (1) The kinematic model was developed for knee and hip surgery in specific; (2) The kinematic model will be verified against values measured by moving a cadaver leg through all ranges; and (3) For testing the model, it is assumed that markers are placed accurately on the Tibia and Femur as previously discussed in relation to the rigid bodies.

To develop a robot kinematic model of the human leg a high level of understanding is required of the task specific joint motions, which in this study is for surgical manipulation.

From the model as shown in FIG. 3, the leg configuration has nine parameters between the hip and knee joints that is needed for development of the DH parameter model. A robot needs positional information of the foot grip point from the kinematic model to determine the required motion. The forward kinematics for the pose of the heel and knee will be calculated from the DH parameters developed in this study, to determine tile foot position. Once the robot is attached to the patient, the inverse kinematics model of the robot will action the robots' movement.

Figure 28A:
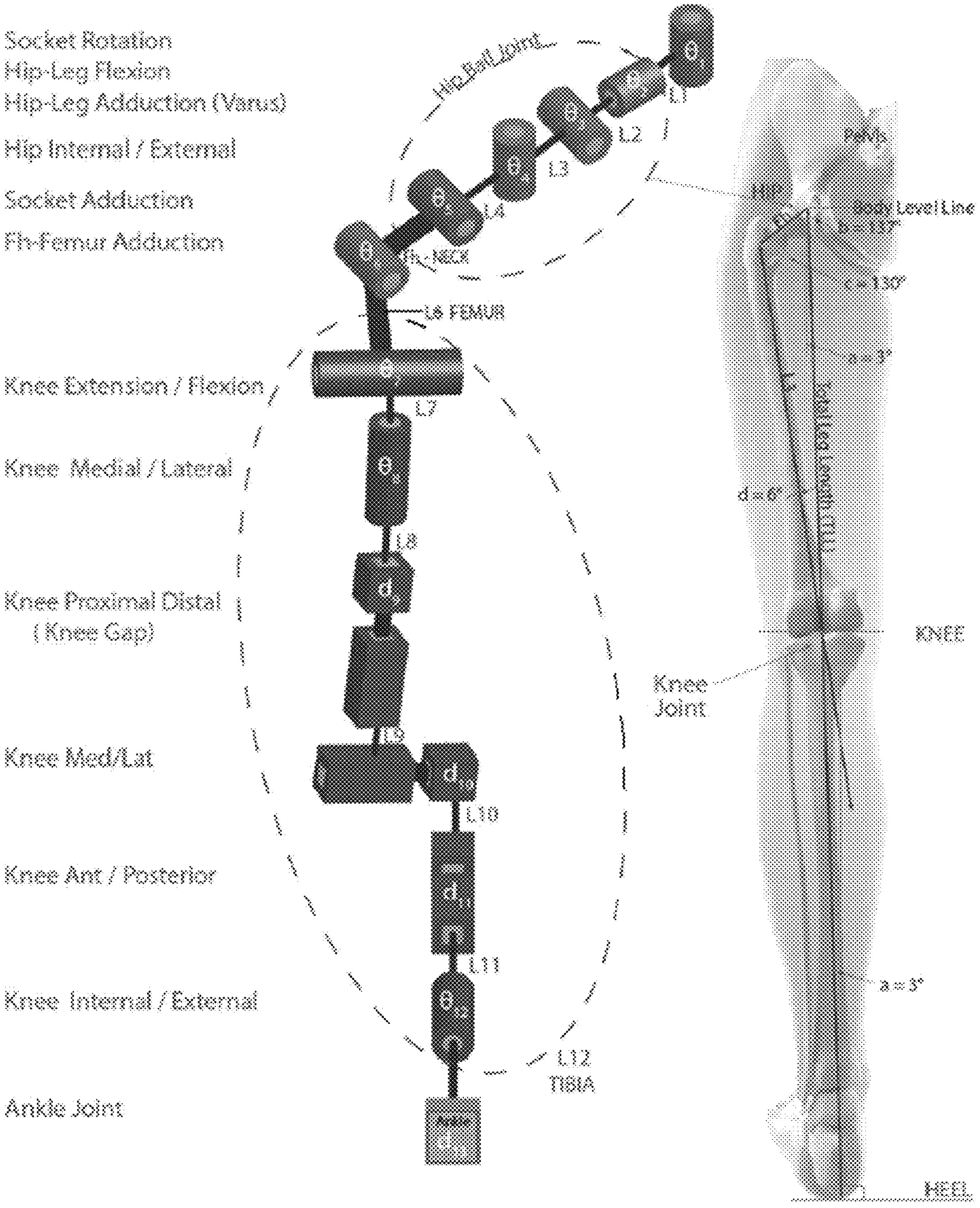
FIG. 28*a* is a leg robot model of a human leg.

Using the limitations and anatomical requirements, the leg is modelled as shown in FIG. 28 and the DH parameters calculated for each of the links. For both the femur and tibia the mechanical axes are used to simulate leg motion and to develop the model. The complete DH Parameters list for the human leg (ankle locked) that include each of the 9 links are detailed in Table 10, as shown in FIG. 36U. Table 10 illustrates DH Parameters for a 9 DOF leg with hip and knee links as shown in FIG. 28*a*. For a straight leg the q variables are: [0 π/2 π/2 π/2 π/2 0 0 −π/2 0 −π/2]. L4 and L10 are the femur and tibia mechanical lengths respectively. q2 to q4 are the hip and q5 to q10 the knee variables, each which is either a rotation (R) or translation (T).

For the DH parameters the link offset 'a' (meters) and joint angle '0' (degrees) is the z-axis linear and angular displacement, while the link offset 'd' (meters) and link twist 'α' (degrees) is the x-axis linear and angular displacement [34].

1) Robot Model: The transformation matrix of the forward kinematic leg model as detailed in Table 10 and FIG. 28 is the product of the homogeneous transformation matrices (A matrices) [16], [15], which can be defined relative to the patient's body (or ball joint) through the matrix $A_{leg}$ as expressed in FIG. 36V, where $r_{11}$ to $r_{44}$ are elements of the homogeneous transformation matrix of the leg, calculated from the DH Parameters. Each element is shown in Table 11, as shown in FIG. 36W, where for example the cosine of angle $q_{10}$ is expressed as $c_{q_{10}}$ and the sine of q3 as $s_{q_3}$.

During each type of surgery; surgeons will use a subset of the variables and for example for a knee arthroscopy; all three DOF in the hip and four in the knee (joints 1, 2, 3, 5, 7, 8 and 10 (see table 10) and none in the ankle are used. Practically; joints not used are manually locked such as using a brace for the ankle or limiting the range of the hip or knee parameter by using bed clamps. From Table 10 certain variables are locked during parts of the procedure and can be set to zero at that time. For knee arthroscopy parameters as identified in the DH parameters will be zero, resulting in a robotic model specifically for this procedure.

The Inventors verified the model by moving it with the same rotations and translations measured during cadaver surgery; where range limits are naturally imposed. As will be discussed, the accuracy of the workspace of the cadaver and model were compared with each other, such as where against time the hip and knee angles were compared between the DH model and actual measured angles to determine the accuracy of the model.

The application of the model dictates the anatomical position selection inside the joint. For validating the DH model and using it for knee arthroscopy the following point inside the knee joint were selected using the CT scan diagonal slices: The condyle center—position as shown in FIG. 24*aa* where the center of the condyle starts to form; Condyle touch point—outer extreme (FIG. 24*aa m-m*) where the condyle is touching the meniscus; top center of joint (FIG. 24*aa n-n*) where maximum gap occurs during flexion; and bottom center of joint (FIG. 4 *q-q*) where a minimum gap is formed during flexion.

As an initial step the total workspace for the hip (3 DOF) and the knee (6 DOF) will be modelled using the kinematic model developed, with data from cadaver experiments as input parameters and ranges. To visualize the knee and foot workspace, the model is simulated in Matlab using the Peter Corke toolbox [16], however specific combinations of the model can be used depending on the procedures. Surgeons extend a person's hip, knee or ankle to make space for instruments and to get to areas to operate on—these manoeuvres reaches maximums for specific part of the model; however, others are not used. For example, during hip surgery some DOF is used in the knee to bend the leg, but none in the ankle. Walking, jogging and different sport activities again use different parts of the leg, however, under normal circumstances these activities do not reach the maxima of the range that the human, leg can go through without injury. The model workspace was validated through:

1) Using ranges from the passive research of the hip and knee joint. The workspace for the cadaver knees were tested during the experiments to determine the accuracy the knee position. Using an optical tracking system, markers were mounted on the cadaver leg as previously discussed with reference to FIGS. 19*c* to 20*b*. Angles for the hip were calculated from the tracked markers and input into the DH model of the human leg (hip only for this first part).

2) Comparison with a cadaver leg moved through a range of surgical positions for the hip and knee joints and measured using the OptiTrack system. Angles from measured data were calculated and used in the full kinematic model to measure the knee and foot (ankle point) workspace and error.

For Cadaver experiments the special rigid bodies and optical marker patterns that have previously been described were used to ensure alignment with the cadaver femur and tibia, enabling accurate calculation of all knee and hip rotations and translation. CT scans of the cadaver legs were taken and used to analyse the position of the anatomical points and translations within the joints, which were then compared to the model for verification.

Figure 28B:
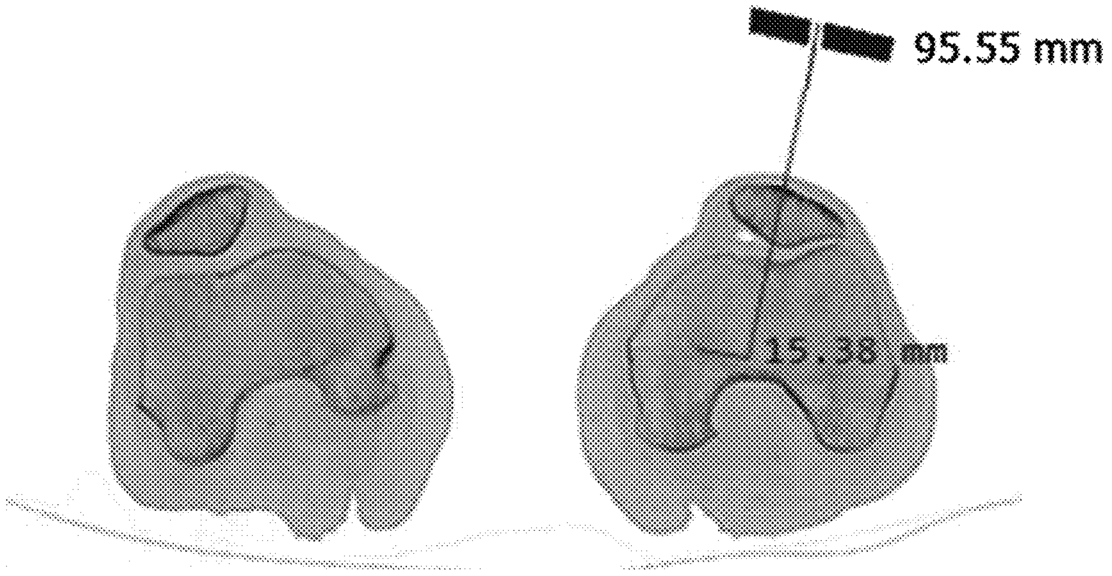
FIG. 28*b* is a cross section CT scan (color inverted) of a femur at the level of condyle center.
Figure 28C:
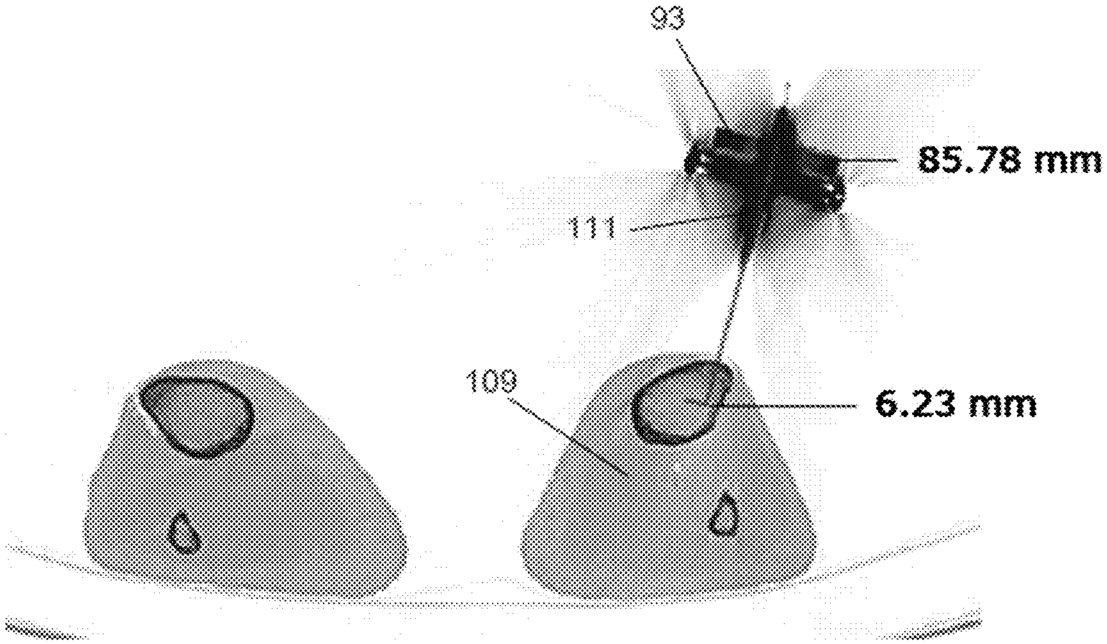
FIG. 28*c* is a cross section CT scan (color inverted) of the femur of FIG. 28*b* at the lee of a surgical pin supporting a Rigid Body.

The DH model is validated by measuring the cadaver joint parameters and use the measured parameters as input into the DH model. The output of the model's knee and foot workspace are then compared with that measure with the optical tracking system. To measure the cadaver joint parameters, the markers are setup and aligned. The rotations (internal/external, varus/valgus) and translations (medial/lateral, posterior/anterior and distal/proximal) are calculated relative to the flexion angle. FIGS. 28*b* and 28*c* are cross sectional scans through the femur at condyle center (FIG. 28*b*) and at surgical pin (FIG. 28*c*). They respectively depict measurements from G to the femoral Condyle Center and Measurements from RB plate 93 and surgical pin 111 to the center of tibia 109.

In the knee joint a vector ($v_t$) is defined from the center of frame on the femoral condyles (FIG. 28*b*) to the ankle, describing the motion of the tibial mechanical axis. The knee varus angle (β) is:

$$\beta = a\tan 2(\|v_{t_{yz}} \times v_t\|, v_{t_{yz}} \cdot v_t)$$

where $v_{t_x}$ is the projected $v_t$ vector on the unity vector ($x_n$) of the femur C frame's x-axis and $v_{t_{yz}}$ the $v_t$ vector in the yz-plane. Projecting $v_t$ (on the normalized axes of frame C on the femoral mechanical axis, allows the calculation of the flexion angle (α):

$$\alpha = a\tan 2(\|v_{t_{xz}} \times v_t\|, v_{t_{xz}} \cdot v_t)$$

The femur vector ($v_f$) that describes the hip rotations is the mechanical axis from the hip ball joint too the femoral condyle center. Using a rotational matrix is an alternative option of calculating the knee angles between vectors $v_f$ and $v_t$.

The rotational matrix between the femur and tibia is:

$$^{v_f}R_{v_t} = 2\frac{(t_r t_r^{-1})}{(t_r^{-1} t_r) - I} \text{ with } t_r = v_f + v_t$$

and the knee IE angle γ:

$$\gamma = a\tan 2(-^{v_f}R_{v_t}(1,2), {}^{v_f}R_{v_t}(1,1))$$

The femur mechanical axis ($v_f$) is defined as the link from the hip joint. The femur mechanical axis (FMA) is defined as the link from the hip joint center to the center of the condyles on the knee as shown in FIG. 24*a* and as item 105 in FIG. 21. The vector for the hip is relative to the world frame and can be formulated from the previous points defined in it. Angles and translations are measured relative to the sagittal (flexion), coronal (varus) and transverse (knee gap) planes (see $T_G$ expressed in FIG. 36X).

Using the rotational matrix as developed above, the hip varus (ψ) and flexion (θ) angles are:

$$\psi = a\tan 2(\|v_{f_{yz}} \times v_f\|, v_{f_{yz}} \cdot v_f)$$

$$\theta = a\tan 2(\|v_{f_{xz}} \times v_f\|, v_{f_{xz}} \cdot V_f)$$

for the hip roll angle, we setup a frame on the femur mechanical axis and calculate the pose of this frame to the world frame (OptiTrak origin) $^{W}R_c$.

The hip roll angle is:

$$\psi = a\tan 2(-^{W}R_c(1,2), {}^{W}R_c(1,1))$$

The main control parameter for robotic leg manipulation is to know the size of the knee gap, i.e. the instrument gap. Using vectors at different positions inside the knee we can measure the gap size and determine if the instrument can pass through it. From FIG. 24*aa*. The instrument gap space can be measured at point b, c and d according to the expressions shown in FIG. 36Y.

Rotations and Translations calculated from the measured OptiTrack data are used as input into the robotic leg manipulation model that result in the foot workspace of the model that can be compared to the cadaver foot workspace.

Figure 29:
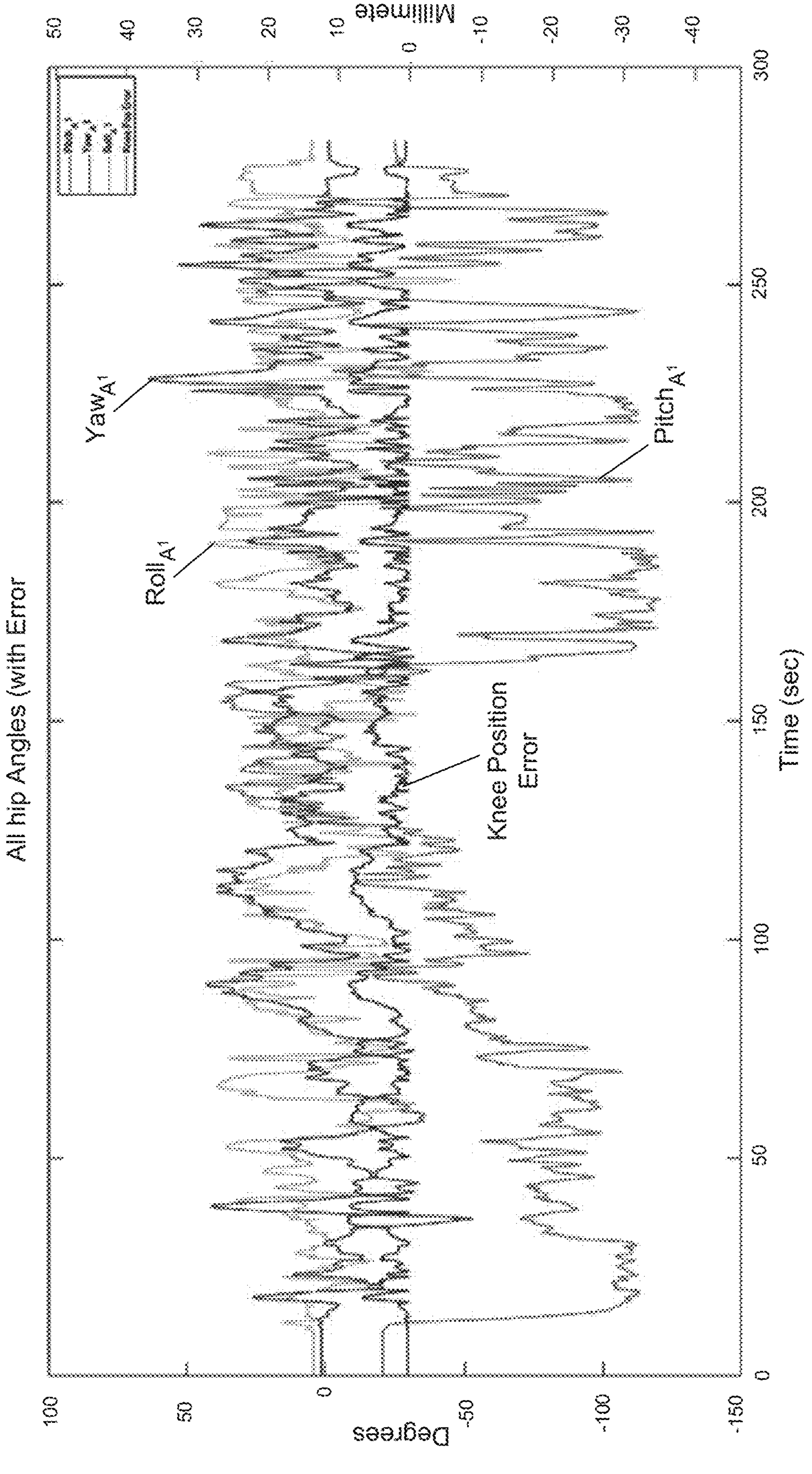
FIG. 29 is a graph showing the hip flexion, varus and inner rotation angles and resulting error from a tracked femoral condyle center relative to that provided by a Denavit-Hartenberg (DH) model of the hip according to an embodiment.

FIG. 29 is a graph showing the hip flexion, varus and inner rotation angles and the resulting error from the tracked femoral condyle center to that provided by the DH model of the hip. The hip angles were measured from a cadaver leg and these fed into the DH model and the knee position from the model compared to that of the cadaver at each measurement point (sixty per second over three hundred seconds). FIG. 29 shows the hip angles and the error between the model and cadaver knee position. The average knee position error across the data set of 3 minutes is 0.43 mm, showing the DH parameter model is highly accurate for the hip and well suited to joint surgery where the joint gaps are up to twenty millimeters.

Figure 30:
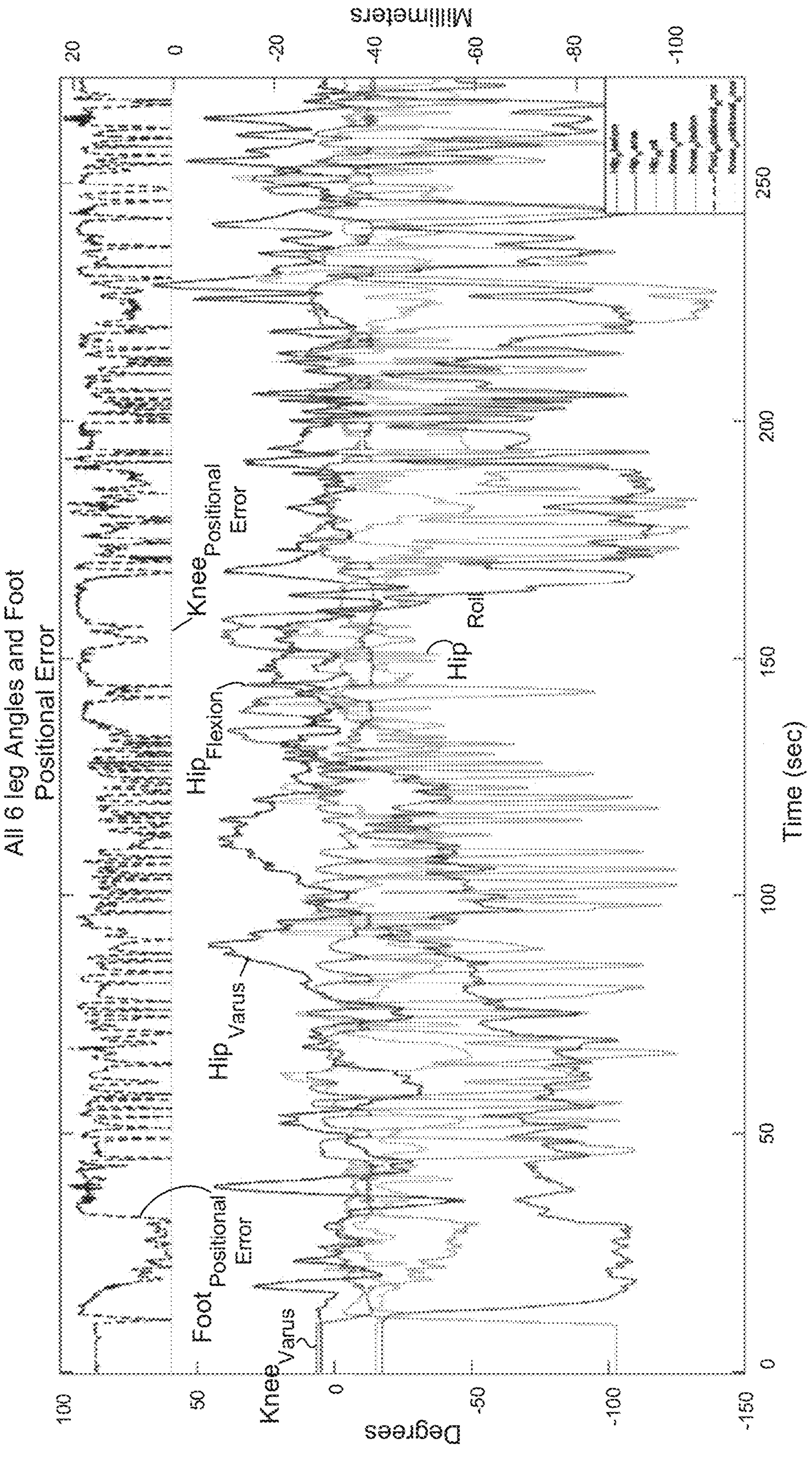
FIG. 30 is a graph showing the knee angles and the ankle positional error between a human (cadaver) leg and the DH model.

FIG. 30 shows the knee flexion, varus and inner rotation angles and the translations in the knee as observed from the foot position. A key application for the model is to adjust the Instrument gap in the knee joint for knee arthroscopy. The six DOF in the knee joint were modelled using three rotations and three translations in the DH model. Fujie et al. developed a similar model and use the inverse kinematics of the model to measure and verify the forces on the joint [19]. Using the knee angles measured from the cadaver knee, we compared the ankle position of the cadaver with that of the model. FIG. 30 shows the knee angles and the ankle positional error between the cadaver and the DH Model. The resultant error as shown in FIG. 30 is an average of 15 mm, which is a combination of the hip error (0.43 mm) measured at the knee, the knee translation and the error between the knee model and cadaver position. As shown in FIG. 31*a*, the translation inside the knee can be checked at a specific angle. As shown in the graph of FIG. 31*b*, from 0° to 90° if we track the motion of the center of rotation of the tibia on the femur, the translation of the knee in the −Y direction relative to the femoral frame is 14.1 mm. The ankle positional error due to the knee six DOF motion is 15 mm−0.43 mm−14.1 mm=0.47 mm, which is in line with the error we measured due to the hip motion.

Figure 31:
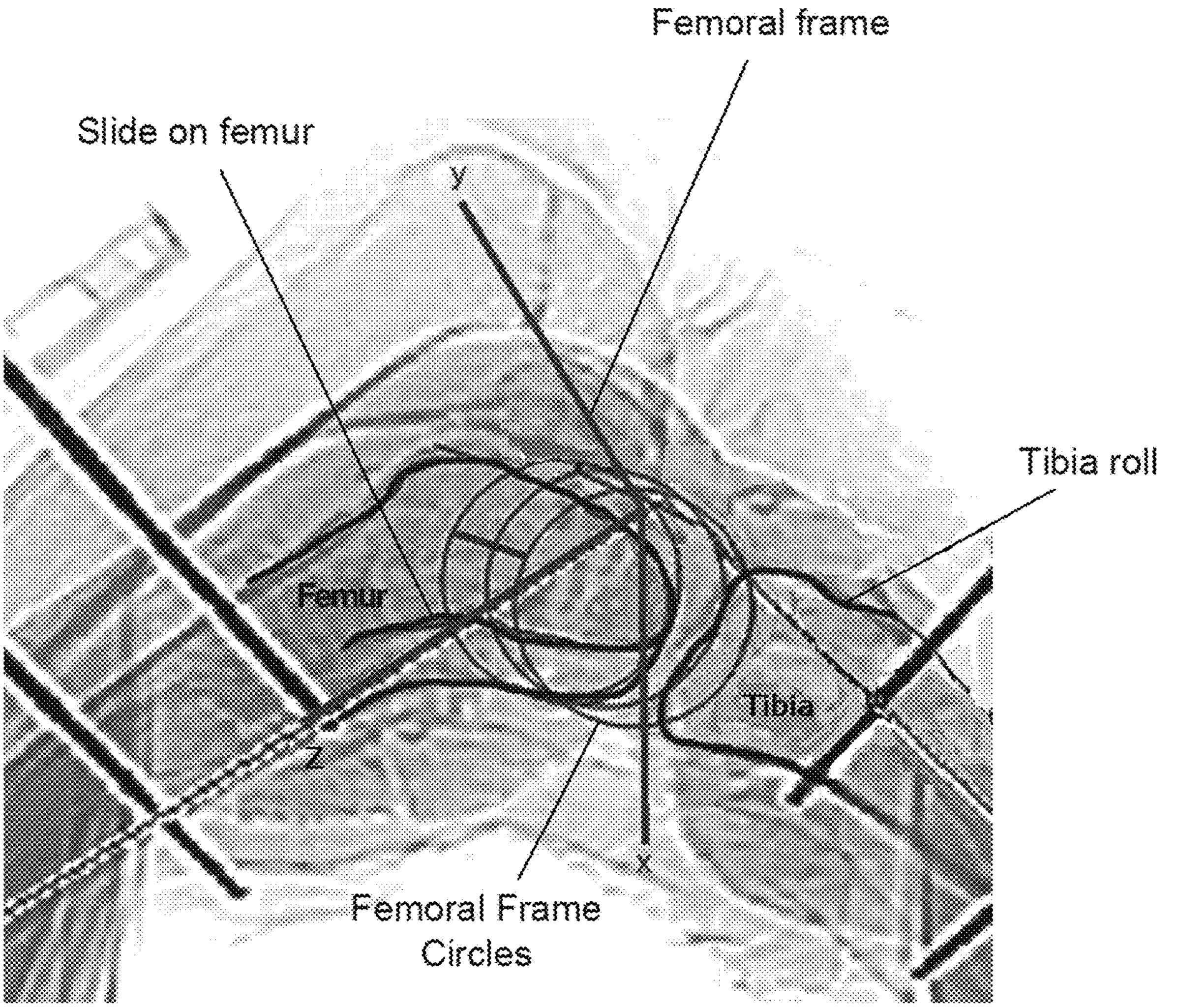
FIG. 31 is a CT scan (color inverted) of a knee. The tibia roll and slide on the femur and the translation of 14.1 mm is shown from the translated center of rotation relative to the femoral frame circles.
Figure 32:
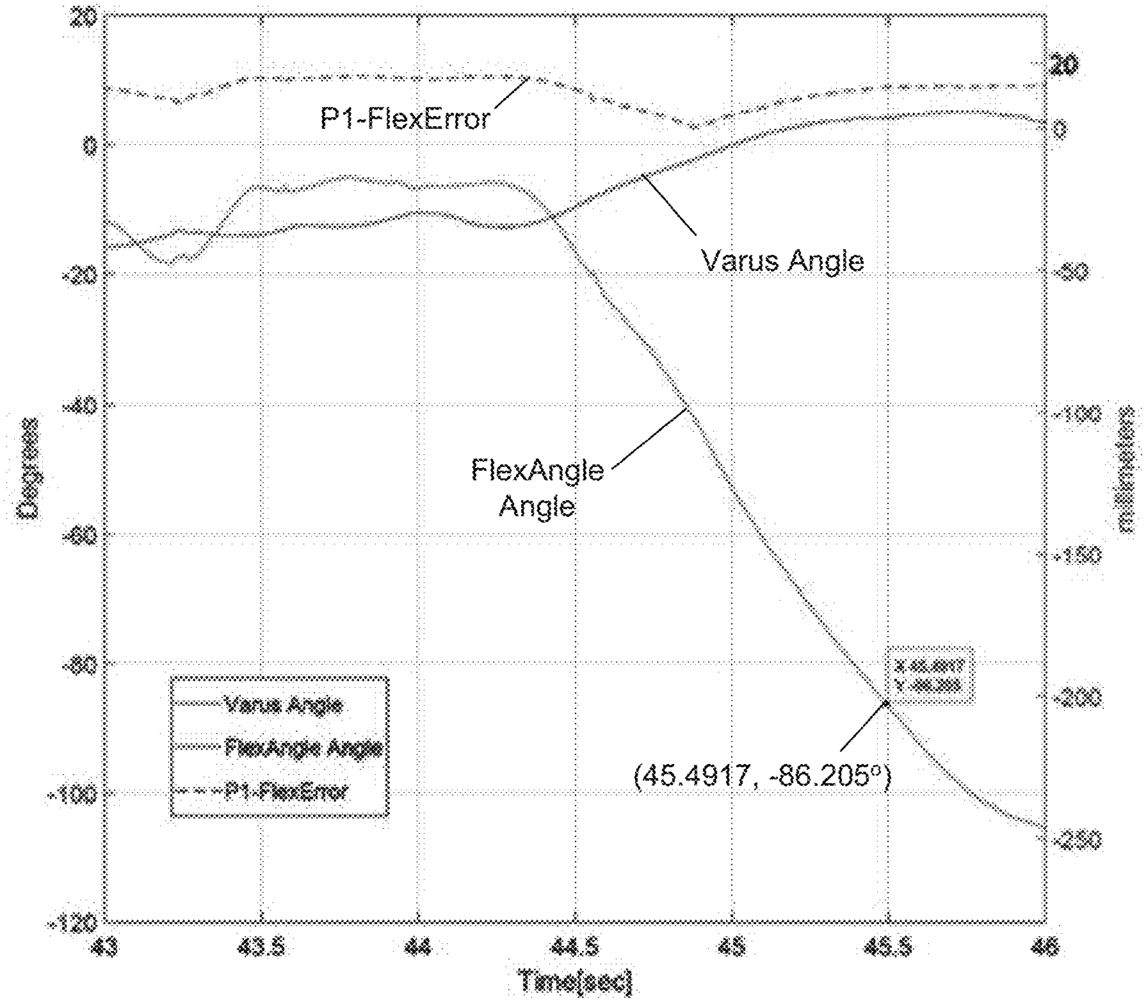
FIG. 32 is a graph of knee angles at 45.5 seconds relative to the femoral axis with the knee flexion, knee varus and foot error curves shown.
Figure 33:
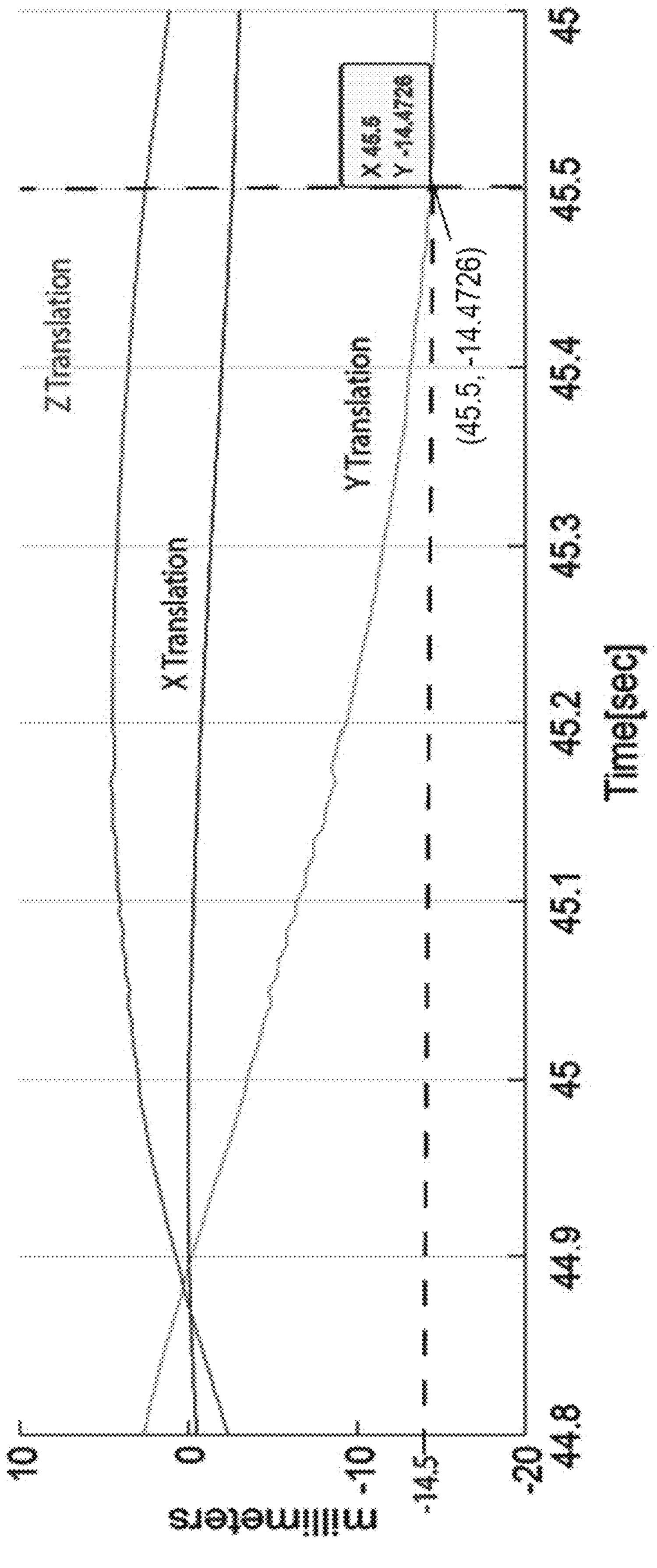
FIG. 33 is a graph of XYZ foot translation and error in the global frame. The Y translation and error combination is −14.5 mm at 45.5 degrees when comparing to the CT scan translation at that angle implying that the foot error due to hip and knee motion is 0.89 mm.
Figure 34:
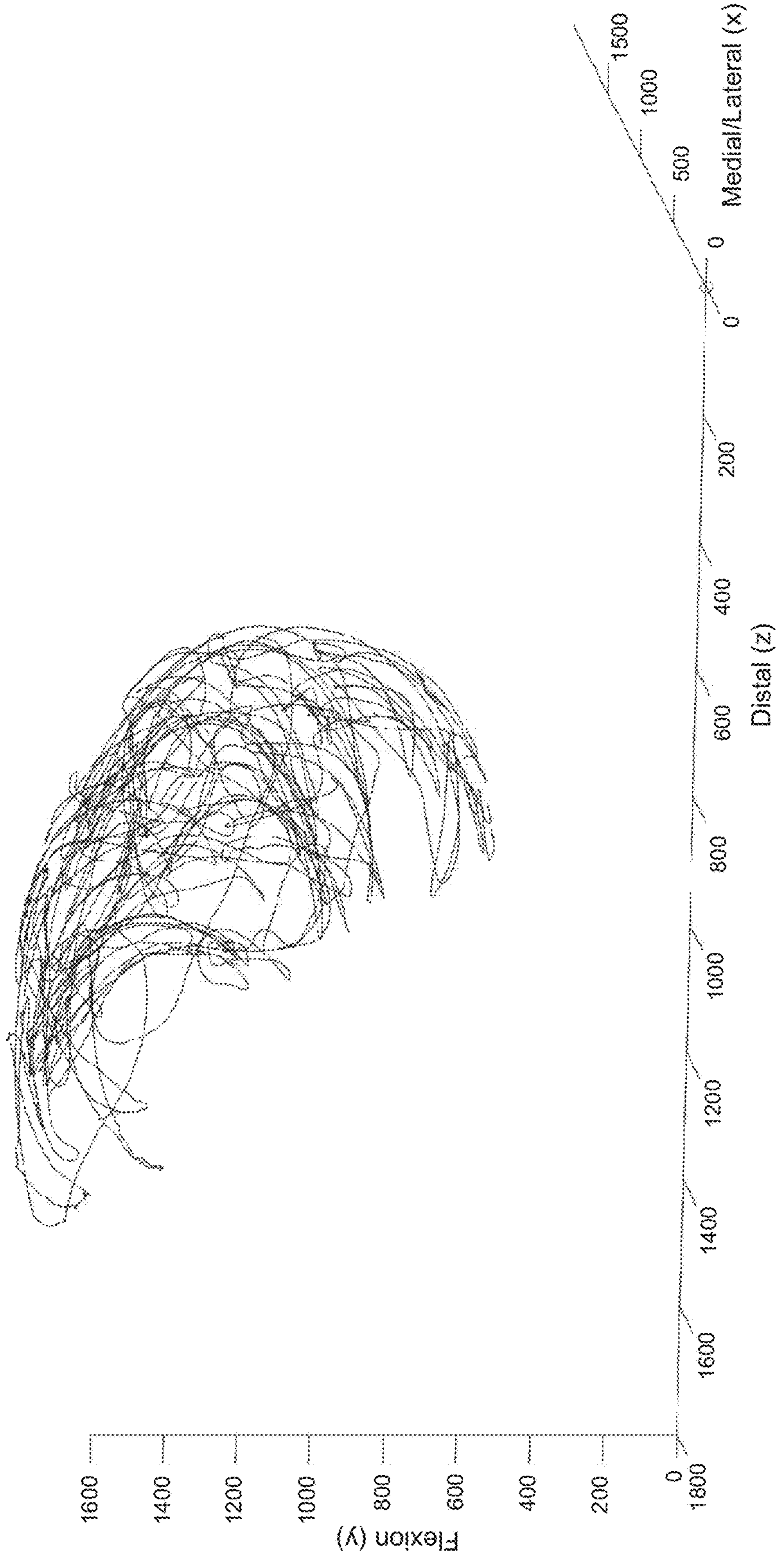
FIG. 34 is a graph of a human (cadaver) foot workspace.

From the cadaver measured data and the output of the robotic leg model, FIG. 31 is a comparison of the workspace difference. The difference in workspace between the DH model and a cadaver leg is marginal and the impact on the instrument gap in the knee joint minimal. An ankle positional error of 1 mm can influence the knee angle by 1° and the hip angle by 0.5°. A key interest for this research is to measure the knee instrument gap, which can be impacted by less than 0.1 mm for a foot error of 1 mm and negligible when steering surgical instruments such as at worst case a 4 mm arthroscopy though the knee cavity.

In analyzing the data, it became clear that accuracy depends to an extent on the external forces that are exerted on the cadaver leg, which change the Mo (hip socket) rotational position, impacting the center of rotation and accuracy of the results.

The presented kinematic model of the human leg can be used for applications ranging from robust human robot designs to medical applications. Applications include using a robotic device to manipulate a patient's leg from the heel during hip or knee surgeries. For each procedure, only specific joints are used, and the other variables can be set to zero. Knee arthroscopy has been discussed as an example. A significant advantage of these techniques is to be able to move the patient leg and know the leg angles and parameters without optical tracking.

The application for the leg kinematic model is the development of a leg manipulation robot to move a patient's leg during leg surgery, such as for knee arthroscopy, where with traditional surgery a surgeon is using a patient's foot to manipulate the knee joint to the required position. A forward kinematic robotic model of a human leg has been developed. In order to operate an actuator, such as actuator 42 of joint positioning apparatus 100 (FIG. 1) to manipulate the patient's foot, the processing assembly uses the forward kinematic model of the leg as input to an inverse six DOF kinematic model of the robot manipulator, to direct the motors, e.g. actuators 42, 44 to move a specific distance to achieve the desired foot position, and so set the correct variable (angle or translation in knee or hip) required for surgery.

Aspects of the embodiments described and illustrated herein can be interchanged or otherwise combined.

In an embodiment the processing assembly 126 is able to determine the leg position or "pose" with reference to kinematic models of the leg and robot so that it is unnecessary to use optical markers on the leg bones in the following ways.

1) Using Operator (surgeon or Robot) manual input:
   a. Surgeon enters one or more pose parameters that define the pose, for example a knee angle to be achieved, into the processing assembly 126.
   The input of the pose parameters may be achieved by operating the keyboard 49 and/or mouse 21 or by using another HMI device such as a joystick.
   b. In response to receiving the pose parameters the processing assembly, configured by instructions of surgical assistance software 27 that are in accordance with the equations that have been discussed, calculates the necessary foot position to be adopted from the pose parameters.
   c. Using the robot inverse kinematic model, the processing assembly 126 uses the necessary foot position to command actuators 42, 44 to operate robot arms 16, 18 to position the robot end-effector, e.g. footplate 8 at the necessary foot position.
   d. The robot arms 16, 18 then move the foot to the necessary position to achieve the leg angle, i.e. the desired pose.
   e. Signals from torque and force sensors on the robotic arms 42 and 44 and the leg inverse kinematic model 162 can be used by the processing assembly 126 to limit the motion of leg 91 to acceptable limits
   f. The gap size d is provided (displayed on a screen 48 or transmitted) to the operator.
   g. Depending on the accuracy of the angle requested the gap 5 will be 4 mm or larger. If too small or large, the surgeon can request another pose to set the knee to. The hip will be pre-set to ensure the correct path is followed by the knee and foot which is attached to footplate 8 of robotic arm 16.
2) Automated positioning, which is used by the operator, which may be a surgeon or robot can be implemented as follows in an embodiment.
   a. Processing assembly 1226 is able to determine the direction to move the leg 91 to by knowing the position of the tip of the surgical instrument, inside the knee joint. A database or computer vision system can be implemented to determine the location and mapping of the joint.
   b. Measure the joint gap (ROI)
      i. If the joint gap is too small the processing assembly 126 operates actuators 42, 44 to move the robotic arms 16, 18 to incrementally increase/ decrease the knee angles of leg 91 while measuring the gap—using feedback from the arthroscope 40.

ii. From the gap size and instrument position, the processing assembly 126 calculates an angle to set the leg to.

iii. Using the forward and/or inverse kinematic models of the leg and robot (160, 162, 164, 166) to incrementally move the footplate 8 and thus the foot to the correct position.

iv. Signals from torque and force sensors on the robotic arms 16, 18, and the leg inverse kinematic model can be used by the processing assembly 126 to limit motion of leg 91 to safe limits.

v. As the footplate 8, and thus the foot, is moved, the processing assembly 126 measures the gap d in real-time to determine when the correct gap size is achieved (e.g., larger than 4 mm to provide a margin of error)

c. As the operator moves the arthroscope 40 through the joint 5, the above process (i-v) is repeated to ensure the varying dimension d of the gap 5 stays at the required size, which is dependent on the speed that the instrument is moved, processing capability of the processing assembly 126 and how fast the robotic arms can safely move the leg. A haptic feedback apparatus, responsive to processing assembly 126, may be applied to the arthroscope to provide feedback for the operator (robot or surgeon) to limit movement.

It is also possible for the processing assembly 126 to sense the position of robotic arms 16, 18 (e.g. with optical markers 38 of sensing system 152 or with other trackers such as mechanical or electromagnetic) to obtain robotic arm positions which are available to the processing assembly 126.

Apart from optical sensing, the robot also has accurate positional information of its arms from motor encoders and positional sensors. However, the optical sensing relates the surgical instrument position in reference to the robot and thus the leg.

The rigidity of the boot 12 can be measured and adjusted to compensate for any movement. In both manual and automated mode, the leg kinematic model 160 is specially adjusted for the current patient through preoperative CT scans of the patient E.g. tibia and femur lengths of the current patient are used in the model.

Both the manual and automated options are advantageous in that they ensure the gap size relative to the current situation where the surgeon really guesses the gap size.

The desired leg position ("pose") may be attained by the processing assembly 126 by reference to the kinematic models and without need for on the bone markers in either a manual mode or an automated mode as follows:

1) Manual Mode: Angles of the Knee (and Hip if Necessary) is Input by the Surgeon a. The processing assembly 126 receives the desired pose parameters (e.g. leg at 30 degrees) from the surgeon (which may be by any suitable means such as mouse, keyboard, joystick or by voice command);

b. The processing assembly 126 applies the pose parameters defining the pose (e.g. angles of the femur and tibia, position of the ankle and hip) to the forward kinematic model 160 of the leg 91.

c. The output of the forward kinematic model of the leg provides the positional coordinates for the ankle (which attached to the footplate 8 of the first robotic arm 16) in order to achieve the desired pose.

d. The processing assembly applies the positional coordinates for the ankle to the robot inverse kinematic model 166 of the robot 100.

e. The robot 100 then moves the first robot arm 16 (to which the ankle is connected by footplate 8)—with path planning to avoid damage to the leg—to bring the ankle to the ankle position to achieve the pose.

2) Automated Mode: Pose of the Leg is Calculated from the Feedback of the Joint Gap Size a. Knowing the instrument position inside the knee, for example by application of computer vision to images captured from the ROI, the processing unit 126 commands the robot 100 to move the leg 91 and measures the gap 5 as it moves it—using the inverse leg kinematics model 162 the processing assembly 126 is configured by instructions comprising surgical assist software to calculate the leg angles or anatomical points.

b. In this case, the forward kinematics model 164 of the robot 100 is used to determine the ankle position, or alternatively it can instead be measured with sensors or optical tracking—both non-invasive options.

c. As the leg moves the processing assembly 126 localises and maps the instrument inside the knee joint and thus is able to determine that the movement of the leg is proceeding in the correct direction It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described The disclosures of the following documents, which are referred to herein, are incorporated herein in their entireties by reference.

[Bai and Wang, 2016] X Bai and W Wang. Principal pixel analysis and SVM for automatic image segmentation. *Neural Computing and Applications,* 27(1):45-58, 2016.

[Bieniek and Moga, 2000] A Bieniek and A Moga. An efficient watershed algorithm based on connected components. *Pattern Recognition,* 33(6):907-916, 2000.

[Bleau and Leon, 2000] A Bleau and L J Leon. Watershed-Based Segmentation and Region Merging. *Computer Vision and Image Understanding,* 77(3):317-370, 2000.

[Caselles et al., 1993] V Caselles, F Catté, T Coll, and F Dibos. A geometric model for active contours in image processing. *Numerische Mathematik,* 66(1):1-31, 1993.

[Caselles et al., 1997] V Caselles, R Kimmel, and G Sapiro. Geodesic Active Contours. *International Journal of Computer Vision,* 22(1):61-79, 1997.

[Chan and Vese, 2001] T F Chan and L A Vese. Active contours without edges. *IEEE Transactions on Image Processing,* 10(2):266-277, 2001.

[Cootes et al., 1995] T F Cootes, C J Taylor, D H Cooper, and J Graham. Active Shape Models-Their Training and Application. *Computer Vision and Image Understanding,* 61(1):38-59, 1995.

[Crevier, 2008] D Crevier. Image segmentation algorithm development using ground truth image data sets. *Computer Vision and Image Understanding,* 112(2):143-159, 2008.

[Dahiteb, 2015] Dahiteb. Arthroscopes, 2015.

[Demirkaya and H. Asyali, 2004] O Demirkaya and M H. Asyali. Determination of image bimodality thresholds for different intensity distributions. *Signal Processing: Image Communication,* 19(6):507-516, 2004.

[Funck et al., 2003] J W Funck, Y Zhong, D A Butler, C C Brunner, and J B Forrer. Image segmentation algorithms applied to wood defect detection. *Computers and Electronics in Agriculture,* 41(1):157-179, 2003.

[Huang and Su, 2006] F Huang and J Su. Momentbased Shape Priors for Geometric Active Contours. volume 2, pages 56-59. IEEE, 2006.

[Jaiprakash et al., 2016] A Jaiprakash, J M Roberts, and R Crawford. Perceptions of Orthopaedic Surgeons on knee arthroscopic surgery. *Journal of Orthopaedic Surgery* (*in press*), 2016.

[Li et al., 2015] A Li, Y Li, T Wang, and W Niu. Medical image segmentation based on maximum entropy multi-threshold segmentation optimized by improved cuckoo search algorithm. In *Image and Signal Processing* (*CISP*), 2015 8*th International Congress on*, pages 470-475. IEEE, 2015.

[Ma et al., 2010] Z Ma, J M R S Tavares, R N Jorge, and T Mascarenhas. A review of algorithms for medical image segmentation and their applications to the female pelvic cavity. *Computer Methods in Biomechanics and Biomedical Engineering,* 13(2):235-246, 2010.

[Macgroarty, 2015] K Macgroarty. Knee Arthroscopy, 2015.

[Malladi et al., 1993] R Malladi, J A Sethian, and B C Vemuri. Topology-independent shape modeling scheme. In *Geometric Methods in Computer Vision II,* 246 (Jun. 23, 1993), volume 2031. SPIE, 1993.

[MathWorks, 2016a] MathWorks. Marker-Controlled Watershed Segmentation, 2016.

[MathWorks, 2016b] MathWorks. OTSU Matlab code (graythresh), 2016.

[McKeon et al., 2009] B P McKeon, J V Bono, and J C Richmond. *Knee Arthroscopy*. Number Book, Whole. Springer, New York, NY, 2009.

[Mumford and Shah, 1989] D Mumford and J Shah Optimal approximations by piecewise smooth functions and associated variational problems. *Communications on Pure and Applied Mathematics,* 42(5):577-685, 1989.

[Nikolay, 2013] S Nikolay. Active Contours implementation & test platform GUI, 2013.

[Nixon and Aguado, 2012] M S Nixon and A S Aguado. *Feature extraction & image processing for computer vision*, volume 3. Elsevier, Oxford, 2012.

[Osher and Sethian, 1988] S Osher and J A Sethian. Fronts propagating with curvature dependent speed:

Algorithms based on Hamilton-Jacobi formulations. *Journal of Computational Physics*, Volume 79(1): Pages 12-49, 1988.

[Otsu, 1979] N Otsu. A Threshold Selection Method from Gray-Level Histograms. *IEEE Transactions on Systems, Man, and Cybernetics,* 9(1):62-66, 1979.

[Rice, 2015] J J Rice. Healthcare Bluebook, 2015.

[Sarti et al., 2002] A Sarti, R Malladi, and J A Sethian. Subjective Surfaces: A Geometric Model for Boundary Completion. *International Journal of Computer Vision,* 46(3):201-221, 2002.

[Strydom et al., 2015] R Strydom, S Thurrowgood, A Denuelle, and M V Srinivasan. UAV Guidance: A Stereo-Based Technique for Interception of Stationary or Moving Targets. In *Conference Towards Autonomous Robotic Systems*, pages 258-269. Springer, 2015.

[Tachibana et al., 2012] H Tachibana, Y Uchida, and H Shiizuka. Determination of the optimized image processing and template matching techniques for a patient intrafraction motion monitoring system. *Medical Physics,* 39(2):755-764, 2012.

[Tarabalka et al., 2010] Y Tarabalka, J Chanussot, and J A Benediktsson. Segmentation and classification of hyperspectral images using watershed transformation. *Pattern Recognition,* 43(7):2367-2379, 2010.

[Ward and Lubowitz, 2013] Benjamin D Ward and James H Lubowitz. Basic knee arthroscopy part 3: diagnostic arthroscopy. *Arthroscopy techniques,* 2(4):e503-e505, 2013.

[Xu et al., 2011] S Xu, X Xu, L Jin, and E Song. Characteristic analysis of Otsu threshold and its applications. *Pattern Recognition Letters,* 32(7):956-961, 2011.

[1] B. P. McKeon, J. V. Bono, and J. C. Richmond, *Knee Arthroscopy*. New York, NY: Springer, 2009, no. Book, Whole.

[2] S. Rasool and A. Sourin, "Image-driven virtual simulation of arthroscopy," *The Visual Computer*, vol. 29, no. 5, pp. 333-344, 2013.

[3] B. D. Ward and J. H. Lubowitz, "Basic knee arthroscopy part 3: diagnostic arthroscopy," *Arthroscopy techniques*, vol. 2, no. 4, pp. e503-e505, 2013.

[4] M. Strydom, A. Jaiprakash, R. Crawford, T. Peynot, and J. Roberts, "Towards Robotic Arthroscopy: 'Instrument gap' Segmentation," 2016.

[5] L. Blankevoort, R. Huiskes, and A. de Lange, "The envelope of passive knee joint motion," *Journal of Biomechanics*, vol. 21, no. 9, pp. 705-720, January 1988.

[6] A. Jaiprakash, J. M. Roberts, and R. Crawford, "Perceptions of Orthopaedic Surgeons on knee arthroscopic surgery," *Journal of Orthopaedic Surgery* (*in press*), 2016.

[7] L. Wu, J. Jaiprakash, A. K. Pandey, D. Fontanarosa, Y. Jonmohamadi, M. Antico, M. L. Strydom, A. Razjigaev, F. Sasazawa, J. Roberts, and R. Crawford, "Robotic and image-guided knee arthroscopy," in *In Mohammad H. Abedin-Nasab* (*Ed.*), *Elsevier's Handbook of Robotic and Image-Guided Surgery*. Elsevier, 2018.

[8] A. Marmol, T. Peynot, A. Eriksson, A. Jaiprakash, J. Roberts, and R. Crawford, "Evaluation of keypoint detectors and descriptors in arthroscopic images for feature-based matching applications," *IEEE Robotics and Automation Letters*, vol. 2, no. 4, pp. 2135-2142, 2017.

[9] J. R. Doyle, "The Arthroscope, Then and Now," *Techniques in Hand & Upper Extremity Surgery*, vol. 12, no. 4, p. 201, dec 2008.

[10] K. W. Nam, J. Park, I. Y. Kim, and K. G. Kim, "Application of stereo-imaging technology to medical field," *Healthcare informatics research*, vol. 18, no. 3, pp. 158-163, 2012.

[11] Stryker, "Mako." [Online]. Available: https://www.stryker.com/us/en/portfolios/orthopaedics/joint-replacement/mako-robotic-arm-assisted-surgery.html

[12] D. Stoyanov, M. V. Scarzanella, P. Pratt, and G.-Z. Yang, "Real-time stereo reconstruction in robotically assisted minimally invasive surgery," in *International*

*Conference on Medical Image Computing and Computer-Assisted Intervention*. Springer, 2010, pp. 275-282.

[13] S. Röhl, S. Bodenstedt, S. Suwelack, H. Kenngott, B. Mueller-Stich, R. Dillmann, and S. Speidel, "Real-time surface reconstruction from stereo endoscopic images for intraoperative registration," in *Medical Imaging* 2011*: Visualization, Image-Guided Procedures, and Modeling*, vol. 7964. International Society for Optics and Photonics, 2011, p. 796414.

[14] M. Field, D. Clarke, S. Strup, and W. B. Seales, "Stereo endoscopy as a 3-d measurement tool," in *Engineering in Medicine and Biology Society,* 2009. *EMBC* 2009. *Annual International Conference of the IEEE*. IEEE, 2009, pp. 5748-5751.

[15] R. Nevatia, "Depth measurement by motion stereo," *Computer Graphics and Image Processing*, vol. 5, no. 2, pp. 203-214, 1976.

[16] M. Ye, E. Johns, A. Handa, L. Zhang, P. Pratt, and G.-Z. Yang, "Self-Supervised Siamese Learning on Stereo Image Pairs for Depth Estimation in Robotic Surgery," *ArXiv e-prints,* 2017.

[17] M. Visentini-Scarzanella, T. Sugiura, T. Kaneko, and S. Koto, "Deep monocular 3d reconstruction for assisted navigation in bronchoscopy," *International journal of computer assisted radiology and surgery*, vol. 12, no. 7, pp. 1089-1099, 2017.

[18] D. Chwa, A. P. Dani, and W. E. Dixon, "Range and motion estimation of a monocular camera using static and moving objects," *IEEE Transactions on Control Systems Technology*, vol. 24, no. 4, pp. 1174-1183, 2016.

[19] D. Scaramuzza, F. Fraundorfer, M. Pollefeys, and R. Siegwart, "Absolute scale in structure from motion from a single vehicle mounted camera by exploiting nonholonomic constraints," in *Computer Vision,* 2009 *IEEE* 12*th International Conference on*. IEEE, 2009, pp. 1413-1419.

[20] R. Mazzon, "Real-time structure from motion for monocular and stereo cameras," in *MELECON* 2010-2010 15*th IEEE Mediterranean Electrotechnical Conference*. IEEE, 2010, pp. 498-503.

[21] D. Yang, F. Sun, S. Wang, and J. Zhang, "Simultaneous estimation of ego-motion and vehicle distance by using a monocular camera," *Science China Information Sciences*, vol. 57, no. 5, pp. 1-10, 2014.

[22] Z. Xu, C. Li, X. Zhao, and J. Chen, "Depth measurement using monocular stereo vision system: aspect of spatial discretization," pp. 785 020-785 029.

[23] L. P. Maletsky, J. Sun, and N. A. Morton, "Accuracy of an optical active-marker system to track the relative motion of rigid bodies," *J. Biomech*., vol. 40, no. 3, pp. 682-685, 2007.

[24] A. Saxena, J. Schulte, A. Y. Ng et al., "Depth estimation using monocular and stereo cues." in *IJCAI*, vol. 7, 2007.

[25] R. Hartley, R. Gupta, and T. Chang, "Stereo from uncalibrated cameras," in *Computer Vision and Pattern Recognition,* 1992. *Proceedings CVPR'*92., 1992 *IEEE Computer Society Conference on*. IEEE, 1992, pp. 761-764.

[26] R. I. Hartley and P. Sturm, "Triangulation," *Computer vision and image understanding*, vol. 68, no. 2, pp. 146-157, 1997.

[27] P. A. Beardsley, A. Zisserman, and D. W. Murray, "Navigation using affine structure from motion," in *European Conference on Computer Vision*. Springer, 1994, pp. 85-96.

[28] Dahiteb, "Arthroscopes," 2015. [Online]. Available: http://www.dahiteb.com/products/endoscopy/arthroscopy/arthroscopes.html

[29] G. Litjens, T. Kooi, B. E. Bejnordi, A. A. A. Setio, F. Ciompi, M. Ghafoorian, J. A. Van Der Laak, B. Van Ginneken, and C. I. Sanchez, "A survey on deep learning in medical image analysis," Medical image analysis, vol. 42, pp. 60-88, 2017.

[1] M. Strydom, A. Jaiprakash, R. Crawford, T. Peynot, and J. Roberts, "Towards Robotic Arthroscopy: 'Instrument gap' Segmentation."

[2] M. W. Allen and D. J. Jacofsky, Evolution of Robotics in Arthroplasty. Cham: Springer International Publishing, 2019, p. 13.

[3] B. M. Nigg and W. W. Herzog, Biomechanics of the musculo-skeletal system.

[4] J. A. Reinbolt, J. F. Schutte, B. J. Fregly, B. I. Koh, R. T. Haftka, A. D. George, and K. H. Mitchell, "Determination of patient-specific multi-joint kinematic models through two-level optimization," Journal of Biomechanics, vol. 38, pp. 621-626, 2005.

[5] L. Blankevoort, R. Huiskes, and A. de Lange, "The envelope of passive knee joint motion," Journal of Biomechanics, vol. 21, no. 9, pp. 705-720, January 1988.

[6] F. Janabi-Sharifi, Advances in Motion Sensing and Control for Robotic Applications: Selected Papers from the Symposium on Mechatronics, Robotics, and Control (SMRC'18) —CSME International Congress 2018, May 27-30, 2018 Toronto, Canada. Springer.

[7] R. J. de Asla, L. Wan, H. E. Rubash, and G. Li, "Six DOF in vivo kinematics of the ankle joint complex: Application of a combined dual-orthogonal fluoroscopic and magnetic resonance imaging technique," Journal of Orthopaedic Research, vol. 24, no. 5, pp. 1019-1027, April 2006.

[8] J. Apkarian, S. Naumann, and B. Cairns, "A three-dimensional kinematic and dynamic model of the lower limb," Journal of Biomechanics, vol. 22, no. 2, pp. 143-155, January 1989.

[9] G. R. Scuderi and A. J. Tria, The knee: a comprehensive review. World Scientific, 2010.

[10] G. Li, M. Kozanek, A. Hosseini, F. Liu, S. K. Van de Velde, and H. E. Rubash, "New fluoroscopic imaging technique for investigation of 6 DOF knee kinematics during treadmill gait," Journal of Orthopaedic Surgery and Research, no. 1, 2009.

[11] T.-W. Lu and J. O'connor, "Bone position estimation from skin marker coordinates using global optimisation with joint constraints," Journal of biomechanics, vol. 32, no. 2, pp. 129-134, 1999.

[12] L. P. Maletsky, J. Sun, and N. A. Morton, "Accuracy of an optical active-marker system to track the relative motion of rigid bodies," J. Biomech., vol. 40, no. 3, pp. 682-685, 2007.

[13] G. Nagymáté, T. Tuchband, and R. M. Kiss, "A novel validation and calibration method for motion capture systems based on micro-triangulation," J. Biomech., vol. 74, pp. 16-22, 2018.

[14] R. Yang, Z. Wang, S. Liu, and X. Wu, "Design of an accurate near infrared optical tracking system in surgical navigation," J. Light. Technol., vol. 31, no. 2, pp. 223-231, 2013.

[15] G. Kim, H.-J. Jung, H.-J. Lee, J.-S. Lee, S. Koo, and S.-H. Chang, "Accuracy and reliability of length measurements on threedimensional computed tomography using open-source osirix software," Journal of digital imaging, vol. 25, no. 4, p. 486, 2012.

[16] I. W. Charlton, P. Tate, P. Smyth, and L. Roren, "Repeatability of an optimised lower body model," Gait Posture, vol. 20, no. 2, pp. 213-221, 2004.

[17] H. Kainz, C. P. Carty, L. Modenese, R. N. Boyd, and D. G. Lloyd, "Estimation of the hip joint centre in human motion analysis: A systematic review," Clin. Biomech., no. 4, pp. 319-329.

[18] P. Eichelberger, M. Ferraro, U. Minder, T. Denton, A. Blasimann, F Krause, and H. Baur, "Analysis of accuracy in optical motion capture—a protocol for laboratory setup evaluation," Journal of biomechanics, vol. 49, no. 10, pp. 2085-2088, 2016.

[19] P. Corke, Robotics, vision and control: fundamental algorithms in MATLAB. Berlin: Springer, 2011, vol. 73, no. Book, Whole.

[1] M. Strydom, A. Jaiprakash, R. Crawford, T. Peynot, and J. Roberts, "Towards Robotic Arthroscopy: 'Instrument gap' Segmentation."

[2] K. Kaneko, K. Harada, F. Kanehiro, G. Miyamori, and K. Akachi, "Humanoid robot HRP-3," in 2008 *IEEE/RSJ International Conference on Intelligent Robots and Systems*. IEEE, September 2008, pp. 2471-2478.

[3] B. M. Nigg and W. W. Herzog, Biomechanics of the musculo-skeletal system.

[4] R. J. de Asla, L. Wan, H. E. Rubash, and G. Li, "Six DOF in vivo kinematics of the ankle joint complex: Application of a combined dual-orthogonal fluoroscopic and magnetic resonance imaging technique," *Journal of Orthopaedic Research*, vol. 24, no. 5, pp. 1019-1027, April 2006.

[5] T. R. Jenkyn and A. C. Nicol, "A multi-segment kinematic model of the foot with a novel definition of forefoot motion for use in clinical gait analysis during walking," *Journal of Biomechanics*, vol. 40, pp. 3271-3278, 2007.

[6] J. A. Reinbolt, J. F. Schutte, B. J. Fregly, B. I. Koh, R. T. Haftka, A. D. George, and K. H. Mitchell, "Determination of patient-specific multi-joint kinematic models through two-level optimization," *Journal of Biomechanics*, vol. 38, pp. 621-626, 2005.

[7] J. Apkarian, S. Naumann, and B. Cairns, "A three-dimensional kinematic and dynamic model of the lower limb," *Journal of Biomechanics*, vol. 22, no. 2, pp. 143-155, January 1989.

[8] H. Prather, M. Harris-Hayes, D. M. Hunt, K. Steger-May, V. Mathew, and J. C. Clohisy, "Reliability and Agreement of Hip Range of Motion and Provocative Physical Examination Tests in Asymptomatic Volunteers," *PMRJ*, vol. 2, pp. 888-895, 2010.

[9] G. R. Scuderi and A. J. Tria, *The knee: a comprehensive review*. World Scientific, 2010.

[10] L. Blankevoort, R. Huiskes, and A. de Lange, "The envelope of passive knee joint motion," *Journal of Biomechanics*, vol. 21, no. 9, pp. 705-720, January 1988.

[11] S. Nussbaumer, M. Leunig, J. F. Glatthorn, S. Stauffacher, H. Gerber, and N. A. Maffiuletti, "Validity and test-retest reliability of manual goniometers for measuring passive hip range of motion in femoroacetabular impingement patients." *BMC Musculoskeletal Disorders*, vol. 11, no. 1, p. 194, December 2010.

[12] P. Kouyoumdjian, R. Coulomb, T. Sanchez, and G. Asencio, "Clinical evaluation of hip joint rotation range of motion in adults," *Orthopaedics & Traumatology: Surgery & Research*, vol. 98, no. 1, pp. 17-23, February 2012.

[13] G. Li, M. Kozanek, A. Hosseini, F. Liu, S. K. Van de Velde, and H. E. Rubash, "New fluoroscopic imaging technique for investigation of 6 DOF knee kinematics during treadmill gait," *Journal of Orthopaedic Surgery and Research*, vol. 4, no. 1, p. 6, 2009. [14] M. A. Ali, H. A. Park, and C. S. G. Lee, "Closed-form inverse kinematic joint solution for humanoid robots," in *IEEE/RSJ* 2010 *International Conference on Intelligent Robots and Systems, IROS* 2010—*Conference Proceedings,* 2010, pp. 704-709.

[15] C.-C. Tsai, C.-C. Hung, and C.-F. Chang, "Trajectory planning and control of a 7-DOF robotic manipulator," in 2014 *International Conference on Advanced Robotics and Intelligent Systems* (*ARIS*). IEEE, June 2014, pp. 78-84.

[16] P. Corke, *Robotics, vision and control: fundamental algorithms in MATLAB*. Springer, 2011, vol. 73, no. Book, Whole.

[17] F. Park, "Computational aspects of the product-of-exponentials formula for robot kinematics," *IEEE Transactions on Automatic Control*, vol. 39, no. 3, pp. 643-647, March 1994.

[18] L. Wu, R. Crawford, and J. Roberts, "An analytic approach to converting poe parameters into d 8211; h parameters for seriallink robots," *IEEE Robotics and Automation Letters*, vol. 2, no. 4, pp. 2174-2179, October 2017.

[19] H. Fujie, G. Livesay, M. Fujita, and S. Woo, "Forces and moments in six-DOF at the human knee joint: mathematical description for control," *Journal of biomechanics,* 1996.

[20] Y. Cao, K. Lu, X. Li, and Y. Zang, "Accurate numerical methods for computing 2d and 3d robot workspace," *International Journal of Advanced Robotic Systems*, vol. 8, no. 6, p. 76, 2011.

[21] A. Leardini, J. O'Connor, F. Catani, and S. Giannini, "A geometric model of the human ankle joint," *Journal of Biomechanics*, vol. 32, no. 6, pp. 585-591, June 1999.

[22] D. Wilson, J. Feikes, A. Zavatsky, and J. O'Connor, "The components of passive knee movement are coupled to flexion angle," *Journal of Biomechanics*, vol. 33, no. 4, pp. 465-473, April 2000.

[23] J. Victor, L. Labey, P. Wong, B. Innocenti, and J. Bellemans, "The influence of muscle load on tibiofemoral knee kinematics," *Journal of Orthopaedic Research*, vol. 28, no. 4, pp. n/a-n/a, April 2009.

[24] L. Blankevoort, R. Huiskes, and A. de Lange, "The envelope of passive knee joint motion," *Journal of Biomechanics*, vol. 21, no. 9, pp. 705-720, January 1988.

[25] A. Williams and M. Logan, "Understanding tibio-femoral motion." *The Knee*, vol. 11, no. 2, pp. 81-8, April 2004.

[26] K. Moglo and A. Shirazi-Adl, "Cruciate coupling and screwhome mechanism in passive knee joint during extension?flexion," *Journal of Biomechanics*, vol. 38, no. 5, pp. 1075-1083, May 2005.

[27] P. F. Hill, V. Vedi, A. Williams, H. Iwaki, V. Pinskerova, and M. A. Freeman, "Tibiofemoral movement 2: the loaded and unloaded living knee studied by MRI." *The Journal of bone and joint surgery. British volume*, vol. 82, no. 8, pp. 1196-8, November 2000.

[28] H. Iwaki, V. Pinskerova, and M. A. Freeman, "Tibiofemoral movement 1: the shapes and relative movements of the femur and tibia in the unloaded cadaver knee." *The Journal of bone and joint surgery. British volume*, vol. 82, no. 8, pp. 1189-95, November 2000.

[29] P. Johal, A. Williams, P. Wragg, D. Hunt, and W. Gedroyc, "Tibiofemoral movement in the living knee. A study of weight bearing and non-weight bearing knee kinematics using 'interventional' MRI," *Journal of Biomechanics*, vol. 38, no. 2, pp. 269-276, 2005.

[30] M. Freeman and V. Pinskerova, "The movement of the normal tibio-femoral joint," *Journal of Biomechanics*, vol. 38, no. 2, pp. 197-208, 2005.

[32] A. McPherson, J. Kärrholm, V. Pinskerova, A. Sosna, and S. Martelli, "Imaging knee position using MRI, RSA/CT and 3D digitisation." *Journal of biomechanics*, vol. 38, no. 2, pp. 263-8, February 2005.

[33] M. Strydom, A. Banach, L. Wu, R. Crawford, J. Roberts, and A. Jaiprakash, "Real-time joint motion analysis and instrument tracking for robot-assisted orthopaedic surgery," *arXiv preprint arXiv:*1909.02721, 2019.

[34] M. Robinette and R. Manseur, "Robot-Draw, an Internet-based visualization tool for robotics education," *IEEE Transactions on Education*, vol. 44, no. 1, pp. 29-34, 2001.

[1] M. Strydom, A. Jaiprakash, R. Crawford, T. Peynot, and J. Roberts, "Towards Robotic Arthroscopy: 'Instrument gap' Segmentation," 2016.

[2] B. P. McKeon, J. V. Bono, and J. C. Richmond, Knee Arthroscopy. New York, NY: Springer, 2009, no. Book, Whole.

[3] A. Jaiprakash, J. M. Roberts, and R. Crawford, "Perceptions of Orthopaedic Surgeons on knee arthroscopic surgery," Journal of Orthopaedic Surgery (in press), 2016.

[4] L. Wu, J. Jaiprakash, A. K. Pandey, D. Fontanarosa, Y. Jonmohamadi, M. Antico, M. L. Strydom, A. Razjigaev, F. Sasazawa, J. Roberts, and R. Crawford, "Robotic and image-guided knee arthroscopy," in In Mohammad H. Abedin-Nasab (Ed.), Elsevier's Handbook of Robotic and Image-Guided Surgery. Elsevier, 2018.

[5] B. D. Ward and J. H. Lubowitz, "Basic knee arthroscopy part 3: diagnostic arthroscopy," Arthroscopy techniques, vol. 2, no. 4, pp. e503-e505, 2013.

[6] D. Stoyanov, "Surgical vision," Annals of biomedical engineering, vol. 40, no. 2, pp. 332-345, 2012.

[7] S. Rasool and A. Sourin, "Image-driven virtual simulation of arthroscopy," The Visual Computer, vol. 29, no. 5, pp. 333-344, 2013.

[8] Y. Zhang, Z. Xiong, and F. Wu, "Hybrid structured light for scalable depth sensing," in Image Processing (ICIP), 2012 19th IEEE International Conference on. IEEE, 2012, pp. 17-20.

[9] R. A. Jarvis, "A Perspective on Range Finding Techniques for Computer Vision," IEEE Transactions on Pattern Analysis and Machine Intelligence, vol. PAMI-5, no. 2, pp. 122-139, mar 1983.

[10] "Computer vision and robotics laboratory," Computer; (United States), vol. 6, 1982.

[11] M. Antico, F. Sasazawa, L. Wu, A. Jaiprakash, J. Roberts, R. Crawford, A. K. Pandey, and D. Fontanarosa, "Ultrasound guidance in minimally invasive robotic procedures," Medical Image Analysis, 2019. [Online]. Available: http://www.sciencedirect.com/science/article/pii/S1361841519300027

[12] R. Lewis and A. Johnston, "A scanning laser rangefinder for a robotic vehicle,"1977.

[13] T. Collins and A. Bartoli, "3d reconstruction in laparoscopy with close-range photometric stereo," in International Conference on Medical Image Computing and Computer-Assisted Intervention. Springer, 2012, pp. 634-642.

[14] T. Papadhimitri and P. Favaro, "A new perspective on uncalibrated photometric stereo," in Proceedings of the IEEE Conference on Computer Vision and Pattern Recognition, 2013, pp. 1474-1481.

[15] R. I. Hartley and P. Sturm, "Triangulation," Computer vision and image understanding, vol. 68, no. 2, pp. 146-157, 1997.

[16] C. Morrison, N. Smyth, R. Corish, K. O'Hara, and A. Sellen, "Collaborating with computer vision systems: an exploration of audio feedback," in Proceedings of the 2014 conference on Designing interactive systems. ACM, 2014, pp. 229-238.

[17] A. Bartoli, T. Collins, N. Bourdel, and M. Canis, "Computer assisted minimally invasive surgery: is medical computer vision the answer to improving laparosurgery?" Medical hypotheses, vol. 79, no. 6, pp. 858-863, 2012.

[18] Z. R. Wang, Y. H. Wu, and Y. M. Quan, "Modeling and error analysis of monocular stereo vision system for large-scale workpiece on-machine measurement," in Advanced Materials Research, vol. 102. Trans Tech Publ, 2010, pp. 397-401.

[19] L. M. Zhu, X. M. Zhang, H. Ding, and Y. L. Xiong, "Geometry of signed point-to-surface distance function and its application to surface approximation," Journal of computing and information science in engineering, vol. 10, no. 4, p. 041003, 2010.

[20] M. Visentini-Scarzanella, T. Sugiura, T. Kaneko, and S. Koto, "Deep monocular 3d reconstruction for assisted navigation in bronchoscopy," International journal of computer assisted radiology and surgery, vol. 12, no. 7, pp. 1089-1099, 2017.

[21] Dahiteb, "Arthroscopes," 2015. [Online]. Available: http://www.dahiteb.com/products/endoscopy/arthroscopy/arthroscopes.html

[22] A. Marmol, T. Peynot, A. Eriksson, A. Jaiprakash, J. Roberts, and R. Crawford, "Evaluation of keypoint detectors and descriptors in arthroscopic images for feature-based matching applications," IEEE Robotics and Automation Letters, vol. 2, no. 4, pp. 2135-2142, 2017.

What is claimed is:

1. A surgical joint positioning system for manipulating a subject's joint, the system comprising:

a base configured to be positioned relative to an operating table;

one or more robotic arms coupled to the base and being configured to support and control movement of the subject's joint;

one or more motorized actuating arrangements configured to control movement of the robotic arms to enable the subject's joint to be moved in three different planes of motion;

one or more sensors configured to sense one or more physiological parameters of the subject's joint as the one or more robotic arms move the subject's joint; and one or more controllers comprising a processing assembly and being configured to:

control the one or more motorized actuating arrangements;

receive and process signals indicative of the one or more physiological parameters sensed by the one or more sensors to compute a value of a gap within the subject's joint; and control movement of the one or more robotic arms based on the computed value of the gap.

2. The system of claim 1 wherein a first of the robotic arms comprises a first holder configured to hold a lower portion of the subject's leg; and a second of the robotic arms comprises a second holder configured to hold an upper portion of the subject's leg.

3. The system of claim 2 wherein the second of the robotic arms is configured to provide the second holder with at least two degrees of freedom and the first of the robotic arms is configured to provide the first holder with at least four degrees of freedom.

4. The system of claim 2 wherein the one or more sensors include an arthroscope configured to provide information related to internal joint geometry of the subject.

5. The system of with claim 4 wherein the one or more controllers are configured to receive and process signals from the arthroscope to compute the value of the gap created within the subject's joint and control movement of the first and second of the robotic arms based on the computed value of the gap.

6. The system of claim 1 wherein the one or more controllers are configured to process signals from inside the subject's joint to compute an instrument gap inside the subject's joint.

7. The system of claim 1 wherein the one or more sensors include detection or tracking devices configured to track markers positioned on the subject in response to movement of the one or more robotic arms.

8. The system of claim 1 wherein the one or more sensors comprise one or more medical or robotic devices arranged for viewing, monitoring or tracking features and movements of the subject's joint whereby feedback from the one or more sensors is received and processed by the one or more controllers to further control the one or more motorized actuating arrangements of the robotic arms.

9. The system of claim 1 further comprising a user input interface comprising a human-machine-interface (HMI) configured to receive a user input from an operator, the one or more controllers being configured to process the user input and the signals indicative of the one or more physiological parameters sensed by the one or more sensors in accordance with one or more pre-determined or operator determined rules.

10. A method of operating a surgical joint positioning system for manipulating a subject's joint, the system comprising a base configured to be positioned relative to an operating table, one or more robotic arms coupled to the base and being configured to support and control movement of the subject's joint, one or more motorized actuating arrangements configured to control movement of the robotic arms to enable the joint to be moved in three different planes of motion, and one or more sensors, and one or more controllers comprising a processing assembly, the method comprising:

controlling, with the one or more controllers, the one or more motorized actuating arrangements;

sensing, with the one or more sensors, one or more physiological parameters of the subject's joint as the one or more robotic arms move the subject's joint;

receiving and processing, with the one or more controllers, signals indicative of the one or more physiological parameters sensed by the one or more sensors for computing a value of a gap within the subject's joint; and controlling, with the one or more controllers, movement of the one or more robotic arms based on the computed value of the gap.

11. A surgical assist system comprising:

an arthroscope configured to capture images of a target site, the target site having a region of interest (ROI) with a varying dimension associated therewith;

a tracking system being separate from the arthroscope and configured to track a pose of the arthroscope and a pose of the target site to detect one or more conditions associated with the arthroscope and the target site; and one or more controllers coupled to the arthroscope and to the tracking system and being configured to determine the varying dimension of the ROI at each of a plurality of times based on images from the arthroscope and the conditions detected by the tracking system.

12. The surgical assist system of claim 11 further comprising one or more actuators being configured to move the target site, and wherein the one or more controllers are configured to operate the one or more actuators for physically altering the ROI to bring the varying dimension to a desired value.

13. The surgical assist system of claim 11 wherein the one or more controllers are configured to:

apply a mask to one or more of the images for masking around the ROI; and segment each image to identify the ROI with the varying dimension associated therewith.

14. The surgical assist system of claim 13 wherein the one or more controllers are configured to determine a translation of the arthroscope from the conditions detected by the tracking system.

15. The surgical assist system of claim 14 wherein the one or more controllers are configured to approximate an uncertainty in determination of the varying dimension by taking into account one or more of the following:

errors associated with segmentation of one or more of the images;

errors in the tracking system detecting the translation of the arthroscope; and errors in the tracking system detecting rotational motion of the arthroscope.

16. The surgical assist system of claim 14 wherein the ROI comprises a joint gap and wherein the one or more controllers are configured to determine a width of the joint gap by applying the translation of the arthroscope from the conditions detected by the tracking system.

17. The surgical assist system of claim 11 the one or more controllers are configured to approximate an uncertainty in determination of the varying dimension where minimum and maximum extremes of an uncertainty range reflect a minimum desired limit of the varying dimension and a maximum physical limit for the ROI.

18. The surgical assist system of claim 11 wherein the tracking system comprises one or more of: an optical tracking system comprising optical sensing elements, a magnetic tracking system comprising magnetic sensing elements, or an inertial measurement tracking system comprising inertial sensing elements.

19. The surgical assist system of claim 11 wherein the ROI comprises a gap of a knee or hip joint of a subject's leg and wherein the varying dimension associated with the ROI comprises a width of the gap.

20. The surgical assist system of claim 19 further comprising one or more robotic arms that support the subject's leg and are configured to be controlled by the one or more controllers to move the knee or hip joint.

21. The surgical assist system of claim 20 wherein the one or more controllers are configured to control the one or more robotic arms to move the knee or hip joint to attain a width of the gap.

22. The surgical assist system of claim 20 wherein the tracking system is configured to obtain position data of one or more trackers associated with the knee or hip joint, and the one or more controllers are configured to operate the one or more robotic arms by applying position data from the tracking system to an inverse of a kinematic model of the subject's leg.

23. The surgical assist system of claim 22 wherein the kinematic model of the subject's leg comprises a nine degrees of freedom model of the subject's leg.

24. The surgical assist system of claim 22 wherein the one or more controllers are configured to set one or more parameters of the kinematic model to zero for operating the one or more robotic arms for an arthroscopy procedure.

25. The surgical assist system of claim 20 wherein a first of the robotic arms comprises a first holder for holding a first portion of the subject's leg associated with the knee or hip joint, and wherein one or more trackers of the tracking system are coupled to the first holder, and wherein a second of the robotic arms comprises a second holder for holding a second portion of the subject's leg associated with the knee or hip joint.

26. The surgical assist system of claim 25 wherein the one or more controllers are configured to control one or more of the first and second of the robotic arms to move the subject's leg to a pose corresponding to a predetermined gap width for the knee or hip joint.

27. The surgical assist system of claim 26 further comprising one or more force/torque sensors coupled to the one or more robotic arms and being configured to sense force/torque applied by the one or more robotic arms to the knee or hip joint and wherein the one or more controllers are configured to control the one or more robotic arms to prevent the sensed force/torque from exceeding a predefined safety limit.

28. A method of operating a surgical assist system comprising an arthroscope, a tracking system being separate from the arthroscope, and one or more controllers coupled to the arthroscope and to the tracking system, and the method comprising:

capturing, with the arthroscope, images of a target site having a region of interest (ROI) with a varying dimension associated therewith;

detecting, with the tracking system, one or more conditions associated with the arthroscope and the target site by tracking a pose of the arthroscope and a pose of the target site; and determining, with the one or more controllers, the varying dimension of the ROI at each of a plurality of times based on images from the arthroscope and the conditions detected by the tracking system.

29. A method for operating a system for manipulation of one or more limbs of a subject for assisting a surgeon to deliver a surgical procedure to the subject, the system comprising robotic arms for supporting the one or more limbs of the subject and one or more controllers configured to control the robotic arms, the method comprising:

controlling the robotic arms, with the one or more controllers, for moving the one or more limbs;

receiving, with the one or more controllers, one or more parameters defining a desired pose for the limbs;

applying, with the one or more controllers, the one or more parameters to an inverse kinematic model representing the limbs to determine a position for at least one of the limbs;

applying, with the one or more controllers, the determined position to a forward kinematic model representing the robotic arms to obtain an output related to the desired pose; and controlling, with the one or more controllers, the robotic arms based on the output from the forward kinematic model for moving the one or more limbs to the desired pose.

30. A surgical assist method comprising:

capturing at a sequence of times, electronic images of a target site with an arthroscope, the target site having a region of interest (ROI) with a varying dimension associated therewith;

electronically sensing positions at which the electronic images are captured with a tracking system being separate from the arthroscope and being configured to track a pose of the arthroscope;

analyzing, with one or more controllers, two or more of the captured electronic images and the sensed positions at which the electronic images are captured by the arthroscope and obtaining points related to the ROI; and implementing, with the one or more controllers, a stereo motion procedure with respect to the points of the ROI and based on the stereo motion procedure, determining the varying dimension of the ROI at each of a plurality of times for graphical presentation on a display device.

31. A surgical assist system comprising:

robotic arms configured to support and move one or more limbs of a subject;

an arthroscope configured to generate camera imagery of a target site of the subject;

an optical tracking system configured to acquire positions of the arthroscope, the robotic arms, and the one or more limbs of a subject; and one or more controllers coupled to the robotic arms, the arthroscope, and the optical tracking system and being configured to control movement of the robotic arms in response to evaluating:

the camera imagery of the target site from the arthroscope;

the acquired positions of the arthroscope, the robotic arms, and the one or more limbs of a subject; and a kinematic model of one or both of: the one or more limbs of the subject and the robotic arms.

* * * * *